(12) United States Patent
Jansen et al.

(10) Patent No.: US 8,404,355 B2
(45) Date of Patent: Mar. 26, 2013

(54) METHODS AND SYSTEMS FOR PROCESSING LIGNOCELLULOSIC MATERIALS AND RELATED COMPOSITIONS

(75) Inventors: Robert Jansen, Collinsville, IL (US); Aharon Eyal, Jerusalem (IL); Philippe Lavielle, Burlingame, CA (US)

(73) Assignee: Virdia Ltd, Herzelia (IL)

( * ) Notice: Subject to any disclaimer, the term of this patent is extended or adjusted under 35 U.S.C. 154(b) by 0 days.

(21) Appl. No.: 13/316,327

(22) Filed: Dec. 9, 2011

(65) Prior Publication Data

US 2012/0116063 A1    May 10, 2012

Related U.S. Application Data

(60) Provisional application No. 61/474,298, filed on Apr. 12, 2011, provisional application No. 61/524,350, filed on Aug. 17, 2011, provisional application No. 61/528,257, filed on Aug. 28, 2011, provisional application No. 61/533,078, filed on Sep.

(Continued)

(51) Int. Cl.
*B32B 21/06* (2006.01)
*B32B 21/14* (2006.01)
*B32B 29/00* (2006.01)
*D21C 3/20* (2006.01)

(52) U.S. Cl. ............................. 428/535; 162/72; 162/77

(58) Field of Classification Search .................. 527/103; 428/535; 162/72, 77
See application file for complete search history.

(56) References Cited

U.S. PATENT DOCUMENTS

| 1,544,149 | A | | 6/1925 | Hagglund |
| 2,951,775 | A | | 9/1960 | Apel |
| 3,067,065 | A | | 12/1962 | Kusama |
| 4,174,976 | A | | 11/1979 | Tsao et al. |
| 4,237,110 | A | | 12/1980 | Forster et al. |
| 4,278,471 | A | | 7/1981 | Whittingham |
| 4,291,007 | A | | 9/1981 | Baniel |
| 4,425,136 | A | | 1/1984 | Pearson et al. |
| 4,520,105 | A | | 5/1985 | Sinner et al. |
| 4,901,635 | A | | 2/1990 | Williams |
| 4,908,098 | A | * | 3/1990 | DeLong et al. ................. 162/16 |
| 4,966,650 | A | | 10/1990 | DeLong et al. |
| 5,338,405 | A | | 8/1994 | Patt et al. |
| 5,411,594 | A | | 5/1995 | Brelsford |
| 5,421,964 | A | | 6/1995 | Mahler et al. |
| 5,571,378 | A | | 11/1996 | Elofson et al. |

(Continued)

FOREIGN PATENT DOCUMENTS

CA  2735396 A1  3/2010
EP  0247436 B1  1/1992

(Continued)

OTHER PUBLICATIONS

Weil et al. (Applied Biochemistry and Biotechnology, 68, 1997, 21-40).*

(Continued)

*Primary Examiner* — Liam Heincer
(74) *Attorney, Agent, or Firm* — Wilson Sonsini Goodrich & Rosati

(57) ABSTRACT

A method comprising: (a) providing a lignocellulosic substrate; (b) contacting said lignocellulosic substrate with an extractant comprising a water-soluble organic solvent to form an extracted substrate and a miscella; (c) removing miscella from said extracted substrate; and (d) hydrolyzing said extracted substrate using a chemically catalyzed process.

15 Claims, 12 Drawing Sheets

Related U.S. Application Data 9, 2011, provisional application No. 61/539,196, filed on Sep. 26, 2011, provisional application No. 61/539,239, filed on Sep. 26, 2011, provisional application No. 61/539,272, filed on Sep. 26, 2011, provisional application No. 61/539,854, filed on Sep. 27, 2011, provisional application No. 61/539,861, filed on Sep. 27, 2011, provisional application No. 61/552,402, filed on Oct. 27, 2011, provisional application No. 61/559,529, filed on Nov. 14, 2011, provisional application No. 61/562,931, filed on Nov. 22, 2011.

(56) References Cited

U.S. PATENT DOCUMENTS

| | | | |
|---|---|---|---|
| 5,665,798 A | 9/1997 | Speaks et al. | |
| 5,698,667 A | 12/1997 | Speaks et al. | |
| 5,705,369 A | 1/1998 | Torget et al. | |
| 5,726,046 A | 3/1998 | Farone et al. | |
| 5,820,687 A | 10/1998 | Farone et al. | |
| 5,831,122 A * | 11/1998 | Eyal | 562/580 |
| 5,865,948 A | 2/1999 | Lora et al. | |
| 5,876,505 A | 3/1999 | Klyosov et al. | |
| 6,075,076 A | 6/2000 | Speaks et al. | |
| 6,258,175 B1 | 7/2001 | Lightner | |
| 6,364,999 B1 | 4/2002 | Speaks et al. | |
| 6,391,204 B1 | 5/2002 | Russo, Jr. | |
| 6,416,621 B1 | 7/2002 | Karstens | |
| 6,419,788 B1 | 7/2002 | Wingerson | |
| 6,620,292 B2 | 9/2003 | Wingerson | |
| 6,641,699 B2 | 11/2003 | Speaks et al. | |
| 6,692,578 B2 | 2/2004 | Schmidt et al. | |
| 6,719,880 B2 | 4/2004 | Speaks et al. | |
| 6,936,110 B2 | 8/2005 | Van Thorre | |
| 7,019,170 B2 * | 3/2006 | Eyal et al. | 562/589 |
| 7,198,925 B2 | 4/2007 | Foody | |
| 7,208,570 B2 | 4/2007 | Saviainen | |
| 7,465,791 B1 | 12/2008 | Hallberg et al. | |
| 7,503,981 B2 | 3/2009 | Wyman et al. | |
| 7,717,364 B2 | 5/2010 | Wingerson | |
| 7,718,070 B2 | 5/2010 | Mahnon | |
| 7,993,709 B2 | 8/2011 | Brunet | |
| 8,022,260 B2 | 9/2011 | O'Connor et al. | |
| 8,119,823 B2 * | 2/2012 | Kilambi | 549/489 |
| 8,163,092 B2 | 4/2012 | Baniel et al. | |
| 8,168,840 B2 * | 5/2012 | Brady et al. | 585/242 |
| 2004/0060673 A1 | 4/2004 | Phillips et al. | |
| 2004/0199049 A1 | 10/2004 | Parasher et al. | |
| 2005/0034823 A1 | 2/2005 | Brelid et al. | |
| 2007/0031953 A1 | 2/2007 | Dunson, Jr. et al. | |
| 2008/0029233 A1 | 2/2008 | Wingerson et al. | |
| 2008/0032344 A1 | 2/2008 | Fallavollita | |
| 2008/0057555 A1 | 3/2008 | Nguyen | |
| 2008/0110585 A1 * | 5/2008 | Satyavolu et al. | 162/60 |
| 2008/0190013 A1 * | 8/2008 | Argyropoulos | 44/307 |
| 2008/0202504 A1 | 8/2008 | Hilst | |
| 2008/0227161 A1 | 9/2008 | Levie et al. | |
| 2008/0227182 A1 | 9/2008 | Anderson et al. | |
| 2009/0056889 A1 | 3/2009 | Ren et al. | |
| 2009/0062523 A1 * | 3/2009 | Malkki | 536/56 |
| 2009/0084511 A1 | 4/2009 | Lampinen et al. | |
| 2009/0142848 A1 | 6/2009 | Wyman et al. | |
| 2009/0218055 A1 | 9/2009 | Unsitalo et al. | |
| 2009/0226979 A1 | 9/2009 | Retsina et al. | |
| 2009/0280261 A1 * | 11/2009 | El Kasmi | 427/440 |
| 2009/0286295 A1 | 11/2009 | Medoff et al. | |
| 2010/0024807 A1 | 2/2010 | Burke et al. | |
| 2010/0028557 A1 | 2/2010 | Nagano | |
| 2010/0043782 A1 | 2/2010 | Kilambi et al. | |
| 2010/0069626 A1 | 3/2010 | Kilambi | |
| 2010/0093995 A1 | 4/2010 | Baniel et al. | |
| 2010/0116267 A1 | 5/2010 | Mraz et al. | |
| 2010/0124769 A1 * | 5/2010 | Brown et al. | 435/101 |
| 2010/0144001 A1 | 6/2010 | Horton | |
| 2010/0151527 A1 | 6/2010 | Endo et al. | |
| 2010/0167351 A1 * | 7/2010 | Eyal et al. | 435/72 |
| 2010/0184176 A1 | 7/2010 | Ishida et al. | |
| 2010/0233761 A1 | 9/2010 | Czartoski et al. | |
| 2010/0249390 A1 | 9/2010 | Azuma et al. | |
| 2010/0279361 A1 | 11/2010 | South et al. | |
| 2010/0279372 A1 | 11/2010 | Cho et al. | |
| 2010/0305241 A1 | 12/2010 | Balakshin et al. | |
| 2010/0305242 A1 | 12/2010 | Balakshin et al. | |
| 2010/0305243 A1 | 12/2010 | Balakshin et al. | |
| 2010/0305244 A1 | 12/2010 | Balakshin et al. | |
| 2011/0003348 A1 | 1/2011 | Genta et al. | |
| 2011/0028672 A1 | 2/2011 | Dahlman et al. | |
| 2011/0028710 A1 | 2/2011 | Baniel et al. | |
| 2011/0060132 A1 | 3/2011 | Lewis | |
| 2011/0100359 A1 | 5/2011 | North | |
| 2011/0105737 A1 | 5/2011 | Benjelloun Mlayah et al. | |
| 2011/0114876 A1 * | 5/2011 | Brady et al. | 252/182.12 |
| 2011/0124057 A1 | 5/2011 | Genta et al. | |
| 2011/0129886 A1 | 6/2011 | Howard et al. | |
| 2011/0143412 A1 | 6/2011 | Kim et al. | |
| 2011/0178290 A1 | 7/2011 | Baniel et al. | |
| 2011/0262984 A1 | 10/2011 | Nguyen | |
| 2011/0268652 A1 | 11/2011 | Machhammer et al. | |
| 2011/0271875 A1 | 11/2011 | Ahmed et al. | |
| 2011/0275860 A1 | 11/2011 | Beldring et al. | |
| 2011/0281298 A1 | 11/2011 | Rawls et al. | |
| 2011/0300617 A1 | 12/2011 | Genta et al. | |
| 2011/0318796 A1 | 12/2011 | Walther | |
| 2012/0006320 A1 | 1/2012 | Nguyen | |
| 2012/0023810 A1 | 2/2012 | Fjare et al. | |
| 2012/0055466 A1 | 3/2012 | Cotti et al. | |
| 2012/0058526 A1 | 3/2012 | Jansen et al. | |
| 2012/0110896 A1 * | 5/2012 | Coronella et al. | 44/307 |

FOREIGN PATENT DOCUMENTS

| | | |
|---|---|---|
| EP | 1918031 A1 | 5/2008 |
| WO | WO 93/05186 A1 | 3/1993 |
| WO | WO 93/13265 A1 | 7/1993 |
| WO | WO 95/02726 A1 | 1/1995 |
| WO | WO 96/41052 A1 | 12/1996 |
| WO | WO 97/13732 A2 | 4/1997 |
| WO | WO 97/13732 A3 | 5/1997 |
| WO | WO 01/25143 A1 | 4/2001 |
| WO | WO 2004/050983 A1 | 6/2004 |
| WO | WO 2006/034581 A1 | 4/2006 |
| WO | WO 2006/038863 A1 | 4/2006 |
| WO | WO 2006/056838 A1 | 6/2006 |
| WO | WO 2008/111045 A1 | 9/2008 |
| WO | WO 2008/123419 A1 | 10/2008 |
| WO | WO 2008/131229 A1 | 10/2008 |
| WO | WO 2008/137639 A1 | 11/2008 |
| WO | WO 2008/144903 A1 | 12/2008 |
| WO | WO 2009/028969 A1 | 3/2009 |
| WO | WO 2009/030713 A1 | 3/2009 |
| WO | WO 2009/031164 A1 | 3/2009 |
| WO | WO 2009/036674 A1 | 3/2009 |
| WO | WO 2009/125400 A2 | 10/2009 |
| WO | WO 2009/142837 A2 | 11/2009 |
| WO | WO 2009156464 A2 * | 12/2009 |
| WO | WO 2009/125400 A3 | 1/2010 |
| WO | WO 2010/006840 A2 | 1/2010 |
| WO | WO 2010/009343 A2 | 1/2010 |
| WO | WO 2010/020977 A2 | 2/2010 |
| WO | WO 2009/142837 A3 | 3/2010 |
| WO | WO 2010/026244 A1 | 3/2010 |
| WO | WO 2010/026572 A1 | 3/2010 |
| WO | WO 2010/009343 A3 | 4/2010 |
| WO | WO 2010/034055 A1 | 4/2010 |
| WO | WO 2010/043424 A1 | 4/2010 |
| WO | WO 2010/045576 A2 | 4/2010 |
| WO | WO 2010/006840 A3 | 5/2010 |
| WO | WO 2010/060183 A1 | 6/2010 |
| WO | WO 2010/064229 A2 | 6/2010 |
| WO | WO 2010/045576 A3 | 7/2010 |
| WO | WO 2010/064229 A3 | 7/2010 |
| WO | WO 2010/020977 A3 | 10/2010 |
| WO | WO 2010/113129 A2 | 10/2010 |
| WO | WO 2010/113129 A3 | 10/2010 |
| WO | WO 2010/113130 A2 | 10/2010 |

| | | | |
|---|---|---|---|
| WO | WO 2010/122554 A1 | 10/2010 |
| WO | WO 2010/135804 A1 | 12/2010 |
| WO | WO 2010/135805 A1 | 12/2010 |
| WO | WO 2010/135806 A1 | 12/2010 |
| WO | WO 2010/135807 A1 | 12/2010 |
| WO | WO 2010/135832 A1 | 12/2010 |
| WO | WO 2010/135833 A1 | 12/2010 |
| WO | WO 2010/113130 A3 | 1/2011 |
| WO | WO 2011/007043 A1 | 1/2011 |
| WO | WO 2011/007369 A1 | 1/2011 |
| WO | WO 2011/017587 A1 | 2/2011 |
| WO | WO 2011/028554 A1 | 3/2011 |
| WO | WO 2011/039751 A2 | 4/2011 |
| WO | WO 2011/066487 A1 | 6/2011 |
| WO | WO 2011/070602 A1 | 6/2011 |
| WO | WO 2011/080131 A2 | 7/2011 |
| WO | WO 2011/089589 A1 | 7/2011 |
| WO | WO 2011/097719 A1 | 8/2011 |
| WO | WO 2011/080131 A3 | 9/2011 |
| WO | WO 2011/111189 A1 | 9/2011 |
| WO | WO 2011/111190 A1 | 9/2011 |
| WO | WO 2011/039751 A3 | 10/2011 |
| WO | WO 2011/140222 A1 | 11/2011 |
| WO | WO 2011/163084 A1 | 12/2011 |
| WO | WO 2012/015575 A1 | 2/2012 |

OTHER PUBLICATIONS

Alvarez et al. (J. Anal. Appl. Pyrolysis 74, 2005, 337-343).*
U.S. Appl. No. 61/473,134, filed Apr. 7, 2011, Eyal.
U.S. Appl. No. 61/524,350, filed Aug. 17, 2011, Eyal et al.
U.S. Appl. No. 61/528,257, filed Aug. 28, 2011, Jansen et al.
U.S. Appl. No. 61/539,196, filed Sep. 26, 2011, Jansen et al.
U.S. Appl. No. 61/539,239, filed Sep. 26, 2011, Jansen et al.
U.S. Appl. No. 61/539,272, filed Sep. 26, 2011, Jansen et al.
Aden, et al. Lignocellulosic Biomass to Ethanol Process Design and Economics Utilizing Co-Current Dilute Acid Prehydrolysis and Enzymatic Hydrolysis for Corn Stover. National Renewable Energy Laboratory, NREL is a U.S. Department of Energy Laboratory Operated by Midwest Research Institute. Jun. 2002.
Ahmed, et al. A simplified method for accurate determination of cell wall uronide content. Journal of Food Biochemistry.1977; 1:361-365.
Albersheim. Metabolism of the Pectic Substances. For the degree of Doctor of Philosophy, California Institute of Technology Pasadena, California, 1959.
Albertson, et al. Addition Compounds of Sulfur Dioxide. Sep. 1943; 65:1687-1690.
Alizadeh, et al. Pretreatment of Switchgrass by Ammonia Fiber Explosion (AFEX). Applied Biochemistry and Biotechnology. 2005; 5(121-124):1133-1142.
Allsopp, et al. 130. The constitution of the cambium, the new wood and the mature sapwood of the common ash, the common elm and the scotch pine. May 10, 1940; 1078-1084.
Amidon, et al. Biorefinery: Conversion of Woody Biomass to Chemicals, Energy and Materials. Journal of Biobased Materials and Bioenergy. 2008; 2:100-120.
Anderson. The isolation of pectic substances from wood. 1935; 531-539.
ASTM. Site search ethanol extractives. Accessed Jun. 12, 2011. www.astm.org.
Atchison, et al. Innovative Methods for Corn Stover Collecting, Handling, Storing and Transporting, Mar. 2003. National Renewable Energy Laboratory. Apr. 2004.
Bakker. Advanced physical/chemical fractionation. Workshop of the EU FP6, Integrated Project Biosynergy. Nov. 17, 2011.
Barta, et al. Catalytic disassembly of an organosolv lignin via hydrogen transfer from supercritical methanol. Green Chem. 2010; 12:1640-1647.
Barton. CRC handbook of solubility parameters and other cohesion parameters. CRC Press. Boca Raton. 1991; 122-138.
Berthold, et al. Association of water to polar groups; estimations by an adsorption model for ligno-cellulosic materials. Colloids Surfaces A:Physicochem. Eng. Aspects. 1996; 112:117-129.
Bilanicova, et al. Improvements in Enzymatic Preparation of Alkyl Glycosides. Czech J. Food Sci. 20101 28(1): 69-73.
Brito, et al. Chemical composition changes in eucalyptus and pinus woods submitted to heat treatment. Bioresource Technology. 2008; 99:8545-8548.
Brownell, et al. Steam-Explosion Pretreatment of Wood: Effect of Chip Size, Acid, Moisture Content and Pressure Drop. Biotechnology and Bioengineering. 1986; XXVIII:792-801.
Campbell. The Degradation of wood by simultaneous action of ethyl alcohol and hydrochloric acid. 1929; 1225-1232.
Cardona, et al. Production of bioethanol from sugarcane bagasse: Status and perspectives. Bioresource Technology. 2010; 101:4754-4766.
Carvalheiro, et al. Hemicellulose biorefineries: a review on biomass pretreatments. Journal of Scientific and Industrial Research. 2008; 67:849-864.
Castro, et al. Antioxidant activity of liquors from steam explosion of *Olea europea* wood. Wood sci technol. 2008; 42:579-592.
Chalov. Sorption of Hydrogen Chloride by moist lignocellulose. SB. TR. VNII Gidroliza Rastitel'n. Mater. 1975; 25:41-49.
Chambost, et al. Guided tour: Implementing the forest biorefinery (FBR) at existing pulp and paper mills. Pulp & Paper Canada. 2008; 109(7):1-9.
Chandra, et al. The characterization of pretreated lignocellulosic substrates prior to enzymatic hydrolysis, part 1: a modified Simons' staining technique. Biotechnol Prog. 2008; 24:1178-1185.
Chang, et al. Modification of wood with isopropyl glycidyl ether and its effects on decay resistance and light stability. Bioresource Technology. 2006; 97:1265-1271.
Coetzee, et al. Determination of pectin content of eucalyptus wood. Holzforschung. 2011; 65:327-331.
Conner, et al. Kinetic modeling of hardwood prehydrolysis. Part II. Xylan removal by dilute hydrochloric acid prehydrolysis. Wood and Fiber Science. 1985; 17(4):540-548.
David, et al. Cross-Polarization/Magic Angle Spinning (CP/MAS) 13C Nuclear Magnetic Resonance (NMR) Analysis of Chars from Alkaline-Treated Pyrolyzed Softwood. Energy & Fuels. 2009; 23:498-501.
De Wild, et al. Pyrolysis of Wheat Straw—Derived Organosolv Lignin. Ch. 5, pp. 101-122. 2011.
Dimov, et al. Influence of the amount and concentration of hydrochloric acid on the composition of wheat straw during pre-hydrolysis. Chem. Technol. Inst., Sofia, Bulg. Papier (Paris) (1960), 14 673-6. CODEN: PPERA3 ISSN: 0370-1174. Abstract only.
Draucker. Novel solvent systems for the development of sustainable technologies. Georgia Institute of Technology. Aug. 2007.
Eggeman, et al. Process and economic analysis of pretreatment technologies. Bio. Tech. 2005; 96:2019-2025.
Elliott, et al. Pretreatment technologies for advancing anaerobic digestion of pulp and paper biotreatment residues. Water Research. 2007; 41:4273-4286.
Esteves, et al. Chemistry and ecotoxicity of heat-treated pine wood extractives. Wood Sci Technol. Jul. 11, 2010. DOI 10.1007/s00226-010-0356-0.
Excoffier, et al. Saccharification of Steam-Exploded Poplar Wood. Biotechnology and bioengineering. Dec. 20, 1991; 38(11):1308-1317.
Farrell, et al. Solving Pitch Problems in Pulp and Paper Processes by the Use of Enzymes or Fungi. Advances in Biochemical Engineering/Biochemical Engineering/1997/pp. 198-212.
Fenner, et al. Examination of the Thermal Decomposition of Kraft Pine Lignin by Fourier Transform Infrared Evolved Gas Analysis. J. Agric. Food Chem. 1981; 29:846-849.
Ferraz, et al. Estimating the chemical composition of biodegraded pine and eucalyptus wood by DRIFT spectroscopy and multivariate analysis. Bioresource Technology. 2000; 74:201-212.
Fierro, et al. Methodical study of the chemical activation of Kraft lignin with KOH and NaOH. Microporous and Mesoporous Materials. 2007; 101:419-431.
Froass, et al. Nuclear Magnetic Resonance Studies. 4. Analysis of Residual Lignin after Kraft Pulping. Ind. Eng. Chem. Res. 1998; 37:3388-3394.

Glazkova, et al. Effect of temperature on the extraction of prehydrolysis products from lignocellulose chips. Gidroliznaya i Lesokhimicheskaya Promyshlennost (1974), (6), 12-13. CODEN: GLKPA2 ISSN: 0016-9706. Abstract only.

Goncalves, et al. Hydroxymethylation and oxidation of Organosolv lignins and utilization of the products. Bioresource Technology. 2001; 79:103-111.

Gonzalez-Serrano, et al. Development of Porosity upon Chemical Activation of Kraft Lignin with ZnC12. Ind. Eng. Chem. Res. 1997; 36:4832-4838.

Gonzalez-Serrano, et al. Removal of water pollutants with activated carbons prepared from H3PO4 activation of lignin from kraft black liquors. Water Research. 2004; 38:3043-3050.

Grant, et al. Tall oil production and processing. Grant and Hockh's Chemical Dictionary 5th ed. 1987.

Gretland, et al. Characterisation of lignosulphonates and sulphonated kraft lignin by hydrophobic interaction chromatography. 2005.

Gutierrez, et al. Analysis of Lipophilic extractives from wood and pitch deposits by solid-phase extraction and gas chromatography. J. of Chromatography A. 1998; 823:449-455.

Gutierrez, et al. Enzymatic Removal of Free and Conjugated Sterols Forming Pitch Deposits in Environmentally Sound Bleaching of Eucalypt Paper Pulp. Environ. Sci. Technol. 2006; 40:3416-3422.

Gutierrez, et al. Fungal Degradation of Lipophilic Extractives in *Eucalyptus globulus* Wood. Applied and environmental microbiology. Apr. 1999; 65(4):1367-1371.

Gutierrez, et al. Microbial and enzymatic control of pitch in the pulp and paper industry. Appl Microbiol Biotechnol. 2009; 82:1005-1018.

Gutierrez, et al. The biotechnological control of pitch in paper pulp manufacturing. TRENDS in Biotechnology. 2001; 19(9):340-348.

Haensel, et al. Pyrolysis of wood-based polymer compounds. J. Anal. Appl. Pyrolysis. 2010; 87:124-128.

Hage, et al. Effects of process severity on the chemical structure of *Miscanthus* ethanol organosolv lignin. Polymer Degradation and Stability. 2010; 95:997-1003.

Hagglund. The Decomposition of Wood by Acids wood Saccharification. Chemistry of Wood. New York: Academic Press, 1951. 631. Chapter IV. 390-413.

Drenkow. Wood Saccharification. A Modified Rheinau Process. 1976. DouglasDrenkow.com/write2a.html.

Hall, et al. Wood saccharification. USDA. Unasylva. 2007; 10(1).

Hallac, et al. Biomass Characterization and Organosolv Pretreatment of *Buddleja davidii*. School of Chemistry and Biochemistry, Institute of Paper Science and Technology, Georgia Institute of Technology, Atlanta, GA. 2009.

Hallac, et al. Chemical Transformations of *Buddleja davidii* Lignin during Ethanol Organosolv Pretreatment. Energy Fuels. 2010; 24:2723-2732.

Hallac. Fundamental understanding of the biochemical conversion of *Buddleja davidii* to fermentable sugars. Georgia Institute of Technology. May 2011.

Harris, et al. The Madison Wood-Sugar Process. US Dept. of Agriculture. Jun. 1946; 1-21.

Hasegawa, et al. New Pretreatment Methods Combining a Hot Water Treatment and Water/Acetone Extraction for Thermo-Chemical Conversion of Biomass. Energy & Fuels. 2004; 18:755-760.

Hatcher. Dipolar-Dephasing $^{13}$C NMR Studies of Decomposed Wood and Coalified Xylem Tissue:Evidence for Chemical Structural Changes Associated with Defunctionalization of Lignin Structural Units during Coalification. Energy. Fuels. 1988; 2:48-58.

Hendriks, et al. Pretreatments to enhance the digestibility of lignocellulosic biomass. Bioresource Technology. 2009; 100:10-18.

Holm, et al. Ionic Liquids in the Pretreatment of Lignocellulosic Biomass. chapter 24, 545-560. 2011.

Hongzhang, et al. Unpolluted fractionation of wheat straw by steam explosion and ethanol extraction. Bioresource technology. 2007; 98:666-676.

Hyttinen, et al. Comparison of VOC emissions between air-dried and heat-treated Norway spruce (*Picea abies*), Scots pine (*Pinus sylvesteris*) and European aspen (*Populus tremula*) wood. Atmospheric Environment. 2010; 44:5028-5033.

Ibarra, et al. Isolation of high-purity residual lignins from eucalypt paper pulps by cellulase and proteinase treatments followed by solvent extraction. Enzyme and Microbial Technology. 2004; 35:173-181.

Ibrahim, et al. Comparison of alkaline pulping with steam explosion for glucose production from rice straw. Carbohydrate Polymers. 2011; 83:720-726.

Intechfibres. Microscopic Analysis of pulps, papers and boards: For a Fundamental Knowledge of Fibre Structure. IntechFibers, research in fibers Nov. 2007.

Jacobsen, et al. Cellulose and Hemicellulose Hydrolysis Models for Application to Current and Novel Pretreatment Processes. Applied Biochemistry and Bio. 2000; 84-86:81-96.

Jiang, et al. Perdeuterated pyridinium molten salt (ionic liquid) for direct dissolution and NMR analysis of plant cell walls. Green Chem. 2009; 11:1762-1766.

Kadam, et al. Generating Process and Economic Data Needed for Preliminary Design of PureVision Biorefineries. DOE Project No. DE-FG36-05GO85004, Final Nonproprietary Technical Report. Dec. 28, 2007.

Kauper. Sulfur-free lignin from alkaline pulping as emulsifiers. The international Lignin Institute, 5th international Forum' Sep. 7, 2000, Bordeaux (France).

Keller, et al. Microbial Pretreatment of Biomass, Potential for Reducing Severity. Applied Biochemistry and Biotechnology. 2003; 105-108:27-41.

Kim, et al. Pretreatment and fractionation of corn stover by ammonia recycle percolation process. Bioresource Technology. 2005; 96:2007-2013.

Kim, et al. Pretreatment of Corn Stover by Low-Liquid Ammonia Recycle Percolation Process. Applied Biochemistry and Biotechnology. 2006; 133:41-57.

Kim, et al. Supercritical CO2 pretreatment of lignocellulose enhances enzymatic cellulose hydrolysis. Bioresource Technology. 2001; 77:139-144.

Kintner III, et al. Carbohydrate Interference and Its Correction in Pectin Analysis Using the m-Hydroxydiphenyl Method. Journal of Food Science. 1982; 47:756-759.

Kjellstrand, et al. Development of toxic degradation products during heat sterilization of glucose-containing fluids for peritoneal dialysis: influence of time and temperature. Pent Dial Int. 1995;15(1):26-32.

Koski. Applicability of crude tall oil for wood protection. Acta Univ. Oul. C 293, 2008, Oulun Yliopisto, Oulu 2008.

Kovalev, et al. Reaction of sprucewood pulp with hydrogen chloride dissolved in dichloroethane. Sbornik Trudov Ukrainskogo Nauchno-Issledovatel'skogo Instituta Tsellyulozno-Bumazhnoi Promyshlennosti (1966), No. 9 51-69. CODEN: SUTBAU ISSN: 0453-8560. Abstract only.

Krall, et al. Pectin Hydrolysis: Effect of Temperature, Degree of Methylation, pH, and Calcium on Hydrolysis Rates. J. Agric. Food Chem. 1998; 46:1311-1315.

Kubo, et al. Preparation of carbon fibers from softwood lignin by atmospheric acetic acid pulping. Carbon. 1998; 36(7-8):1119-1124.

Kubo, et al. Surface Porosity of Lignin/PP Blend Carbon Fibers. Journal of Wood Chemistry and Technology. 2007; 27: 257-271.

Kubo, et al. Thermal Decomposition Study of Isolated Lignin Using Temperature Modulated TGA. Journal of Wood Chemistry and Technology. 2008; 28(2):106-121.

Kumar, et al. Methods for Pretreatment of Lignocellulosic Biomass for Efficient Hydrolysis and Biofuel Production. Ind. Eng. Chem. Res. 2009; 48:3713-3729.

Kunamneni, et al. Fungal laccase—a versatile enzyme for biotechnological applications. Communicating Current Research and Educational Topics and Trends in Applied Microbiology. 2007; 233-245.

Laine. Structures of hemicelluloses and pectins in wood and pulp. degree of Doctor of Science, Helsinki University of Technology,Department of Chemical Technology, Laboratory of Organic Chemistry, Espoo, Finland, 2005.

Lam, et al. Kinetic Modeling of Pseudolignin Formation in Steam Exploded Woody Biomass. 2011.

Lam. Steam explosion of biomass to produce durable wood pellets. The University of British Columbia (Vancouver). May 2011.

Lee, et al. Ionic Liquid-Mediated Selective Extraction of Lignin From Wood Leading to Enhanced Enzymatic Cellulose Hydrolysis. Biotechnology and Bioengineering. Apr. 1, 2009; 102(5):1368-1376.

Li, et al. Ethanol Organosolv Lignin-based Rigid Polyurethane Foam Reinforced with Cellulose Nanowhiskers. Institute of Paper Science and Technology. 2011.

Li, et al. Kraft Lignin-based Rigid Polyurethane Foam. Institute of Paper Science and Technology. 2011.

Li, et al. Lignin depolymerization/repolymerization and its critical role for delignification of aspen wood by steam explosion. Bioresource Technology 98 (2007) 3061-3068.

Li, et al. Steam explosion lignins; their extraction, structure and potential as feedstock for biodiesel and chemicals. Bioresource Technology. 2009.

Liu, et al. Citrus Pectin: Characterization and Inhibitory Effect on Fibroblast Growth Factor-Receptor Interaction. J. Agric. Food Chem. 2001; 49:3051-3057.

Liu, et al. Partial flow of compressed-hot water through corn stover to enhance hemicellulose sugar recovery and enzymatic digestibility of cellulose. Bioresource Technology. 2005; 96:1978-1985.

Lora., et al. Autohydrolysis sf aspen milled wood lignin. AYMANC. An. J. Chem. 1980; 58:669-676.

Lynd. Overview and evaluation of fuel ethanol from cellulosic biomass technology economics the environment and policy. Annu. Rev. Energy Environ. 1996; 21:403-65.

Manninen, et al. Comparing the VOC emissions between air-dried and heat-treated Scots pine wood. Atmospheric Environment. 2002; 36:1763-1768.

Marchal, et al. Conversion into acetone and butanol of lignocellulosic substrates pretreated by steam explosion. Biotechno!ogy Letters. 1986; 8(5):365-370.

Martin, et al. Engineering a mevalonate pathway in *Escherichia coli* for production of terpenoids. Nature Biotechnology. 2003; 21(7):796-802.

Martinez-Inigo, et al. Time course of fungal removal of lipophilic extractives from *Eucalyptus globulus* wood. Journal of Biotechnology. 2000; 84:119-126.

Martin-Sampedro, et al. Combination of steam explosion and laccase-mediator treatments prior to *Eucalyptus globulus* kraft pulping. Bioresource Technology 2011; 102:7183-7189.

Masura. A mathematical model for neutral sulfite pulping of various broadleaved wood species. Wood Science and Technology. 1998; 32:1-13.

McFeeters, et al. Measurement of Pectin Methylation in Plant Cell Walls. Analytical biochemistry. 1984; 139:212-2 17.

McMillan. Processes for Pretreating Lignocellulosic Biomass: A Review. National Renewable Energy Laboratory, A Division of Midwest Research Institute, Operated for the U.S. Department of Energy, Under Contract No. DE-AC02-83CH 10093. Nov. 1992.

Mendes, et al. Extraction of hemicelluloses prior to kraft cooking: a step for an integrated biorefinery in the pulp mill. XXI Tecnicelpa Conference and Exhibition/VI CIADICYP 2010. Oct. 12-15, 2010.

Mesfun. Integration of hot water extraction in biomass based CHP plants-possibilities for green-chemicals and increased electricity production. Integration of hot water extraction in biomass based CHP plants-possibilities for green-chemicals and increased electricity production. 2010.

Miller. Structure of Wood. Chapter 2. 2009.

Mooney, et al. The effect of initial pore volume and lignin content on the enzymatic hydrolysis of softwoods. Bioresource Technology. 1998; 64:113-119.

Mosier, et al. Features of promising technologies for pretreatment of lignocellulosic biomass. Bioresource Technology. 2005;96:673-686.

Munoz, et al. Bioethanol production from bio-organosolv pulps of *Pinus radiata* and *Acacia dealbata*. J Chem Technol Biotechnol. 2007; 82:767-774.

Nagamatsu, et al. Cascade-type flow of lignocellulosic components through the phase-separation system. J. Adv. Sci. 2001; 13(3):517-520.

Nagy, et al. Characterization of CO2 precipitated Kraft lignin to promote its utilization. Green Chem. 2010; 12:31-34.

Nogueira, et al. Crude tall-oil sodium salts micellization in aqueous solutions studied by static and dynamic light scattering. Colloids and Surfaces A: Physicochemical and Engineering Aspects. 2001; 191: 263-268.

Norman, et al. LXXIV. Studies on pectin. V. The hydrolysis of pectin. May 1, 1930; 649-660.

Oh, et al. Pretreatment of Lignocellulosic Biomass using Combination of Ammonia Recycled Percolation and Dilute-Acid Process. J. Int. Eng. Chem. 2002; 8(1):64-70.

Oliet, et al. Solvent effects in autocatalyzed alcohol—water pulping comparative study between ethanol and methanol as delignifying agents. Chemical Engineering Journal. 2002; 87:157-162.

On, et al. Studies on pulp and paper mill fiber residues as resources. (II). Studies on acid hydrolysis of sludge. Coll. Eng., Jeonbuk Univ., Jenzu, S. Korea. Polpu, Chongi Gisul (1985), 17(1), 38-44. CODEN: PCGIDY ISSN: 0253-3200. Abstract only.

Ong. Conversion of lignocellulosic biomass to fuel ethanol—a brief review. The planter kuala lumpur. 2004; 80(941):517-524.

Pan, et al. Biorefining of Softwoods Using Ethanol Organosolv Pulping: Preliminary Evaluation of Process Streams for Manufacture of Fuel-Grade Ethanol and Co-Products. Biotechnology and bioengineering. May 20, 2005; 90(4).

Papajannopoulous, et al. GC-MS analysis of oleoresin of three Greek pine species. Holz als Roh- und Werkstoff 2001; 59:443-446.

Pasquini, et al. Extraction of lignin from sugar cane bagasse and *Pinus taeda* wood chips using ethanol—water mixtures and carbon dioxide at high pressures. J. Of Supercritical Fluids. 2005; 36:31-39.

Pasquini, et al. Sugar cane bagasse pulping using supercritical CO2 associated with co-solvent 1-butanol/water. J. of Supercritical Fluids. 2005; 34:125-131.

Pepper, et al. The Isolation of a Representative Lignin Fraction From Wood and Straw Meals. Canadian J. of Chemistry. 1962; 40:1026-1028.

Peterson, et al. Thermochemical biofuel production in hydrothermal media: A review of sub and supercritical water technologies. Energy & Environmental Science. 2008; 1:32-65.

Ping, et al. Evaluation of grape stalks as a bioresource. Industrial Crops and Products. 2011; 33:200-204.

Pulping and Bleaching, PSE 476 powerpoint. 2011.

Pye. The Alcell Process—A Proven Alternative to Kraft Pulping. 1990 Pulping Conference, TAPPI Proceedings. 991-996.

Quinde. Enzymes in the pulp and paper industry: a review. 1994.

Ragauskas, et al. From wood to fuels Integrating biofuels and pulp production. Industrial biotechnology. 2006; 2(1):55-65.

Ragauskas. Chemical composition of wood. Georgia Institute of Technology. Accessed Nov. 16, 2011.

Reinhold. SEC of lignins. Mainz, Germany. 2007.

Reinhold. SEC of lignins. Mainz, Germany. Powerpoint. 2007.

Robertson. The fractional extraction and quantitative determination of pectic substances in grapes and musts. Am. J. Enol. Vitic. 1979; 30(3):182-186.

Robinson. Pretreatment and fermentation of Douglas-Fir whitewood and bark feedstocks for ethanol production. University of British Colombia. Sep. 2003. 1-222.

Saake, et al. Lignin. Ullman's Encyclopedia of Industrial Chemistry. 2007; 21:22-36.

Saariaho. Resonance raman spectroscopy in the analysis of residual lignin and other unsaturated structures in chemical pulps. Helsinki University of Technology (Espoo, Finland) on the of Jan. 14, 2005.

Saha, et al. Dilute Acid Pretreatment, Enzymatic Saccharification, and Fermentation of Rice Hulls to Ethanol. Biotechnol. Prog. 2005; 21:816-822.

Saltberg, et al. Removal of metal ions from wood chips during acidic leaching 1:Comparison between Scandinavian softwood, birch and eucalyptus. Nordic Pulp and Paper Research J. 2006; 21(4):507-512.

Saltberg, et al. Removal of metal ions from wood chips during acidic leaching 2: Modeling leaching of calcium ions from softwood chips. Nordic Pulp and Paper Research J. 2006; 21(4):513-519.

Samuel, et al. Structural Characterization and Comparison of Switchgrass Ball-milled Lignin Before and after Dilute Acid Pretreatment. Appli. Micr. BioTech. 2010, 162:62-74.

Sannigrahi, et al. Cellulosic biorefineries—unleashing lignin opportunities. Current Opinion in Environmental Sustainability. 2010; 2:383-393.

Sannigrahi, et al. Effects of Two-Stage Dilute Acid Pretreatment on the Structure and Composition of Lignin and Cellulose in Loblolly Pine. Bioenerg. Res. 2008; 1:205-214.

Sannigrahi, et al. Pseudo-lignin and pretreatment chemistry. Energy Environ. Sci. 2011; 4:1306-1310.

Scaringelli, et al. Pre-hydrolysis of sweetgum wood—an integrated approach to the conversion of lignocellulose from wood into useful chemicals. Report (1979), (NSF/RA-790218; Order No. PB80-108640), 38 pp. From: Gov. Rep. Announce. Index (U. S.) 1980, 80(5), 810. Abstract only.

Schoenemann. The New Rheinau Wood Saccharification Process. Institute of Chemical Technology. Jul. 27, 1953; 1-49.

Scifinder. Steam pretreatment of wood in relation to enzymatic hydrolysis. Final report. Energy Res. Abstr. 1989, 14(17), Abstr. No. 35904.

Sendich, et al. Recent process improvements for the ammonia fiber expansion (AFEX) process and resulting reductions in minimum ethanol selling price. Bio. Tech. 2008; 99:8429-8435.

Shatalov, et al. Kinetics of organosolv delignification of fibre crop *Arundo donax* L. Industrial Crops and Products. 2005; 21:203-210.

Shimizu, et al. Integrated process for total utilization of wood components by steam-explosion pretreatment. Biomass and bioenergy. 1998; 14(3):195-203.

Sidiras, et al. Simulation of acid-catalysed organosolv fractionation of wheat straw. Bioresource Technology. 2004; 94:91-98.

Singh, et al. Visualization of Biomass Solubilization and Cellulose Regeneration During Ionic Liquid Pretreatment of Switchgrass. Biotechnology and Bioengineering. Sep. 1, 2009; 104(1):68-75.

Sluiter, et al. Determination of Sugars, Byproducts, and Degradation Products in Liquid Fraction Process Samples, Laboratory Analytical Procedure (LAP), Issue Date: Dec. 8, 2006. Technical Report, NREL/TP-510-42623, Jan. 1, 2008.

Sluiter, et al. Determination of Sugars, Byproducts, and Degradation Products in Liquid Fraction Process Samples. Laboratory Analytical Procedure (LAP), Contract No. DE-AC36-99-G010337. Issue Date: Dec. 8, 2006.

Sluiter, et al. Determination of Total Solids in Biomass and Total Dissolved Solids in Liquid Process Samples, Laboratory Analytical Procedure (LAP), Issue Date: Mar. 31, 2008. Technical Report, NREL/TP-510-42621, Revised Mar. 2008.

Srndovic. Ultrastructure of the primary cell wall of softwood fibres studied using dynamic FT_IR spectroscopy. Licentiate Thesis, Royal Institute of Technology. Stockholm 2008.

Structure of Wood. US Department of Agriculture, Forest Service, Forest Products Laboratory, Research Note FPL-04. Mar. 1980.

Sudo, et al. A New Modification Method of Exploded Lignin for the Preparation of a Carbon Fiber Precursor. Journal of Applied Polymer Science. 1993; 48:1485-1491.

Taherzadeh, et al. Pretreatment of Lignocellulosic Wastes to Improve Ethanol and Biogas Production: A Review. Int. J. Mol. Sci. 2008; 9:1621-1651; DOI: 10.3390/ijms9091621.

Tanahashi. Characterization and degradation of mechanisms of wood components by steam explosion and utilization of exploded wood. Wood research:bulletin of the wood research institute Kyoto university. 1990; 77:49-117.

Tanaka, et al. Effect of Pore Size in Substrate and Diffusion of Enzyme on Hydrolysis of Cellulosic Materials with Cellulases. Biotechnology and Bioengineering. 1998; 32:698-706.

Tanase, et al. Mass Balance of Extractives Around Impressafiner in Mill and Pilot Scale. 2009. 1-6.

Tang, et al. Effect of Inorganic Salts on Pyrolysis of Wood, Cellulose, and Lignin Determined by Differential Thermal Analysis. U.S. Forest Service Research FPL 82 Jan. 1968.

Tappi. Acid-insoluble lignin in wood and pulp. T 222 om-88, TAPPI 1988.

Thompson, et al. Comparison of Pretreatment Methods on the Basis of Available Surface Area. Bioresource Technology. 1992; 39:155-163.

Thring, et al. Recovery of a Solvolytic Lignin: Effects of Spent liquor/acid voulme ratio, acid concentration and temperature. Biomass. 1990; 23:289-305.

Timur, et al. Characterization and application of activated carbon produced from oak cups pulp. Journal of Analytical and Applied Pyrolysis. 2010; 89:129-136.

Unal, et al. Dechlorination of Bleached Kraft Pulp by Laccase Enzyme Produced from Some White-Rot Fungi. Turk J Biol. 2001; 25:67-72.

Van Dam. Characterization of Sulfur-free lignins from alkaline pulping of annual fibere crops. The international Lignin Institute, 5th international Forum' Sep. 7, 2000, Bordeaux (France).

Van Sprongsen, et al. Separation and recovery of the constituents from lignocellulosic biomass by using ionic liquids and acetic acid as co-solvents for mild hydrolysis. Chemical Engineering and Processing. 2011; 50:196-199.

Wang, et al. Influence of steaming explosion time on the physic-chemical properties of cellulose from *Lespedeza* stalks (*Lespedeza crytobotrya*). Bioresource Technology. 2009; 100:5288-5294.

Wang. Thermal Modification of Wood. Faculty of Forestry University of Toronto. 2011.

Wood, et al. Determination of Methanol and Its Application to Measurement of Pectin Ester Content and Pectin Methyl Esterase Activity. Analytical biochemistry. 1971; 39:418-428.

Wood-Ethanol Report. Environment Canada. 1999.

Wyman, et al. Comparative sugar recovery data from laboratory scale application of leading pretreatment technologies to corn stover. Bioresource Technology. 2005; 96: 2026-2032.

Wyman, et al. Coordinated development of leading biomass pretreatment technologies. Bioresource Technology. 2005; 96:1959-1966.

Xie, et al. Opportunities with Wood Dissolved in Ionic Liquids. In Cellulose Solvents: Foe Analysis, Shaping and Chemical Modification. Chapter 19. 2010;343-363.

Yang, et al. Pretreatment: the key to unlocking low-cost cellulosic ethanol. Biofuels, Bioprod. Bioref 2008; 2:26-40.

Ye, et al. Spontaneous High-Yield Production of Hydrogen from Cellulosic Materials and Water Catalyzed by Enzyme Cocktails. ChemSusChem. 2009; 2:149-152.

Yeoh, et al. Comparisons between different techniques for water-based extraction of pectin from orange peels. Desalination 2008; 218:229-237.

Yoshida, et al. Gasification of biomass model compounds and real biomass in supercritical water. Biomass and Bioenergy.2004; 26:71-78.

Zheng, et al. Overview of biomass pretreatment for cellulosic ethanol production. Int J Agric & Biol Eng. 2009; 2(3):51-68.

Zheng, et al. Supercritical carbon dioxide explosion as a pretreatment for cellulose hydrolysis. Biotechnology Letters. Aug. 1995; 17(8):845-850.

Zhu, et al. Understanding methanol formation in pulp mills. 1999 International Environmental Conference, pp. 139-143.

Zimbardi, et al. Acid impregnation and steam explosion of corn stover in batch processes. Industrial Crops and Productions. 2007; 26:195-206.

Zinoviev, et al. Background Paper on biofuels Production Technologies. International Centre for Science and High Technology and UNIDO. Nov. 2007; 1-106.

U.S. Appl. No. 61/558,374, filed Nov. 10, 2011, Baniel et al.

Eyal, et al. Extraction of Strong Mineral Acids by Organic Acid-Base Couples. Ind. Eng. Chem. Process Des. Dev. 1982, 21, 334-337.

Eyal, et al. pH dependence of carboxylicand mineral acid extraction by amine-based extractants: effects of pKa, Amine Basicity, and diluent properties. Ind. Eng. Chem. Res. 1995; 34:1789-1798.

International search report and written opinion dated Jun. 15, 2012 for PCT/US2011/064237.

Saadatmand, et al. Prehydrolysis in softwood pulping produces a valuable biorefinery fraction for material utilization. Environ. Sci. Technol. Jul. 7, 2012; DOI: 10.1021/es301699n.

* cited by examiner

METHODS AND SYSTEMS FOR PROCESSING LIGNOCELLULOSIC MATERIALS AND RELATED COMPOSITIONS

CROSS-REFERENCE

In accord with the provisions of 35 U.S.C. §119(a) and/or §365(b), this application claims priority to:

IL209912 entitled "A METHOD FOR TREATING A LIGNOCELLULOSIC FEED CONTAINING ASH AND FATTY ACID" to Aharon EYAL et al. filed on Dec. 9, 2010; and IL210161 entitled "A METHOD FOR PROCESSING A LIGNOCELLULOSIC MATERIAL INTO A HYDROLYZATE PRODUCT" to Aharon EYAL filed on Dec. 21, 2010; each of which is fully incorporated herein by reference.

In addition, in accord with the provisions of 35 U.S.C. §119(e) and §363, this application claims the benefit of the following U.S. Provisional Patent Applications:

U.S. 61/474,298 entitled "A METHOD FOR PREPARING A HYDROLYZATE" to Robert JANSEN et al. filed on Apr. 12, 2011;

U.S. 61/524,350 entitled "METHODS AND SYSTEMS FOR PROCESSING LIGNOCELLULOSIC MATERIALS" to Aharon EYAL et al. filed on Aug. 17, 2011; and U.S. 61/528,257 entitled "METHODS AND SYSTEMS FOR PROCESSING LIGNOCELLULOSIC MATERIALS" to Robert JANSEN et al. filed on Aug. 28, 2011.

U.S. 61/533,078 entitled "METHODS AND SYSTEMS FOR PROCESSING LIGNOCELLULOSIC MATERIALS" to Robert JANSEN et al. filed on Sep. 9, 2011;

U.S. 61/539,196 entitled "METHODS AND SYSTEMS FOR PROCESSING LIGNOCELLULOSIC MATERIALS" to Robert JANSEN et al. filed on Sep. 26, 2011;

U.S. 61/539,239 entitled "METHODS AND SYSTEMS FOR PROCESSING LIGNOCELLULOSIC MATERIALS" to Robert JANSEN et al. filed on Sep. 26, 2011;

U.S. 61/539,272 entitled "METHODS AND SYSTEMS FOR PROCESSING LIGNOCELLULOSIC MATERIALS" to Robert JANSEN et al. filed on Sep. 26, 2011;

U.S. 61/539,854 entitled "METHODS AND SYSTEMS FOR PROCESSING LIGNOCELLULOSIC MATERIALS" to Robert JANSEN et al. filed on Sep. 27, 2011;

U.S. 61/539,861 entitled "A METHOD FOR PROCESSING A LIGNOCELLULOSIC MATERIAL INTO A HYDROLYZATE PRODUCT" to Aharon EYAL filed on Sep. 27, 2011;

U.S. 61/552,402 entitled "LIGNIN COMPOSITIONS, METHODS OF PRODUCING THE COMPOSITIONS, METHODS OF USING LIGNIN, AND PRODUCTS PRODUCED THEREBY" to Robert JANSEN et al. filed on Oct. 27, 2011;

U.S. 61/559,529 entitled "LIGNIN COMPOSITIONS, METHODS OF PRODUCING THE COMPOSITIONS, METHODS OF USING LIGNIN, AND PRODUCTS PRODUCED THEREBY" to Robert JANSEN et al. filed on Nov. 14, 2011; and U.S. 61/562,931 entitled "Biomass treatment methods" to Aharon EYAL filed on Nov. 22, 2011; each of which is fully incorporated herein by reference.

In addition, this application is related to the following co-pending patent applications:

U.S. 61/483,777 entitled "HYDROLYSIS SYSTEMS AND METHODS" to Robert JANSEN et al. filed on May 9, 2011;

U.S. 61/487,319 entitled "HYDROLYSIS SYSTEMS AND METHODS" to Robert JANSEN et al. filed on May 18, 2011;

U.S. 61/491,243 entitled "LIGNIN COMPOSITIONS, SYSTEMS AND METHODS FOR PROCESSING LIGNIN AND/OR HCl" to Robert JANSEN et al. filed on May 30, 2011;

U.S. 61/500,169 entitled "SUGAR MIXTURES AND METHODS FOR PRODUCTION AND USE THEREOF" to Aharon EYAL et al. filed on Jun. 23, 2011;

U.S. 61/501,276 entitled "METHODS OF PROCESSING A SUCROSE CROP" to Aharon EYAL et al. filed on Jun. 27, 2011;

U.S. 61/539,272 entitled "METHODS AND SYSTEMS FOR PROCESSING LIGNOCELLULOSIC MATERIALS" to Robert JANSEN et al. filed on Sep. 26, 2011;

PCT application US2011/057552 "HYDROLYSIS SYSTEMS AND METHODS" to JANSEN et al. filed on Oct. 24, 2011; and U.S. 61/558,374 entitled "LIGNOCELLULOSE PROCESSING METHODS AND COMPOSITIONS RESULTING THEREFROM" to Eran BANIEL et al. filed on Nov. 10, 2011; each of which is fully incorporated herein by reference.

FIELD OF THE INVENTION

This invention relates to methods for processing of lignocellulosic materials including, but not limited to, wood and to resultant compositions.

BACKGROUND OF THE INVENTION

The carbohydrate-conversion industry is large. Currently, about 100 million tons of carbohydrates are fermented annually. Much of this fermentation produces fuel-grade ethanol.

Millions of tons of carbohydrates are also fermented every year to provide food and feed products, such as citric acid and lysine.

Fermentation of carbohydrates also produces other products, such as monomers for the polymer industry, e.g. lactic acid for the production of polylactide.

Carbohydrate conversion is an attractive and environmentally-friendly process since carbohydrates are a renewable resource. For example sucrose can be produced from sugar canes and glucose can be produced from corn and wheat starches. However, sugar cane, corn and wheat are produced primarily for human consumption and/or as livestock feed. Increased consumption by industry may impact food costs.

As an alternative, many renewable non-food resources are potential sources of carbohydrates. The renewable non-food resources can generally be described as "woody materials" or "lignocellulosic materials". These lignocellulosic materials include, but are not limited to, wood and by-products of wood processing (e.g. chips, sawdust, and shavings) as well as residual plant material from agricultural products and paper and paper industry byproducts (e.g. cellulose containing residues and/or paper pulp).

Residual plant material from agricultural products includes processing by-products and field remains.

Processing by-products include, but are not limited to, corn cobs, sugar cane bagasse, sugar beet pulp, empty fruit bunches from palm oil production, straw (e.g. wheat or rice), soy bean hulls, residual meals from the vegetable oil industry (e.g. soybean, peanut, corn or rapeseed), wheat bran and fermentation residue from the beer and wine industries.

Field remains include, but are not limited to, corn stover, post-harvest cotton plants, post-harvest soybean bushes and post-harvest rapeseed plants.

Lignocellulosic materials also include "energy crops" such as switch grass and broom grass which grow rapidly and generate low-cost biomass specifically as a source of carbohydrates.

These lignocellulosic carbohydrate sources contain cellulose, hemicellulose and lignin as their main components can also contain mineral salts (ashes) and lipophilic organic compounds, such as tall oils resin acids, fatty acids, triglycerides and other organic compounds, including volatile organic compounds such as turpentine. The degree and type of these non-carbohydrate materials can create technical problems in production of soluble carbohydrates.

SUMMARY OF THE INVENTION

A broad aspect of the invention relates to preparation of lignocellulosic material for additional downstream processing According to various exemplary embodiments of the invention the preparation includes removal of water and/or lipophilic impurities and/or ash which can contribute to ease of function of equipment used in the downstream processing. Alternatively or additionally, the preparation includes a thermo-mechanical treatment.

One aspect of some embodiments of the invention relates to improvement of a filtration rate of solid lignin from an acid hydrolyzate. In some embodiments, pretreatment of a lignocellulosic substrate with a water-soluble organic solvent, optionally including a weak acid, contributes to the improvement of the filtration rate. Alternatively or additionally, application of a predetermined pressure-temperature-time profile to the lignocellulosic substrate contributes to the improvement of the filtration rate.

One aspect of some embodiments of the invention relates to extraction of a lignocellulosic substrate with a water-soluble organic solvent, optionally in the presence of a weak acid, to produce extracted substrate and a liquid extract (miscella).

For example, a method of the invention comprises (a) providing a lignocellulosic substrate; (b) contacting said lignocellulosic substrate with an extractant comprising a water-soluble organic solvent to form an extracted substrate and a miscella; and (c) removing miscella from said extracted substrate. In some instances, the method further includes (d) hydrolyzing said extracted substrate using a chemically catalyzed process. In some instances, the method further includes hydrolyzing said extracted substrate to form a hydrolyzate and lignin solids; and (e) filtering said lignin solids from said hydrolyzate, wherein a filtration rate of said filtering is faster by at least 10% compared with a filtration rate of lignin solids from hydrolyzate formed by hydrolyzing said substrate without said extracting, using an identical filter and identical filtration conditions. In some instances, the method further includes enzymatically hydrolyzing said extracted substrate. In some instances, the method further includes subjecting said extracted substrate to a thermal process involving exposure to temperatures in excess of 200° C. In some instances, the method further includes subjecting said extracted substrate to a sulfite treatment process. In some instances, the method further includes hydrolyzing the extracted substrate to generate lignin solids and/or carbohydrate and further processing said lignin solids and/or carbohydrates to make a consumer product or commercial product.

One aspect of the invention comprises a method comprising: removing impurities from a lignocellulosic material and filtering lignin from said lignocellulosic material, wherein the step of removing impurities reduces rate of fouling of filter or increases rate of filtering by at least 20%.

Another aspect of the invention relates to a miscella derived from a lignocellulosic biomass subjected to a weak acid and organic solvent. A miscella or miscella layer as used herein can comprise a non-carbohydrate materials from lignocellulosic biomass, a weak acid, and an organic solvent.

Another aspect of the invention relates to a method for making a commercial product comprising: removing miscella comprising impurities from a lignocellulosic biomass; hydrolyzing said biomass to generate lignin or sugar; and using said lignin or sugar to make a commercial product.

Another aspect of some embodiments of the invention relates to application of a predetermined pressure-temperature-time profile to a lignocellulosic substrate. As used in this specification and the accompanying claims the term predetermined pressure-temperature-time profile includes any thermo-mechanical treatment. In some exemplary embodiments of the invention, application of a predetermined pressure-temperature-time profile can produce a disrupted substrate. Optionally, application of a predetermined pressure-temperature-time profile can be followed by extraction with a water-soluble organic solvent. According to various exemplary embodiments of the invention the predetermined pressure-temperature-time profile includes steam explosion and/or expeller treatment (e.g. using a plug screw feeder) and/or ammonia fiber explosion (AFEX). In some embodiments, the plug screw feeder treatment includes use of an impressafiner apparatus (Andritz; Graz, Austria). A description of AFEX is provided by Taherzade and Karimi (Int. J. Mol. Sci. (2008) 9: 1621-1651) which is fully incorporated herein by reference.

Exemplary predetermined pressure-temperature-time profiles are described in co-pending applications U.S. 61/552,402, U.S. 61/558,374 and U.S. 61/559,529; each of which is fully incorporated herein by reference.

In some embodiments of the invention, the predetermined-pressure-temperature-time profile is applied prior to contacting the disrupted substrate with extractant.

In exemplary embodiments in which steam explosion provides the predetermined-pressure-temperature-time profile, steam from the steam explosion can optionally be used to evaporate solvent from the extracted substrate.

In some embodiments of the invention, the solvent includes an alcohol and/or ketone with less than 5 carbon atoms. In some embodiments, the solvent includes acetone or acetone in combination with water.

In some embodiments of the invention, production of a disrupted substrate contributes to an ability of the solvent to penetrate into the substrate. In some embodiments, increasing penetration contributes to the efficiency of extraction of one or more materials in the substrate, and/or an increase in recovery of the applied solvent.

An additional aspect of some embodiments of the invention relates to removal of at least 50% of the ash from the lignocellulosic substrate. In some exemplary embodiments of the invention, the removed portion of the ash includes at least 40%, 50%, or 60% of the magnesium (Mg) and calcium (Ca) originally present in the substrate. Optionally, removal of ash in general and/or Ca and/or Mg contributes to a reduction in complications of downstream processing of the extracted substrate.

An additional aspect of some embodiments of the invention relates to removal of at least 50% of total lipophilic materials from the lignocellulosic substrate. Optionally, removal of lipophilic materials contributes to a reduction in complications of downstream processing of the extracted substrate.

According to exemplary embodiments of the invention, the downstream processing includes hydrolysis in the presence of a reactive fluid, such as a supercritical fluid, and/or hydrolysis in the presence of a mineral acid such as HCl and/or $H_2SO_4$ and/or pyrolysis and/or gasification.

An additional aspect of some embodiments of the invention relates to extraction with a water-soluble organic solvent, in the presence of a weak acid, to produce extracted substrate and miscella, removing the miscella, and subjecting the extracted substrate to hydrolysis and/or pyrolysis and/or gasification.

In some exemplary embodiments, hydrolysis is conducted in the presence of HCl and/or $H_2SO_4$ and/or a reactive fluid.

In some exemplary embodiments of the invention, the extraction is conducted at a temperature of less than about 60° C.

In some exemplary embodiments of the invention, the solvent includes an alcohol and/or ketone and/or aldehyde and/or ester with less than 5 carbon atoms. In some embodiments, the solvent includes acetone.

In some exemplary embodiments of the invention, the weak acid has a boiling point of 120° C. or less at atmospheric pressure.

In some exemplary embodiments, the weak acid includes sulfurous acid and/or acetic acid.

Alternatively or additionally, at least one of the weak acid and the solvent does not form an azeotrope with water.

Optionally, these characteristics of the acid and/or solvent contribute to an ease of removal of residual extractant from the extracted substrate.

In some exemplary embodiments, the weak acid hydrolyzes less than 10% of the cellulose in the substrate during the extraction process.

In some exemplary embodiments, the weak acid hydrolyzes less than 10% of the hemicellulose in the substrate during the extraction process.

In some exemplary embodiments, the method of the present invention includes two or more extraction stages, each of which may be characterized by a ratio between the weak acid and the solvent which is independent of the ratio of acid to solvent in the other extraction stages.

In some exemplary embodiments, the method of the present invention includes multi-stage counter-current contacting between the substrate and the extractant.

In some exemplary embodiments, the method of the present invention comprises performing an additional extraction with a second extractant including a water-soluble organic solvent.

In some exemplary embodiments, the extractant comprises a water-soluble organic solvent and an alkali.

In some exemplary embodiments, the miscella is removed by draining and/or active removal.

In some exemplary embodiments, the lignocellulosic substrate is wood.

In some exemplary embodiments, the lignocellulosic substrate is harvested at least 5 days before extracting.

Another additional aspect of some embodiments of the invention relates to fractionation of the miscella, optionally by step-wise removal of solvent, to recover extracted materials.

According to various exemplary embodiments of the invention the extracted materials include one or more lipophilic components, such as oils, resins and resinic acids. In some embodiments, the fractionation is based upon a degree of hydrophobicity. In some exemplary embodiments of the invention, the extracted components have an economic value of their own which can be used to at least partially offset process costs. Alternatively or additionally, fractionation of the miscella to recover extracted materials contributes to recovery and/or re-use of the solvent and/or the weak acid as described in the previous aspect.

In some exemplary embodiments, the solvent and/or the weak acid are recovered from the miscella. Optionally, this recovery contributes to a reduction in process costs.

In some exemplary embodiments of the invention, recovery includes separating the solvent and/or weak acid from miscella. In some exemplary embodiments, separation includes distilling the miscella to form a solvent phase, an aqueous phase and a lipophilic fraction.

In some embodiments, the solvent phase includes the solvent and a portion of weak acid.

In some exemplary embodiments, separation includes fractionation of the lipophilic phase.

In some exemplary embodiments, the aqueous phase is subjected to anaerobic treatment to produce methane.

Yet another additional aspect of some embodiments of the invention relates to use of water-soluble hydrocarbons from the miscella. In some exemplary embodiments of the invention, these water-soluble hydrocarbons are used to produce methane. Optionally, the methane is produced in an anaerobic digester.

Yet another additional aspect of some embodiments of the invention relates to a system for processing lignocellulosic material which includes an extraction module adapted to extract the lignocellulosic material prior to hydrolysis in a hydrolysis module.

In some embodiments, the system includes a dryer for removing residual extractant. In some exemplary embodiments of the invention, the hydrolysis module employs a concentrated acid stream, for example, a concentrated HCl stream.

According to various exemplary embodiments of the invention the concentrated HCl stream includes 35%, 37%, 40%, 42% or 43% HCl or intermediate or greater percentages expressed as (HCl/(HCl+water)).

An additional aspect of some embodiments of the invention relates to a system comprising a distillation column for separating impurities from the miscella and recycling said miscella on the one hand and for forming a lipophilic fraction stream and a hydrocarbon-containing aqueous phase on the other hand.

Various exemplary embodiments of the invention relate to methods for processing an extracted substrate as described above to produce a sugar mixture. In some embodiments, the sugar mixture can then be converted to a conversion product using one or more additional processes.

Various exemplary embodiments of the invention relate to methods for converting at least a portion of an extracted substrate as described above to a conversion product. Optionally, conversion does not involve an intermediate sugar stage.

An additional aspect of some embodiments of the invention relates to extracted pine wood. In some exemplary embodiments of the invention, the extracted wood comprises at least 35% cellulose; at least 7.4% hemicellulose; and less than 0.7% ash, on a dry weight basis. Optimally, the extracted wood comprises less than 2% dichloromethane (DCM) extractives. Alternatively or additionally, the extracted wood optionally comprises less than 50%, less than 30%, less than 20% or less than 10% of the moisture content of the pine wood on an absolute basis prior to extraction. In some embodiments, at least 10% of the cells in the extracted wood are disrupted. In some embodiments, the extracted wood includes acetone.

In some embodiments, wood includes about 50% water. In some embodiments, the substrate includes about 60% water after a thermo mechanical treatment. Alternatively or additionally, the same substrate includes about 13-16% water after extraction.

An additional aspect of some embodiments of the invention relates to an extraction mixture. In some exemplary embodiments of the invention, the mixture comprises one part lignocellulosic substrate and at least 2 parts acetone, on a weight basis. Optionally, the extraction mixture includes less than 3 parts acetone.

According to various exemplary embodiments of the invention, the extraction mixture includes a weak acid, for example acetic acid and/or sulfurous acid. Optionally, the extraction mixture includes added water.

Exemplary downstream uses include, but are not limited to; acid hydrolysis to produce soluble sugars and/or lignin and production of paper from the lignocellulosic material.

In some exemplary embodiments of the invention, there is provided a lignocellulosic composition including (on a dry matter basis) cellulose, hemicellulose, lignin and characterized by at least one characteristic selected from the group consisting of:
  less than 5,000 PPM, optionally less than 3,000 PPM, optionally less than 2,000 PPM, optionally less than 1,000 PPM, optionally less than 500 PPM lipophilic material;
  less than 5,000 PPM, optionally less than 3,000 PPM, optionally less than 2,000 PPM, optionally less than 1,000 PPM, optionally less than 500 PPM ash;
  less than 2,000 PPM, optionally less than 1,500 PPM, optionally less than 1,000 PPM, optionally less than 500 PPM Ca;
  less than 10,000 PPM, optionally less than 8,000 PPM, optionally less than 6,000 PPM, optionally less than 4,000 PPM, optionally less than 2,000 PPM, optionally less than 1,000 pectin;
  less than 2,000 PPM, optionally less than 1,500 PPM, optionally less than 1,000 PPM, optionally less than 500 PPM furfural;
  at least 10 PPM of a marker selected from the group consisting of furfural, organically bound sulfur and water soluble solvent (e.g. acetone); and
  a moisture content of 5% to 30%, optionally 8% to 25%, optionally 10% to 20%.

In some embodiments, the composition is characterized by at least two, optionally at least three, optionally at least four, optionally at least 5 characteristics selected from the above group.

In some exemplary embodiments of the invention, there is provided a method including: (a) providing a lignocellulosic substrate; (b) contacting the lignocellulosic substrate with an extractant comprising a water-soluble organic solvent to form an extracted substrate and a miscella; (c) removing miscella from the extracted substrate (d) hydrolyzing the extracted substrate to form a hydrolyzate and lignin solids; and (e) filtering the lignin solids from the hydrolyzate; wherein a filtration rate of the filtering is faster by at least 10% compared with a filtration rate of lignin solids from hydrolyzate formed by hydrolyzing the substrate without the extracting, using an identical filter and identical filtration conditions.

In some exemplary embodiments of the invention, there is provided a method including: (a) providing a lignocellulosic substrate; (b) contacting the lignocellulosic substrate with an extractant comprising a water-soluble organic solvent to form an extracted substrate and a miscella; (c) removing miscella from the extracted substrate; and (d) hydrolyzing the extracted substrate using a chemically catalyzed process.

In some embodiments, the hydrolyzing employs a mineral acid as a catalyst.

In some embodiments, the mineral acid includes HCl.

In some embodiments, the mineral acid includes $H_2SO_4$.

In some embodiments, the hydrolyzing employs reactive fluid as a catalyst.

In some exemplary embodiments of the invention, there is provided a method including: (a) providing a lignocellulosic substrate; (b) contacting the lignocellulosic substrate with an extractant comprising a water-soluble organic solvent to form an extracted substrate and a miscella; (c) removing miscella from the extracted substrate; and (d) enzymatically hydrolyzing the extracted substrate.

In some embodiments, the method includes subjecting the extracted substrate to a sulfite process.

In some exemplary embodiments of the invention, there is provided a method including: (a) providing a lignocellulosic substrate; (b) contacting the lignocellulosic substrate with an extractant comprising a water-soluble organic solvent to form an extracted substrate and a miscella; (c) removing miscella from the extracted substrate; and (d) subjecting the extracted substrate to a thermal process involving exposure to temperatures in excess of 200° C.

In some embodiments, the thermal process includes pyrolysis.

In some embodiments, the thermal process includes gasification.

In some exemplary embodiments of the invention, there is provided a method including: (a) providing a lignocellulosic substrate; (b) contacting the lignocellulosic substrate with an extractant comprising a water-soluble organic solvent to form an extracted substrate and a miscella; (c) removing miscella from the extracted substrate; and (d) subjecting the extracted substrate to a sulfite process.

In some exemplary embodiments of the invention, there is provided a substrate processing method, the method including: (a) contacting a lignocellulosic substrate with a first extractant including a water-soluble organic solvent and a weak acid to form an extracted substrate and a miscella; (b) removing at least a portion of the miscella from the extracted substrate; and (c) hydrolyzing the extracted substrate with a strong acid to produce a hydrolyzate containing soluble sugars.

In some exemplary embodiments of the invention, there is provided a method comprising applying a predetermined pressure-temperature-time profile to a lignocellulosic substrate (b) contacting the substrate with an extractant comprising a water-soluble organic solvent and a weak acid to form an extracted substrate and a miscella; and (c) processing the extracted substrate.

In some embodiments, applying the predetermined pressure-temperature-time profile disrupts the substrate.

In some exemplary embodiments of the invention, there is provided a method including:
  (a) providing a lignocellulosic substrate;
  (b) contacting said lignocellulosic substrate with an extractant comprising a water-soluble organic solvent to form an extracted substrate;
  (c) hydrolyzing said extracted substrate to form a hydrolyzate and a lignin solids; and
  (d) filtering said lignin solids from said hydrolyzate,
  wherein a filtration rate of said filtering is faster by at least 10% compared with a filtration rate of lignin solids from hydrolyzate formed by hydrolyzing said substrate without said extracting, using an identical filter and identical filtration conditions.

Optionally, the extracting forms a miscella, and the method includes removing at least a portion of the miscella from the extracted substrate.

Optionally, the water-soluble organic solvent includes at least one solvent selected from the group consisting of ketones, aldehydes, esters and alcohols with up to four carbon atoms.

Optionally, the water-soluble organic solvent includes acetone.

Optionally, the methods include applying of a predetermined-pressure-temperature-time profile prior to contacting the substrate with the extractant.

In some exemplary embodiments, processing of the extracted substrate includes hydrolysis in the presence of a reactive fluid to produce soluble sugars.

In some exemplary embodiments, processing of the extracted substrate includes hydrolysis in the presence of a mineral acid to produce soluble sugars. Optionally, the mineral acid comprises at least one of hydrochloric acid and sulfuric acid.

In some exemplary embodiments, processing of the extracted substrate includes enzymatic hydrolysis to produce soluble sugars.

In some exemplary embodiments, processing of the extracted substrate includes pyrolysis.

In some exemplary embodiments, processing of the extracted disrupted substrate includes gasification.

In some exemplary embodiments, the predetermined pressure-temperature-time profile comprises a steam explosion treatment. Optionally, the steam explosion treatment comprises application of steam at a desired pressure and temperature for a time period in the range of from about 10 seconds to about 5 minutes, optionally from about 30 seconds to about 3 minutes. In some exemplary embodiments of the invention, the desired pressure can be in the range of from about 6 atm to about 45 atm. Application of steam under pressure is followed by rapid venting of pressure. Optionally, steam is applied at a temperature in the range of from about 170° C. to about 230° C., optionally about 190° C. to about 210° C. Optionally, steam from the steam explosion treatment is used to evaporate solvent from the extracted substrate.

In some exemplary embodiments, extracting is conducted at a temperature of less than 70° C., optionally less than 60° C.

In some exemplary embodiments, extracting is conducted at an ambient pressure.

In some exemplary embodiments, the predetermined pressure-temperature-time profile comprises an ammonia explosion treatment.

In some exemplary embodiments, the predetermined pressure-temperature-time profile comprises treatment with a plug screw feeder.

Optionally, the extractant includes a weak acid.

Optionally, the weak acid is selected from the group consisting of sulfurous acid and acetic acid.

Optionally, the weak acid in the extractant hydrolyzes less than 10% of cellulose in the substrate during said extracting until said removing.

Optionally, the weak acid in said extractant hydrolyzes less than 10% of hemicellulose in the substrate during the extracting and until the removing.

Optionally, the extracting is conducted at a temperature of less than 70° C.

Optionally, the extracting is conducted at an ambient pressure.

Optionally, the extracted substrate contains less than 50%; optionally less than 40%; optionally less than 35%; optionally less than 25% of the water provided in said lignocellulosic substrate.

Optionally, the extracted substrate contains less than 50% of the ash content provided in said lignocellulosic substrate.

Optionally, the extracted substrate contains less than 50% of the Mg+Ca content provided in said lignocellulosic substrate.

Optionally, the extracted substrate contains less than 50% of the lipophilic materials provided in said lignocellulosic substrate.

In some exemplary embodiments of the invention, there is provided a method comprising contacting a lignocellulosic substrate with an extractant comprising a water-soluble organic solvent to form an extracted substrate and a miscella; (b) removing miscella from the extracted substrate; and (c) hydrolyzing the extracted substrate using a mineral acid as a catalyst.

Optionally, the mineral acid comprises hydrochloric acid.

Optionally, the mineral acid comprises sulfuric acid.

In some exemplary embodiments of the invention, there is provided a method comprising (a) contacting a lignocellulosic substrate with an extractant comprising a water-soluble organic solvent to form an extracted substrate and a miscella; (b) removing miscella from the extracted substrate; and (c) pyrolyzing the extracted substrate.

In some exemplary embodiments of the invention, there is provided a method comprising (a) contacting a lignocellulosic substrate with an extractant comprising a water-soluble organic solvent to form an extracted substrate and a miscella; (b) removing miscella from the extracted substrate; and (c) gasifying the extracted substrate.

In some exemplary embodiments of the invention, there is provided a method comprising; (a) contacting a lignocellulosic substrate with an extractant comprising a water-soluble organic solvent to form an extracted substrate and a miscella; (b) removing miscella from the extracted substrate; and (c) hydrolyzing the extracted substrate in the presence of a reactive fluid.

In some exemplary embodiments, subsequent to removal of the miscella from the extracted substrate, the substrate is subjected to a sulfite process.

Optionally, the extractant comprises a weak acid.

Optionally, the method comprises applying a predetermined pressure-temperature-time profile to said lignocellulosic substrate. In some embodiments, applying a predetermined pressure-temperature-time profile disrupts cellular structures in the substrate. Optionally, removing of miseclla includes draining.

Optionally, removing includes active removal.

Optionally, the method includes harvesting a lignocellulosic substrate and allowing at least 5 days between harvesting and contacting.

Optionally, the lignocellulosic substrate is wood.

Optionally, less than 10% of cellulose in said lignocellulosic substrate hydrolyzes before said removing.

Optionally, less than 10% of hemicellulose in said lignocellulosic substrate hydrolyzes before said removing.

Optionally, the water-soluble organic solvent includes at least one solvent selected from the group consisting of ketones, aldehydes, esters and alcohols with up to four carbon atoms.

Optionally, the water-soluble organic solvent includes acetone.

Optionally, the extractant comprises a weak acid.

Optionally, the weak acid includes at least one acid selected from the group consisting of sulfurous acid and acetic acid. Optionally, the weak acid has a boiling point lower than 120° C. at atmospheric pressure.

Optionally, at least one of the weak acid and the solvent does not form an azeotrope with water.

Optionally, the contacting includes two or more extraction stages and each of the two or more extraction stages is characterized by a ratio between the weak acid and the solvent in the extractant independent of a same ratio in one or more other extraction stages of the two or more extraction stages.

Optionally, the extraction includes multi-stage counter-current contacting between the substrate and the extractant.

Optionally, the first extractant includes water, wherein the extraction includes two or more extraction stages and wherein each of the two or more extraction stages is characterized by a ratio between the water and the solvent in the extractant independent of a same ratio in one or more other extraction stages of the two or more extraction stages.

Optionally, a ratio between the water-soluble organic solvent in the first extractant and water in the substrate is at least 2.0 on a weight basis.

Optionally, the method includes separating at least a portion of at least one of the water-soluble organic solvent and the weak acid from the miscella.

Optionally, the method includes distilling the miscella to produce a solvent phase, an aqueous phase and a lipophilic fraction. Optionally, steam generated by the predetermined pressure-temperature-time profile is applied to the lipophilic fraction to recover solvent therefrom.

Optionally, the solvent phase includes the water-soluble organic solvent and at least a portion of the weak acid.

Optionally, the method includes fractionation of the lipophilic fraction of the miscella.

Optionally, the method includes using steam generated by said predetermined pressure-temperature-time profile to evaporate said solvent from said miscella.

Optionally, the method includes anaerobic treatment of the aqueous phase to produce methane.

Optionally, the extracted substrate contains less than 50%; optionally less than 40%; optionally less than 30%; optionally less than 25%, optionally less than 20%, optionally less than 18% of the water provided in the lignocellulosic substrate.

Optionally, the extracted substrate contains less than 50% of the ash content provided in the lignocellulosic substrate.

Optionally, the extracted substrate contains less than 50% of the Mg+Ca content provided in the lignocellulosic substrate.

Optionally, the extracted substrate contains less than 50% of the lipophilic materials originally provided in the lignocellulosic substrate.

Optionally, the method includes performing an additional extraction with a second extractant including the water-soluble organic solvent.

Optionally, the hydrolyzing includes acid hydrolysis in an aqueous medium including at least 35%; HCl:(HCl+water) W/W.

Optionally, the method includes an alkaline treatment of at least one of the substrate and the extracted substrate to form a lipophilic fraction depleted substrate and a solution including an alkali salt of fatty acid.

Optionally, the extractant includes the water-soluble organic solvent and an alkali.

Optionally, the method includes separating miscella from the extracted substrate.

Optionally, the predetermined pressure-temperature-time profile comprises a steam explosion treatment.

Optionally, the predetermined pressure-temperature-time profile includes application of a pressure in the range of from about 6 atm to about 45 atm for a time period in the range of from about 10 seconds to about 5 minutes, optionally from about 30 seconds to about 3 minutes (measure time at the target pressure/temperature).

Optionally, the contacting is conducted at a temperature of less than 60° C.

Optionally, the predetermined pressure-temperature-time profile comprises an ammonia explosion treatment.

Optionally, the predetermined pressure-temperature-time profile comprises treatment with a plug screw feeder.

Optionally, the weak acid is selected from the group consisting of sulfurous acid and acetic acid.

In some exemplary embodiments of the invention, there is provided a method including: (a) contacting a lignocellulosic substrate with an extractant comprising a water-soluble organic solvent to form an extracted substrate and a miscella; (b) removing miscella from the extracted substrate; (c) subjecting the extracted substrate to a sulfite process; and (d) enzymatically hydrolyzing the extracted substrate.

In some exemplary embodiments of the invention, there is provided a method including: (a) providing a hydrolyzate containing soluble sugars as described above; and (b) converting at least a portion of the sugars to a conversion product.

In some exemplary embodiments of the invention, there is provided a method including: (a) providing an extracted substrate as described above; and (b) converting at least a portion of said substrate to a conversion product.

Optionally, the converting of the sugars includes a process selected from the group consisting of fermentation, chemical conversion, enzymatic conversion, electrolytic reduction, catalytic hydrogenation, and isomerization.

Optionally, the converting of the extracted substrate includes a process selected from the group consisting of pyrolysis, gasification, aqueous phase re-forming, hydrolysis, hydrogenolysis, chemical conversion, enzymatic conversion, electrolytic reduction, catalytic hydrogenation, and isomerization.

Optionally, the fermentation includes anaerobic fermentation.

Optionally, the conversion product includes at least one member selected from the group consisting of alcohols, carboxylic acids, amino acids, monomers for the polymer industry, yeast, methane and proteins.

Optionally, the method includes processing the conversion product to produce a consumer product selected from the group consisting of detergent, polyethylene-based products, polypropylene-based products, polyolefin-based products, polylactic acid (polylactide)-based products, polyhydroxyalkanoate-based products and polyacrylic-based products.

Optionally, the detergent includes a sugar-based surfactant, a fatty acid-based surfactant, a fatty alcohol-based surfactant, or a cell-culture derived enzyme.

Optionally, the polyacrylic-based product is selected from plastics, floor polishes, carpets, paints, coatings, adhesives, dispersions, flocculants, elastomers, acrylic glass, absorbent articles, incontinence pads, sanitary napkins, feminine hygiene products, and diapers.

Optionally, the polyolefin-based products are selected from milk jugs, detergent bottles, margarine tubs, garbage containers, water pipes, absorbent articles, diapers, non wovens, HDPE toys and HDPE detergent packaging.

Optionally, the polypropylene based products are selected from absorbent articles, diapers and non wovens.

Optionally, the polylactic acid based products are selected from packaging of agriculture products and of dairy products, plastic bottles, biodegradable products and disposables.

Optionally, the polyhydroxyalkanoate based products are selected from packaging of agriculture products, plastic bottles, coated papers, molded or extruded articles, feminine hygiene products, tampon applicators, absorbent articles, disposable nonwovens and wipes, medical surgical garments, adhesives, elastomers, films, coatings, aqueous dispersants, fibers, intermediates of pharmaceuticals and binders.

Optionally, the conversion product includes at least one member of the group consisting of methane, ethanol, butanol, isobutanol, a fatty acid, a fatty acid ester, a fatty alcohol and biodiesel.

Optionally, the method includes processing of the conversion product to produce at least one product selected from the group consisting of an isobutene condensation product, jet fuel, gasoline, gasohol, diesel fuel, drop-in fuel, diesel fuel additive, and a precursor thereof.

Optionally, the gasohol is ethanol-enriched gasoline or butanol-enriched gasoline.

Optionally, the product is selected from the group consisting of diesel fuel, gasoline, jet fuel and drop-in fuels.

In some exemplary embodiments of the invention, there is provided a consumer product, a precursor of a consumer product, or an ingredient of a consumer product produced from a conversion product as described above.

Optionally, the consumer product, precursor of a consumer product, or ingredient of a consumer product includes at least one conversion product produced by a method described above, wherein the fermentation product is selected from carboxylic and fatty acids, dicarboxylic acids, hydroxylcarboxylic acids, hydroxyl di-carboxylic acids, hydroxyl-fatty acids, methylglyoxal, mono-, di-, or poly-alcohols, alkanes, alkenes, aromatics, aldehydes, ketones, esters, biopolymers, proteins, peptides, amino acids, vitamins, antibiotics, and pharmaceuticals.

Optionally, the product is ethanol-enriched gasoline, jet fuel, or biodiesel.

Optionally, the consumer product, precursor of a consumer product, or ingredient of a consumer product has a ratio of carbon-14 to carbon-12 of about $2.0 \times 10^{-13}$ or greater.

In some exemplary embodiments of the invention, the consumer product includes an ingredient as described above and an additional ingredient produced from a raw material other than lignocellulosic material.

Optionally, the ingredient and the additional ingredient produced from a raw material other than lignocellulosic material are essentially of the same chemical composition.

Optionally, the consumer product includes a marker molecule at a concentration of at least 100 ppb.

Optionally, the marker molecule is selected from the group consisting of furfural, hydroxy-methyl furfural, products of furfural or hydroxy-methylfurfural condensation, color compounds derived from sugar caramelization, levulinic acid, acetic acid, methanol, galacturonic acid, and glycerol.

In some exemplary embodiments of the invention, there is provided a system including:

(a) an extraction module adapted to extract a lignocellulosic substrate with an extractant including a water-soluble organic solvent and a weak acid, and to output an extracted substrate and an impurity rich extract; (b) a hydrolysis module adapted to receive the extracted substrate and to contact it with hydrochloric acid at a concentration of at least 30% to produce an acid hydrolyzate.

Optionally, the extraction module delivers an extractant formulated to extract at least 30%; optionally at least 40%; optionally 50% or more of ash present in said substrate.

Optionally, the system includes a dryer adapted to remove extractant from the extracted substrate;

Optionally, the system includes a disruption module adapted to apply a predetermined pressure-temperature-time profile to the substrate.

Optionally, the disruption module includes at least one item selected from the group consisting of a plug screw feeder and an explosion reactor (e.g. steam explosion or ammonia explosion).

Optionally, the system includes a distillation column adapted to obtain the impurity rich extract and return at least a portion of the solvent to the extraction module.

Optionally, the system includes a methane generator adapted to obtain the hydrocarbon including an aqueous phase.

In some exemplary embodiments of the invention, there is provided an extracted lignocellulose composition including (on a dry weight basis): (a) at least 35% cellulose; (b) at least 7.4% hemicellulose; and (c) less than 0.7% ash.

Optionally, the composition includes less than 2% DCM (dichloromethane) extractives.

Optionally, the composition includes less than 50% of the moisture content of the pine wood prior to extraction.

Optionally, at least 10% of the cells are disrupted.

Optionally, the composition includes acetone.

Optionally, the lignocellulose includes pine wood.

Optionally, the composition includes at least 0.01%, optionally 0.005% by weight, of an acid selected from the group consisting of sulfurous acid, acetic acid and carbonic acid.

In some exemplary embodiments of the invention, there is provided an extraction mixture including (on a weight basis): (a) one part lignocellulosic substrate; and (b) at least 2 parts acetone.

Optionally, the mixture includes less than 3 parts acetone.

Optionally, the mixture includes a weak acid.

Optionally, the weak acid includes at least one of acetic acid, sulfurous acid and carbonic acid.

Optionally, the mixture includes added water.

In some embodiments, there is provided a method for processing a lignocellulosic material into a hydrolyzate product, a primary lignin product and optionally a secondary lignin product, comprising: (a) providing a lignocellulosic feed material comprising at least one insoluble polysaccharide and lignin; (b) hydrolyzing a fraction of said insoluble polysaccharide in an HCl-comprising hydrolysis medium to form a hydrolyzate, which hydrolyzate comprises at least one carbohydrate and HCl, and a lignin stream comprising solid lignin, HCl and water, (c) separating said hydrolyzate from said lignin stream to form a separated hydrolyzate and a separated lignin stream, (d) de-acidifying said separated hydrolyzate to form a de-acidified, carbohydrate-comprising hydrolyzate; (e) processing said de-acidified carbohydrate-comprising hydrolyzate into at least one hydrolyzate product; (f) de-acidifying said separated lignin stream to form de-acidified lignin; (g) treating said de-acidified lignin at an elevated temperature, in an oxygen-deficient atmosphere to form at least one primary lignin product and optionally converting said primary lignin product to form at least one secondary lignin product and excess heat, (h) optionally treating at least one of said hydrolyzate product, said primary lignin product, and said secondary lignin product and (i) using said excess heat in at least one of steps (a) to (f) and (h).

According to various exemplary embodiments of the invention any lignocellulosic material is used in the method. For example, the material can include one or more of wood, sugarcane bagasse, palm oil biomass, other agriculture residues and energy crops.

The provided lignocellulosic material comprises at least one insoluble polysaccharide. As used herein, the term insoluble means water-insoluble. According to an embodiment, the insoluble polysaccharide is selected from the group consisting of hemicellulose, amorphous cellulose and crystalline cellulose. In some embodiments the lignocellulosic feed material comprises two or three of those polysaccharides.

Hydrolyzing a fraction of said insoluble polysaccharide in an HCl-comprising hydrolysis medium comprises contacting said lignocellulosic feed material with a hydrolysis medium. Exemplary forms of contacting are described in, for example, co-pending application PCT/US11/57552; which is fully incorporated herein by reference.

In some embodiments, in said HCl-comprising hydrolysis medium the weight ratio between HCl and (HCl+water) is in the range between 0.25 and 0.50, between 0.30 and 0.45 or between 0.35 and 0.40.

In some embodiments, the ratio between the weight of soluble carbohydrates in the hydrolyzate and the weight of the soluble carbohydrates combined with the weight of water is between 0.15 and 0.40.

The hydrolysis also forms a lignin stream comprising solid lignin, HCl and water. In some embodiments, the solid lignin constitutes the majority of the lignin stream, while according to another embodiment, solid lignin is dispersed in the lignin stream. Typically the solid lignin is swelled with an HCl aqueous solution. The lignin stream may contain, according to various embodiments, additional compounds, such as carbohydrates and polysaccharides. In some embodiments, the lignin stream comprises solid lignin as well as an insoluble polysaccharide. Optionally, the insoluble polysaccharide is a residual polysaccharide from the insoluble polysaccharide in the lignocellulosic material. According to an embodiment, said residual insoluble polysaccharides correspond to at least 5% of the insoluble polysaccharide in the lignocellulosic material. According to an embodiment, at least 50%, at least 70% or even at least 90% of the residual insoluble polysaccharide is crystalline.

In some exemplary embodiments of the invention, the method includes separating the hydrolyzate from the lignin stream to form separated hydrolyzate and separated lignin stream, de-acidifying the separated hydrolyzate and de-acidifying the separated lignin stream. Any form of separation and of deacidification is suitable. In some embodiments, de-acidifying of the hydrolyzate, de-acidifying of the lignin stream or both comprise contacting with an organic solvent.

Optionally, the organic solvent is selected from the group consisting of aliphatic or aromatic alcohols, ketones and aldehydes having at least 5 carbon atoms, e.g. various pentanols, hexanols, heptanols, octanols, nonanols, decanols, methyl-isobutyl-ketone and methyl-butyl-ketone and combinations thereof. As used here, the term alcohols means any of mono-, di- and poly-alcohols, primary, secondary and tertiary ones, straight-chain and branched-chain alcohols and any combination thereof. According to a preferred embodiment, the solvent is selected from hexanol and 2-ethyl-1-hexanol and a mixture thereof.

Alternatively or additionally, de-acidifying of the hydrolyzate includes chromatographic separation.

Additional details of exemplary methods to de-acidify the hydrolyzate can be found in co-pending applications IL 211093 and U.S. 61/524,839; PCT/IL2011/000424 and PCT/IL2011/000304; the teachings of which are incorporated herein by reference.

De-acidifying the hydrolyzate forms a de-acidified, carbohydrate-containing hydrolyzate. According to an embodiment, said de-acidified, carbohydrate-containing hydrolyzate is characterized by a hydrochloric acid to carbohydrates weight ratio of less than 0.01, less than 0.005 or even less than 0.002.

In some exemplary embodiments of the invention, the method includes processing the de-acidified carbohydrate-containing hydrolyzate into at least one hydrolyzate product. According to various exemplary embodiments of the invention this processing includes at least one of polishing, oligomer hydrolysis, chemically catalyzed conversion and bio-catalyzed conversion. Optionally, the processing includes fermenting carbohydrates in said de-acidified carbohydrate-containing hydrolyzate. According to various exemplary embodiments of the invention the hydrolyzate product is selected from the group consisting of ethanol, butanol, other alcohols, amino acids, carboxylic acids and monomers for the polymer industry.

Alternatively or additionally, in some embodiments, de-acidifying the lignin stream is conducted as described in co-pending application PCT/IL2011/000424 and PCT/IL2011/000304; each of which is fully incorporated herein by reference.

De-acidifying the lignin stream forms de-acidified lignin. Optionally, the de-acidified lignin is characterized by a hydrochloric acid to carbohydrates weight ratio of less than 0.01, less than 0.005 or even less than 0.002.

According to various exemplary embodiments of the invention forming of de-acidified lignin includes at least one of separation of solid lignin from an aqueous medium, separation of solid lignin from a solvent medium and drying of solid lignin. In some embodiments, the de-acidified lignin is a solid composition including mainly lignin. Optionally, the solid includes residual polysaccharide.

In some exemplary embodiments of the invention, the method includes treating the de-acidified lignin at an elevated temperature, in an oxygen-deficient atmosphere to form at least one primary lignin product. Optionally, the method includes converting the primary lignin product to form at least one secondary lignin product and excess heat. In some embodiments, the treating includes at least one of pyrolysis and gasification. Alternatively or additionally, the primary lignin product is selected from the group consisting of biocrude, hydrogen, carbon mono-oxide and carbon dioxide.

In some embodiments, the method includes converting the primary lignin product into a secondary lignin product. As used in this specification and the accompanying claims the term "secondary lignin product" indicates a product formed by converting a primary lignin product. According to various exemplary embodiments of the invention this converting includes at least one of chemically catalyzed conversion and biocatalyzed conversion. In some embodiments, biocatalyzed conversion includes fermentation of the primary lignin product.

According to various exemplary embodiments of the invention the secondary lignin product is selected from the group consisting of ethanol, butanol, other alcohols, amino acids, carboxylic acids and monomers for the polymer industry.

In some embodiments, the carbon contents of the lignocellulosic material, of the de-acidified carbohydrate-comprising hydrolyzate and of the at least one primary lignin product are M1, M2 and M3, respectively, and (M2+M3)/M1 is greater than 0.85, greater than 0.90 or even greater than 0.95.

In some embodiments, lignocellulosic material comprises extractives and the de-acidified lignin includes at least 50% of the said extractives.

In some embodiments, the method includes extracting the lignocellulosic material. In some embodiments, the extracting includes contacting with an organic solvent. In some embodiments, the organic solvent includes acetone.

According to various embodiments, the thermal treatment is conducted at a temperature in the range between 350° C. and 1,000° C. Alternatively or additionally, the thermal treatment is conducted at a pressure above 10 MPa, above 30 MPa and or even above 50 MPa. Alternatively or additionally, the thermal treatment is conducted in an atmosphere comprising less than 5% volume of oxygen, less than 3% volume of oxygen, or even less than 1% volume of oxygen.

In some embodiments, the method includes combining at least a fraction of the de-acidified, carbohydrate-comprising hydrolyzate with at least a fraction of the at least one primary lignin product to form a mixture and processing at least one of said carbohydrate hydrolyzate and said primary lignin product in said mixture.

In some embodiments, the method further includes reacting the hydrolyzate product with at least one of the primary lignin product and the secondary lignin product.

In some embodiments, the processing of carbohydrate hydrolyzate generates a carbon-containing co-product, and the method further includes combining the co-product with the de-acidified lignin stream to form a combined product, which combined product is then thermally treated.

A broad aspect of the invention relates to hydrolysis of biomass.

One aspect of some embodiments of the invention relates to supercritical, near-critical, or sub-critical fluids to pre-treat and/or hydrolyze the biomass.

In some exemplary embodiments of the invention, the supercritical, near-critical, or sub-critical fluids include water and at least one of $SO_2$ and a solvent. In some embodiments, the solvent is water-miscible and does not form an azeotrope with water.

In some exemplary embodiments of the invention, there is provided a method for the continuous treatment of biomass comprising: a pretreatment step, wherein the biomass is contacted with a first supercritical, near-critical, or sub-critical fluid to form a solid matrix and a first liquid fraction; wherein the first supercritical or near-critical fluid comprises water and at least one of $SO_2$ and a solvent; and wherein the solvent is water-miscible and does not form an azeotrope with water; and a hydrolysis step, wherein the solid matrix is contacted with a second supercritical or near-critical fluid to produce a second liquid fraction and an insoluble lignin-containing fraction.

In some exemplary embodiments of the invention, there is provided a method for the continuous treatment of biomass comprising: a pretreatment step, wherein the biomass is contacted with a first supercritical, near-critical, or sub-critical fluid to form a solid matrix and a first liquid fraction; and a hydrolysis step, wherein the solid matrix is contacted with a second supercritical or near-critical fluid to produce a second liquid fraction and an insoluble lignin-containing fraction; wherein the second supercritical or near-critical fluid comprises water and at least one of $SO_2$ and a solvent; and wherein the solvent is water-miscible and does not form an azeotrope with water.

In some exemplary embodiments of the invention, there is provided a method for the continuous treatment of biomass comprising: a pretreatment step, wherein the biomass is contacted with a first supercritical, near-critical, or sub-critical fluid to form a solid matrix and a first liquid fraction; wherein the first supercritical or near-critical fluid comprises water and at least one of $SO_2$ and a solvent; wherein the solvent is water-miscible and does not form an azeotrope with water: and a hydrolysis step, wherein the solid matrix is contacted with a second supercritical or near-critical fluid to produce a second liquid fraction and an insoluble lignin-containing fraction; wherein the second supercritical or near-critical fluid comprises water and at least one of $SO_2$ and a solvent; and wherein the solvent is water-miscible and does not form an azeotrope with water.

In some exemplary embodiments of the invention, there is provided a method of processing biomass comprising: a pretreatment step, wherein the biomass is contacted with a first supercritical, near-critical, or sub-critical fluid to form a pretreated slurry comprising a solid matrix and a first liquid fraction comprising xylo-oligosaccharides; wherein the first supercritical or near-critical fluid comprises water and at least one of $SO_2$ and a solvent; and wherein the solvent is water-miscible and does not form an azeotrope with water; a first separation step, wherein the solid matrix and the first liquid fraction are separated; a first hydrolysis step, wherein the solid matrix is contacted with a second supercritical or near-critical fluid to form an insoluble lignin-containing fraction and a second liquid fraction comprising cello-oligosaccharides; a second separation step, wherein the insoluble lignin-containing fraction and the second liquid fraction are separated; and a second hydrolysis step, wherein the second liquid fraction is contacted with a third near-critical or sub-critical fluid to form a product comprising glucose monomers; and wherein the third near-critical or sub-critical fluid comprises water and, optionally, acid.

In some exemplary embodiments of the invention, there is provided a method of processing biomass comprising: a pretreatment step, wherein the biomass is contacted with a first supercritical, near-critical, or sub-critical fluid to form a pretreated slurry comprising a solid matrix and a first liquid fraction comprising xylo-oligosaccharides; a first separation step, wherein the solid matrix and the first liquid fraction are separated; a first hydrolysis step, wherein the solid matrix is contacted with a second supercritical or near-critical fluid to form an insoluble lignin-containing fraction and a second liquid fraction comprising cello-oligosaccharides; wherein the first supercritical or near-critical fluid comprises water and at least one of $SO_2$ and a solvent; and wherein the solvent is water-miscible and does not form an azeotrope with water; a second separation step, wherein the insoluble lignin-containing fraction and the second liquid fraction are separated; and a second hydrolysis step, wherein the second liquid fraction is contacted with a third near-critical or sub-critical fluid to form a product comprising glucose monomers; and wherein the third near-critical or sub-critical fluid comprises water and, optionally, acid.

In some exemplary embodiments of the invention, there is provided a method of processing biomass comprising: a pretreatment step, wherein the biomass is contacted with a first supercritical, near-critical, or sub-critical fluid to form a pretreated slurry comprising a solid matrix and a first liquid fraction comprising xylo-oligosaccharides; wherein the first supercritical or near-critical fluid comprises water and at least one of $SO_2$ and a solvent; wherein the solvent is water-miscible and does not form an azeotrope with water; a first separation step, and wherein the solid matrix and the first liquid fraction are separated a first hydrolysis step, wherein the solid matrix is contacted with a second supercritical or near-critical fluid to form an insoluble lignin-containing fraction and a second liquid fraction comprising cello-oligosaccharides; wherein the first supercritical or near-critical fluid comprises water and at least one of $SO_2$ and a solvent; wherein the solvent is water-miscible and does not form an azeotrope with water; a second separation step, and wherein the insoluble lignin-containing fraction and the second liquid fraction are separated; and a second hydrolysis step, wherein the second liquid fraction is contacted with a third near-critical or sub-critical fluid to form a product comprising glucose monomers; and wherein the third near-critical or sub-critical fluid comprises water and, in some embodiments, acid.

In some embodiments, the first supercritical, near-critical, or sub-critical fluid comprises at least 100 ppm, at least 500 ppm, at least 1,000 ppm or even at least 2,000 ppm $SO_2$.

In some embodiments, the first supercritical, near-critical, or sub-critical fluid comprises less than 10%, less than 8%, less than 6%, or even less than 4% $SO_2$.

In some embodiments, the second supercritical, near-critical, or sub-critical fluid comprises at least 100 ppm, at least 500 ppm, at least 1,000 ppm or even at least 2,000 ppm $SO_2$.

In some embodiments, the second supercritical, near-critical, or sub-critical fluid comprises less than 10%, less than 8%, less than 6%, or even less than 4% $SO_2$.

In some embodiments, the solvent is acetone.

In some embodiments, the first supercritical, near-critical, or sub-critical fluid comprises at least 10%, at least 20%, at least 30%, at least 40%, at least 50% or even at least 60% solvent.

In some embodiments, the second supercritical or near-critical comprises at least 10%, at least 20%, at least 30%, at least 40%, at least 50% or even at least 60% solvent.

In some embodiments, the pretreatment step occurs at a temperature and pressure below the critical point of at least one component of the first supercritical, near-critical, or sub-critical fluid.

In some embodiments, the pretreatment step is performed at a temperature of about 100° C. to about 300° C.

In some embodiments, the pretreatment step is performed at a pressure of about 30 bar to about 115 bar.

In some embodiments, the method includes a first separation step after the pretreatment step and prior to the hydrolysis step, wherein the solid matrix and the first liquid fraction are separated.

In some embodiments, the first separation step is performed using an extruder or centrifugal press.

In some embodiments, the first liquid fraction comprises xylose oligosaccharides.

In some embodiments, the first liquid fraction comprises an amount of xylose oligosaccharides greater than about 50% of the maximum theoretical yield.

In some embodiments, the pretreatment step is continuous.

In some embodiments, the second fluid is a supercritical or near-critical fluid, and does not include an acid.

In some embodiments, the hydrolysis step occurs at a temperature and pressure above the critical point of at least one component of the second supercritical or near-critical fluid.

In some embodiments, the hydrolysis step occurs at a temperature from about 150° C. to about 450° C.

In some embodiments, the hydrolysis step occurs at a pressure of about 100 bar to about 250 bar.

In some embodiments, the hydrolysis step is continuous.

In some embodiments, the solid matrix is kept at a temperature of about 100° C. or higher from the beginning of the pretreatment step through at least the end of the hydrolysis step.

In some embodiments, the method includes a second separation step after the hydrolysis step, wherein the lignin fraction and the second liquid fraction are separated.

In some embodiments, the method includes a second hydrolysis step wherein the second liquid fraction is contacted with a third near-critical or sub-critical fluid to produce a third liquid fraction comprising glucose monomers; and wherein the third near-critical or sub-critical fluid comprises water and, In some embodiments, acid.

In some embodiments, the second hydrolysis step occurs at a temperature of about 150° C. to about 320° C.

In some embodiments, the second hydrolysis step occurs at a pressure of about 20 bar to about 90 bar.

In some embodiments, the acid is present in a catalytic amount.

In some embodiments, the acid is present in an amount less than about 1%.

In some embodiments, the acid is selected from the group consisting of hydrofluoric acid, hydrochloric acid, hydrobromic acid, hydroiodic acid, sulfuric acid, sulfonic acid, phosphoric acid, phosphonic acid, nitric acid, nitrous acid, and combinations thereof.

In some embodiments, the second liquid fraction has a residence time of about 1 second to about 30 seconds in the second hydrolysis step.

In some embodiments, the third liquid fraction comprises glycolaldehyde.

In some embodiments, the glycolaldehyde is present in an amount at least 10% of the theoretical maximum yield.

In some embodiments, the pressure exerted on the solid matrix is reduced to about 105 kPa or less after the hydrolysis step.

In some embodiments, the method includes after the hydrolysis step, reducing the pressure exerted on the solid matrix such that the lignin precipitates.

In some embodiments, the method includes: a xylo-oligosaccharide hydrolysis step, wherein the first liquid fraction is contacted with a fourth near-critical or sub-critical fluid to produce a fourth liquid fraction comprising xylose monomers; and wherein the fourth near-critical or sub-critical fluid comprises water and, In some embodiments, an acid.

In some embodiments, the acid is selected from the group consisting of hydrofluoric acid, hydrochloric acid, hydrobromic acid, hydroiodic acid, sulfuric acid, sulfonic acid, phosphoric acid, phosphonic acid, nitric acid, nitrous acid, and combinations thereof.

In some embodiments, the acid is present in an amount less than about 1%.

In some embodiments, the xylo-oligosaccharide hydrolysis step occurs at a temperature of about 150° C. to about 320° C.

In some embodiments, the xylo-oligosaccharide hydrolysis step occurs at a pressure of about 20 bar to about 90 bar.

In some embodiments, the method includes a third hydrolysis step, wherein the first liquid fraction is contacted with a fourth near-critical or sub-critical fluid to form a second product comprising xylose monomers; and wherein the fourth near-critical or sub-critical fluid comprises water and, In some embodiments, acid.

Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice of the present invention. In case of conflict, the patent specification, including definitions, will control. All materials, methods, and examples are illustrative only and are not limiting.

As used in this specification and the accompanying claims the term "supercritical fluid" is a fluid at a temperature above its critical temperature and at a pressure above its critical pressure. A supercritical fluid exists at or above its "critical point," the point of highest temperature and pressure at which the liquid and vapor (gas) phases can exist in equilibrium with one another. Above critical pressure and critical temperature, the distinction between liquid and gas phases disappears. A supercritical fluid possesses approximately the penetration properties of a gas simultaneously with the solvent properties of a liquid. Accordingly, supercritical fluid extraction has the benefit of high penetrability and good solvation.

Reported critical temperatures and pressures include: for pure water, a critical temperature of about 374.2° C., and a critical pressure of about 221 bar. Carbon dioxide has a critical point of about 31° C. and about 72.9 atmospheres (about 1072 psig). Ethanol has a critical point of about 243° C. and about 63 atmospheres. Methanol has a critical point of about 239° C. (512.8 K) and about 1174.0 psia (80.9 bar). The critical point for other alcohols can be ascertained from the literature or experimentally.

Near-critical water has a temperature at or above about 300° C. and below the critical temperature of water (374.2° C.), and a pressure high enough to ensure that all fluid is in the liquid phase.

Sub-critical water has a temperature of less than about 300° C. and a pressure high enough to ensure that all fluid is in the liquid phase. Sub-critical water temperature may be greater than about 250° C. and less than about 300° C., and in many instances sub-critical water has a temperature between about 250° C. and about 280° C.

As used herein, a fluid which is "supercritical" (e.g. supercritical water, supercritical ethanol, supercritical $CO_2$, etc.) indicates a fluid which would be supercritical if present in pure form under a given set of temperature and pressure conditions. For example, "supercritical water" indicates water present at a temperature of at least about 374.2° C. and a pressure of at least about 221 bar, whether the water is pure water, or present as a mixture (e.g. water and ethanol, water and $CO_2$, etc). Thus, for example, "a mixture of sub-critical water and supercritical carbon dioxide" indicates a mixture of water and carbon dioxide at a temperature and pressure above that of the critical point for carbon dioxide but below the critical point for water, regardless of whether the supercritical phase contains water and regardless of whether the water phase contains any carbon dioxide. For example, a mixture of sub-critical water and supercritical $CO_2$ may have a temperature of about 250° C. to about 280° C. and a pressure of at least about 225 bar.

As used in this specification and the accompanying claims the term "solid matrix" indicates a composition comprising a solid or particulate component.

As used in this specification and the accompanying claims the term "liquid fraction" indicates a liquid comprising at least one component which is a product of a reaction or treatment step. For example and without limitation, a liquid fraction after a hydrolysis step may include a product of the hydrolysis step with unreacted components and/or one or more additional products or by-products of the hydrolysis step and/or one or more products of a prior treatment step.

As used in this specification and the accompanying claims the term "continuous" indicates a process which is uninterrupted for its duration, or interrupted, paused or suspended only momentarily relative to the duration of the process. Treatment of biomass is "continuous" when biomass is fed into the apparatus without interruption or without a substantial interruption, or processing of said biomass is not done in a batch process.

As used in this specification and the accompanying claims the term "resides" indicates the length of time which a given portion or bolus of material is within a reaction zone or reactor vessel.

As used herein, the terms "comprising" and "including" or grammatical variants thereof are to be taken as specifying inclusion of the stated features, integers, actions or components without precluding the addition of one or more additional features, integers, actions, components or groups thereof.

Throughout this specification and the accompanying claims, percentages (%) of chemicals are W/W (weight per weight) unless otherwise indicated. In those cases where the weight percent is calculated relative to part of the composition, e.g. relative to the water component, the definition is provided explicitly, e.g. the weight percent of hydrochloric acid in an aqueous mixture may be provided by 100×HCl/ (HCl+Water), by weight in a given sample of the mixture.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

In order to understand the invention and to see how it may be carried out in practice, embodiments will now be described, by way of non-limiting example only, with reference to the accompanying figures. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are.

DETAILED DESCRIPTION OF THE EMBODIMENTS

Embodiments of the invention relate to systems and methods for processing lignocellulosic materials.

Specifically, some embodiments of the invention can be used to pre-treat lignocellulosic substrates prior to hydrolysis or a direct conversion process.

In some embodiments, this pre-treatment removes impurities present in the substrate which are not hydrolysis and/or direct conversion substrates. In some exemplary embodiments of the invention, this removal contributes to a decrease in downstream processing difficulties caused by the impurities. These difficulties may be associated with, for example, buildup of impurities on moving parts and/or clogging of passages (e.g. filters and/or nozzles) The impurities include, but are not limited to, ash (e.g. calcium and/or magnesium) and lipophilic material. Exemplary lipophilic materials are described below.

In some exemplary embodiments, the extracted substrate is hydrolyzed to form a liquid hydrolyzate and residual lignin solids. According to some exemplary embodiments, following hydrolysis, the lignin solids are separated from the hydrolyzate by filtration. In some exemplary embodiments of the invention, extraction of the lignocellulosic material prior to the hydrolysis contributes to an improvement in filtration rate (i.e. makes the liquid hydrolyzate go through the filter faster).

Figure 4:
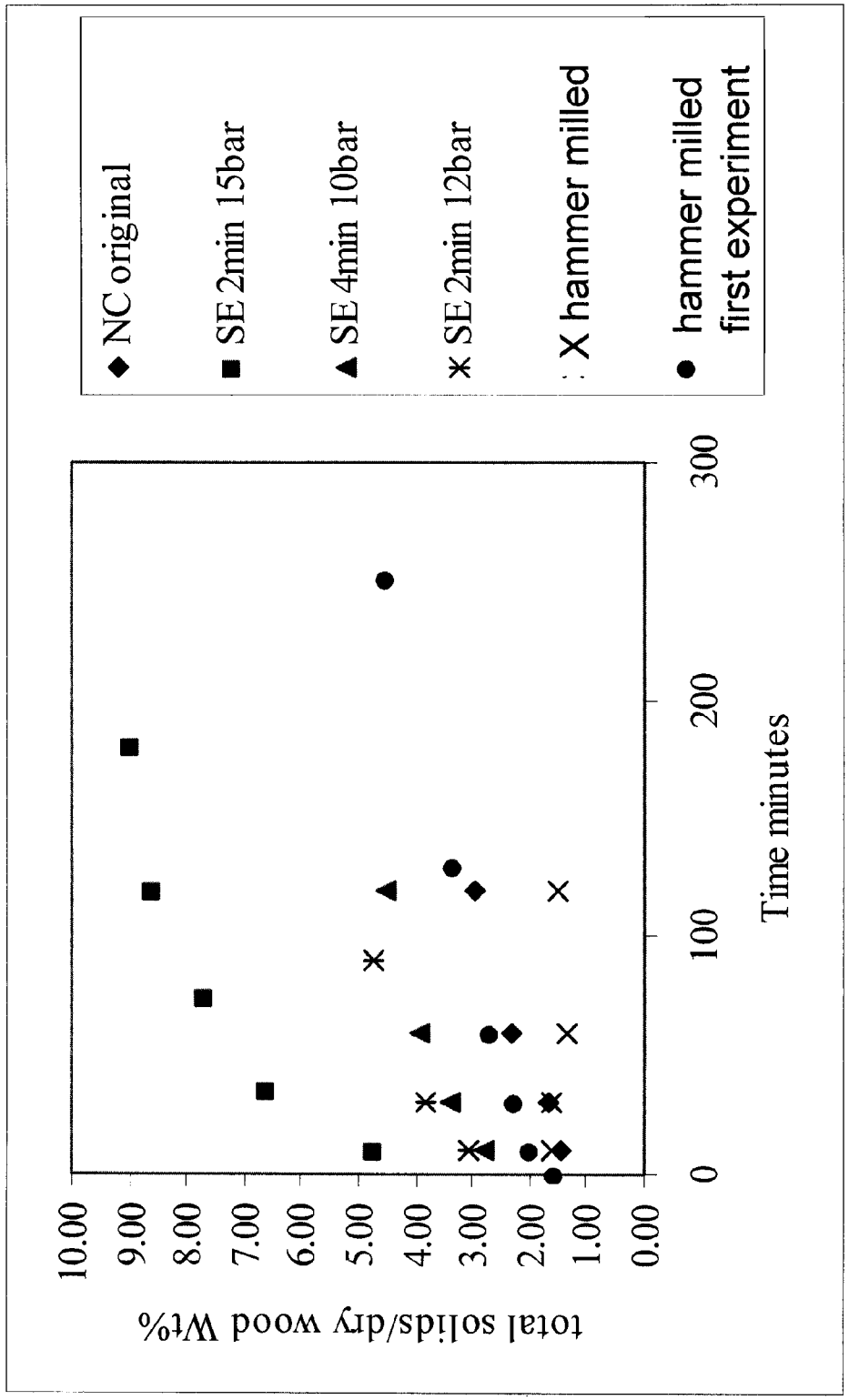
FIG. 4 is a graph of total solids/dry wood wt % as a function of time for different treatments associated with various exemplary embodiments of the invention.

The principles and operation of systems and/or methods according to exemplary embodiments of the invention may be better understood with reference to the drawings and accompanying descriptions. Drawings are referred to in an order that is believed to most clearly explain the accompanying claims. FIG. 4 includes experimental data and is referred to in the Examples section.

Before explaining at least one embodiment of the invention in detail, it is to be understood that the invention is not limited in its application to the details set forth in the following description or exemplified by the examples. The invention is capable of other embodiments or of being practiced or carried out in various ways. Also, it is to be understood that the phraseology and terminology employed herein is for the purpose of description and should not be regarded as limiting.

Exemplary System Overview

Figure 3:
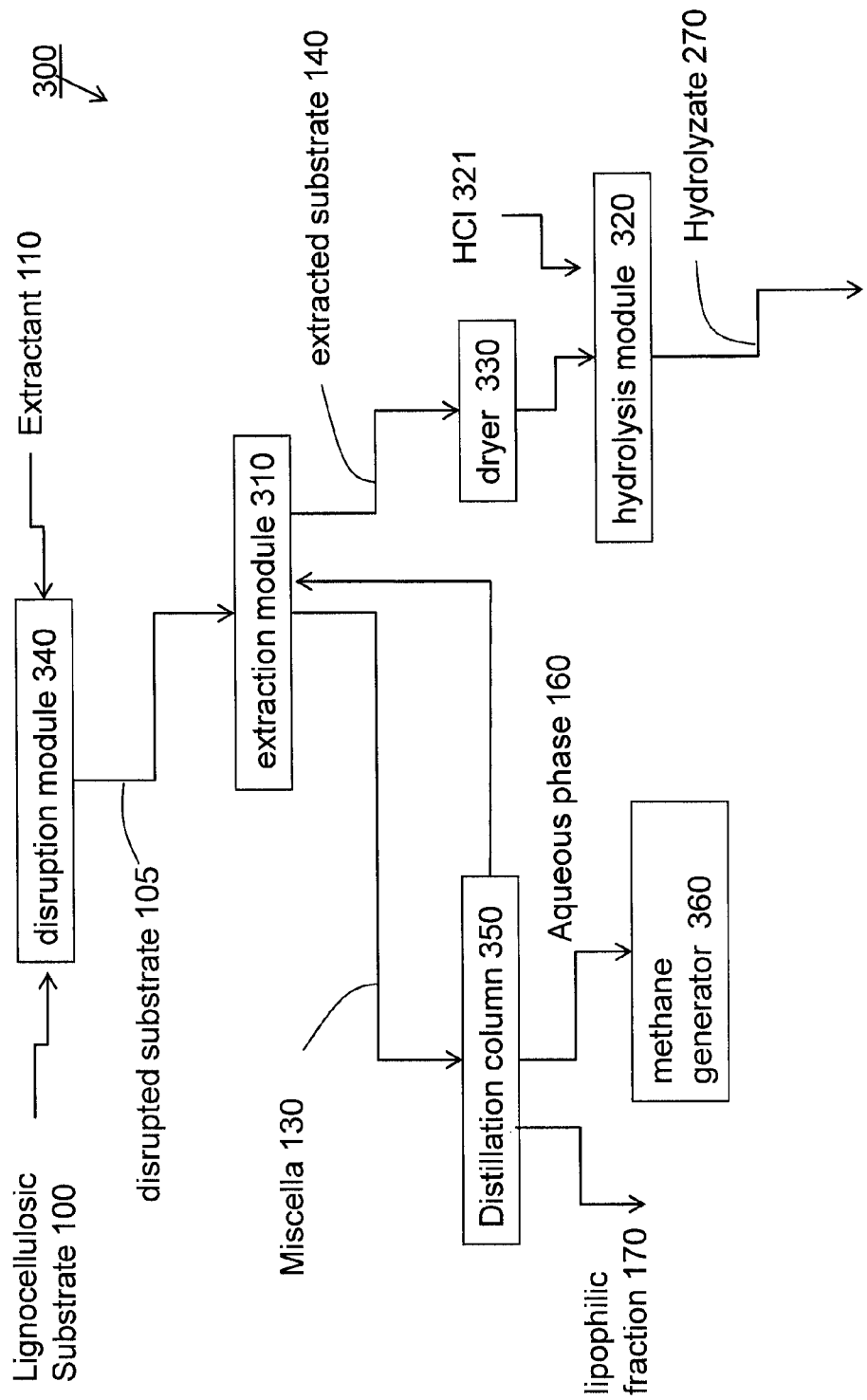
FIG. 3 is a schematic diagram of a system according to some exemplary embodiments of the invention.

FIG. 3 is a schematic representation of a system, indicated generally as 300, according to various exemplary embodiments of the invention.

Depicted exemplary system 300 includes an extraction module 310 adapted to extract a lignocellulosic substrate 100 with an extractant 110. Optionally, commercially available extraction equipment such as a Continuous Loop, Shallow Bed Extractor available from Crown Iron Works (Minneapolis, Minn., USA) is employed in extraction module 310. In some exemplary embodiments of the invention, extractant 110 includes a water-soluble organic solvent (e.g. acetone and/or ethanol). In some embodiments, extractant 110 includes a weak acid (e.g. sulfurous acid and/or acetic acid and/or phosphorous acid). Module 310 outputs an extracted substrate 140 and miscella 130. The term "miscella" as used in the specification and the accompanying claims indicates an extractant containing suspended particles and/or dissolved materials and/or liquids extracted from substrate. In some instances a miscella is an emulsion.

The quantitative and/or qualitative composition of miscella 130 will vary depending upon substrate 100 and extractant 110. According to various exemplary embodiments of the invention, miscella 130 can include resin(s) and/or pitch and/or tall oil(s) and/or terpene(s) and/or other volatile organic compound(s) and/or proteinaceous materials and/or ash. The quantitative composition of miscella 130 may also vary depending upon extraction conditions.

According to some exemplary embodiments, extraction module 310 performs extraction which is carried out at a temperature above ambient, greater than 30°, 40°, 50°, 60°, or 70° C. Alternatively or additionally, extraction module 310 performs extraction which occurs at a temperature less than 70°, 60°, 50°, 40° or 30° C. In some exemplary embodiments of the invention, extraction is carried out at a temperature in the range of from about 30° to about 80° C., from about 40° to about 70° C., or from about 50° to about 60° C. Optionally, increasing the temperature of extraction 310 can contribute to an increase in efficiency of extraction of one or more components of substrate 100.

In order to perform the extraction, module 310 receives lignocellulosic substrate 100 and extractant 110 separately and/or together as is illustrated by FIG. 3 and brings them into contact with one another. Optionally, module 310 includes a mixing apparatus (not depicted) to contribute to efficiency of this contact. In some exemplary embodiments of the invention, the mixing apparatus circulates extractant 110 through substrate 100 (e.g. by pumping and/or spraying).

Depicted exemplary system 300 includes a hydrolysis module 320 adapted to receive extracted substrate 140, or a dried version of extracted substrate 140 and contact it with an acid 321. Optionally, hydrolysis module 320 is adapted for acid hydrolysis. Exemplary acids that can be used are mineral acids, such as hydrochloric acid, sulfuric acid, nitric acid, phosphoric acid, and combinations thereof. In some exemplary embodiments, the mineral acid includes HCl and/or $H_2SO_4$. Optionally, concentration of the acid is 20, 30, 35, 37, 39, 41, 43 or 45% or intermediate or greater percentages. Hydrolysis module 320 produces hydrolyzate 270.

Various hydrolysis modules suitable for use in the context of module 320 are disclosed in, for example, co-pending application PCT/US11/57552 "HYDROLYSIS SYSTEMS AND METHODS" to JANSEN et al. filed on Oct. 24, 2011; which is fully incorporated herein by reference. In some embodiments, hydrolysis module 320 includes a single reactor with a countercurrent flow zone and a co-current flow zone and a trickling bed re-circulation system.

In some embodiments, system 300 includes a dryer 330 which removes residual extractant from extracted substrate 140. Dryer 330 may be, for example, a toaster-dryer. Commercially available toaster dryers suitable for use in this context include, but are not limited to, a Desolventizer-Toaster-Dryer-Cooler from the Crown Iron Works Company (Minneapolis, Minn., USA) and/or Barr-Rosin (Maidenhead, Berkshire; UK). Alternatively or additionally, dryer 330 may include a flash dryer. Optionally, a flash dryer can be used for a second removal. Optionally, residual extractant removed by dryer 330 is combined with miscella 130. In some exemplary embodiments of the invention, dryer 330 receives steam discharged (not shown) from disruption module 340. Optionally, this steam serves as a heat source. In some exemplary embodiments of the invention, this heat source is used to evaporate additional solvent from extracted substrate 140 prior to entry into hydrolysis module 320.

In some exemplary embodiments of the invention, system 300 includes a disruption module 340 adapted to apply a predetermined pressure-temperature-time profile to lignocellulosic substrate 100 to produce a disrupted substrate 105. According to various exemplary embodiments, disruption module 340 includes a plug screw feeder (also known as an expeller or expeller press) and/or a steam explosion (SE) reactor. Details on exemplary commercially available equipment to deliver such a predetermined pressure-temperature-time profile are provided in the section entitled "Exemplary Thermo-mechanical Treatment". According to various exemplary embodiments of the invention, disruption causes a breakdown in the microstructure of the lignocellulosic substrate, without an appreciable change in the macrostructure. In those embodiments where optional disruption module 340 is present, disrupted substrate 105 proceeds to extraction module 310.

In some exemplary embodiments of the invention, system 300 includes a distillation column 350 which receives miscella 130 and returns at least a portion of the solvent to extraction module 310 as indicated by an arrow. Alternatively or additionally, distillation column 350 separates impurities from miscella 130 and produces a lipophilic fraction 170 and an aqueous phase 160 comprising hydrocarbons. Optionally, lipophilic fraction 170 is processed to recover desired components (e.g. tall oils and/or resins). Various components in lipophilic fraction 170 can be used to produce adhesives, rubbers, inks, emulsifiers (e.g. in asphalt), cement binders, soaps, lubricants, as a component of a drilling fluid and in oil based varnishes.

In some exemplary embodiments of the invention, distillation column 350 includes commercially available equipment. Suitable equipment may be purchased, for example, from Applied Process Technology, Inc. (Cincinnati, Ohio; USA)

In some embodiments, distillation column 350 includes multiple columns. For example, distillation column 350 may include a miscella column, an acetone column and a pitch column. The miscella column can use an applied vacuum to remove 60% or more of the acetone out the top as a mixture containing VOCs (volatile organic compounds) and water. This acetone can continue to an acetone column and material remaining in the acetone column bottom may be directed to a pitch column.

According to these embodiments, the acetone column processes the mixture from the top of the miscella column under vacuum. The acetone leaves the acetone column through the top; the VOCs come out the middle; and the residual water/acetone mixture leaves through the bottom and goes to the pitch column.

In these embodiments, the pitch column boils the residual water/acetone mixture under slight negative pressure, until the acetone and a small fraction of the water come out the top leaving the tall oils and remaining water in the bottom. The insoluble fraction is separated from the soluble fraction by mechanical means such as decantation and/or filtration and/or centrifugation.

In some exemplary embodiments of the invention, aqueous phase 160 is routed to a methane generator 360. Optional methane generator 360 can use anaerobic digestion to produce methane. In some exemplary embodiments of the invention, methane from generator 360 serves as a fuel source for system 300 (e.g. to heat distillation column 350) and/or as fuel in a context not directly related to system 300. Optionally, methane from generator 360 supplements additional fuels originating outside system 300.

In some exemplary embodiments of the invention, aqueous phase 160 is filtered prior to anaerobic digestion, for example, using an ultra-filtration membrane. Aqueous phase 160 is alternatively or additionally subjected to sulfate reduction, for example, by liming and separation of the formed gypsum.

Exemplary Method

Figure 1:
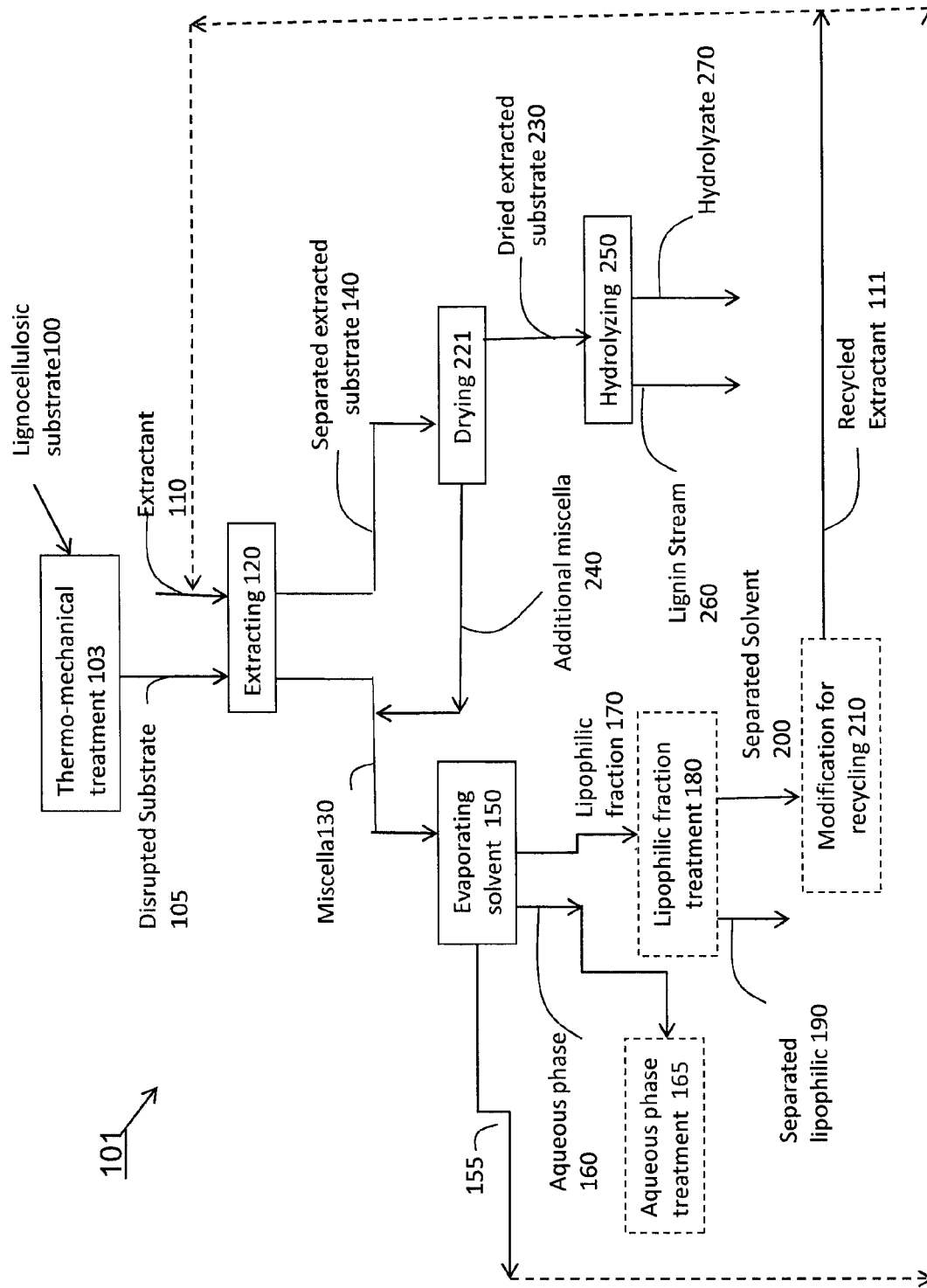
FIG. 1 is a simplified flow diagram of a method according to some exemplary embodiments of the invention.

FIG. 1 is a simplified flow diagram of a method according to some exemplary embodiments of the invention generally depicted as 101.

Depicted exemplary method 101 includes providing a lignocellulosic substrate 100 (e.g. wood) and contacting or extracting 120 the substrate with an extractant 110. According to various exemplary embodiments of the invention contacting or extracting 120 is conducted at a temperature of about 30° to about 80° C., optionally about 40° to about 70° C., optionally about 50° to about 60° C.

In some exemplary embodiments of the invention, extractant 110 includes a water-soluble organic solvent. Optionally, extractant 110 includes a weak acid. Extracting 120 produces, after separation, an extracted substrate 140, and a miscella 130. In the depicted exemplary embodiment, miscella 130 is initially removed from extracted substrate 140 passively, for example by draining. In depicted exemplary method 101, additional miscella 240 is removed from extracted substrate 140 to form dried extracted substrate 230 and additional miscella 240. Optionally, removal of additional miscella 240 is performed by drying 221. Drying 221 may include one or more forms of active removal including, but not limited to, heating (e.g. with steam) and/or centrifugation and/or pressing. In some embodiments, dried extracted substrate 230 is substantially de-solventized by drying 221.

Additional miscella 240 and miscella 130 each optionally comprise VOCs impurities and/or water and/or weak acid and/or solvent. In the depicted exemplary embodiment of the invention, additional miscella 240 is combined with miscella 130 for further processing. Optionally, miscellae 130 and 240 can be processed separately.

In some exemplary embodiments of the invention, method 101 includes hydrolyzing 250 of separated extracted substrate 140 and/or dried extracted substrate 230. According to various exemplary embodiments of the invention hydrolyzing 250 includes a chemically catalyzed process and/or an enzymatically catalyzed process. In some embodiments, chemically catalyzed processes employ a catalyst including a mineral acid (e.g. HCl and/or $H_2SO_4$) and/or a reactive fluid. In some embodiments, hydrolyzing 250 includes enzymatically hydrolyzing extracted substrate 140 and/or dried extracted substrate 230 using one or more enzymes.

Hydrolyzing 250 produces a hydrolyzate 270 rich in sugars and also produces a stream of residual lignin 260 including lignin solids. Thus, extracting 120 may be viewed as a "pre-treatment" of substrate 100 to remove impurities which could potentially complicate hydrolysis 250. In some embodiments, method 101 includes filtering lignin solids from hydrolyzate 270. According to these embodiments of the invention, extracting 120 contributes to an increase in a rate of this filtration. In some exemplary embodiments of the invention, a filtration rate of filtering lignin solids from hydrolyzate 270 is faster by at least 10% compared with a filtration rate of lignin solids from hydrolyzate formed by hydrolyzing the substrate without extracting 120, using an identical filter and identical filtration conditions.

In other exemplary embodiments of the invention, a thermal process involving exposure to temperatures in excess of 200° C. is substituted for hydrolysis 250. Exemplary thermal processes involving exposure to temperatures in excess of 200° C. include, but are not limited to pyrolysis and gasification According to various exemplary embodiments of the invention the pretreatment contributes to a reduction in complications in downstream processing of hydrolyzate 270 and/or lignin stream 260 and/or products of pyrolysis and/or products of gasification.

In some embodiments, the method includes subjecting extracted substrate 140 and/or 230 to a sulfite process.

In some embodiments, the sulfite process includes reacting the substrate with calcium sulfite at a pH of about 1 to about 2 and/or with magnesium sulfite at a pH of about 3 to about 5. Optionally, the reaction is carried out at a temperature of at least 115°, 125°, 130°, 140°, 145° or even 150° C. or more. In some embodiments, the reaction time is about 3, 4, 5, 6 or even 7 hours or more. These conditions can cause sulfonation and/or hydrolysis and/or condensation. Alternatively, some sulfite processes operate under neutral or alkaline conditions using sodium or ammonia as base. Additional details on sulfite processes can be found in Saake, B. and Lehnen, R. (2007) *Lignin* in Ullmann's Encyclopedia of Industrial Chemistry [available at
http://onlinelibraryDOTwileyDOTcom/doi/10.1002/14356007.a15_305.pub3/full]; which is fully incorporated herein by reference.

Exemplary Thermo-Mechanical Treatment

In some embodiments of the invention, method 101 includes a thermo-mechanical treatment 103. Optionally, treatment 103 disrupts substrate 100 by applying a predetermined pressure-temperature-time profile. According to these embodiments, the resultant disrupted substrate 105 is then subjected to extracting 120. According to some embodiments, the predetermined pressure-temperature-time profile is applied prior to extracting 120 of disrupted substrate 105. According to some embodiments, the resulting extracted disrupted substrate 140 is then subjected to downstream processing, as described hereinbelow.

In some exemplary embodiments of the invention, treatment 103 influences extracting 120. For example, physical disruption of substrate 100 may contribute to an increase of penetration of extractant 110 into disrupted substrate 105 (relative to substrate 100 under similar extraction conditions) during extracting 120. Optionally, this increase in penetration contributes to an increase in efficiency of extraction of one or more materials in the substrate. Alternatively or additionally, a proportion of extractant 110 recovered passively (e.g. by draining) as miscella 130, relative to the amount recovered actively (e.g. by centrifugation) as additional miscella 240 may be higher if treatment 103 is performed. Alternatively or additionally, a total amount of extractant 110 recovered as miscella 130 and additional miscella 240 may be higher if treatment 103 is performed. For example, in some instances at least 5, 10, 15, 20, 25, 30, 35, 40, 45, 50, 55, 60, 65, 70, 75, 80, 85, 90, or 95% of extractant 110 is recoverable through the processes described herein.

In some exemplary embodiments of the invention, thermo-mechanical treatment 103 includes a steam explosion treatment, and/or ammonia fiber explosion treatment. Optionally, the steam explosion treatment includes application of steam for a period of from about 30 seconds to about 3 minutes, such as, for example, about 30, 45, 60, 75, 90, 100, 110, 120, 150, 180 seconds, or intermediate or longer periods of time. According to some exemplary embodiments of the invention, steam is applied for a period of from about 45 to about 120 seconds. According to various exemplary embodiments of the invention steam is applied at a temperature of about 190°, 195°, 200°, 205°, or 210° C. or intermediate or greater temperatures. According to various exemplary embodiments of the invention steam is applied at a pressure of about 10, 11, 12, 13, 14 or 15 atmospheres or intermediate or greater pressures.

Treatment 103 can be ended by an abrupt discharge of pressure (venting) to return the substrate to ambient pressure and rapidly cool the substrate. Abrupt discharge can be accomplished by release of the substrate through an opening (nozzle), to form disrupted substrate 105. Steam explosion equipment is available commercially, for example from Andritz AG (Graz, Austria). In some exemplary embodiments of the invention, steam explosion is performed using an autoclave and venting the steam pressure suddenly to cause substrate explosion.

Alternatively or additionally, some exemplary embodiments of the invention employ an expeller, such as a plug screw feeder to thermo-mechanically treat 103 the substrate 100. An example of a commercial plug screw feeder amenable to incorporation into various exemplary embodiments of the invention is an Impressafiner (Andritz AG; Graz, Austria). Alternatively, Ajax LynFlow™ Plug Seal Screw Feeders (Ajax Equipment; Bolton, UK) can be employed. Plug screw feeders are also manufactured by MST corporation (Prineville, Oreg., USA).

In some exemplary embodiments of the invention, two or more predetermined pressure-temperature-time profiles are applied. For example, steam explosion, followed by a plug screw feeder.

In some exemplary embodiments of the invention, downstream processing of extracted disrupted substrate 140 includes at least one of hydrolysis 250, pyrolysis, and gasification.

In some exemplary embodiments, hydrolysis 250 comprises hydrolysis in the presence of at least one of a reactive fluid, and/or a mineral acid to produce soluble sugars. According to various exemplary embodiments of the invention these soluble sugars can serve as an energy source in aerobic respiration and/or anaerobic respiration and/or fermentation.

As used in this specification and the accompanying claims the term "reactive fluid" is defined as a fluid that is at a temperature higher than the boiling point of the liquid state of the fluid under atmospheric pressure (1 atm). The reactive fluid may be a liquid, a gas, a supercritical fluid, or a mixture of these. For example, water at a temperature above 100° C. and under atmospheric pressure is considered a reactive fluid. Supercritical, near critical, and sub-critical fluids are reactive fluids, illustrative examples including but not limited to sub-critical water, near critical water, supercritical water, supercritical ethanol, and supercritical $CO_2$.

Use of reactive fluids in the context of hydrolysis of lignocellulose is described in WO 2010/009343 which is fully incorporated herein by reference.

In some exemplary embodiments, the mineral acid comprises at least one of hydrochloric acid, sulfuric acid, nitric acid, phosphoric acid. In some exemplary embodiments of the invention, the mineral acid is hydrochloric acid. In other exemplary embodiments of the invention, the mineral acid is sulfuric acid.

In some exemplary embodiments, hydrolysis 250 comprises enzymatic hydrolysis to produce soluble sugars. Materials removed by extractant 110 might interfere with enzymatic activity if present during the enzymatic reaction.

According to various exemplary embodiments of the invention enzymes capable of hydrolyzing alpha and/or beta bonds are used.

According to various exemplary embodiments of the invention enzymatically hydrolyzing includes use of at least one enzyme belonging to EC 3.2.1 according to the Nomenclature Committee of the International Union of Biochemistry and Molecular Biology (NC-IUBMB) Enzyme Nomenclature Recommendations. This class of enzymes includes, but is not limited to, amylases, cellulases, hemicellulases, transglucosidases, glucoamylases, alpha-glucosidases and pullulanases. Optionally, an alpha amylase and/or a beta amylase and/or a 1-4 alpha glucosidase are employed.

It is expected that during the life of this patent many EC 3.2.1 enzymes will be characterized and the scope of the invention is intended to include all such new enzymes a priori.

For purposes of this specification and the accompanying claims, the term "enzyme" includes a single enzyme as well as a mixture including two or more enzymes. Optionally, an enzyme is provided as a crude preparation (e.g. cell extract) characterized by a type and/or level of activity, as opposed to a precise molecular definition. Alternatively or additionally, enzymes can be provided by incubation with living cells (e.g. in a fermentor using a suitable media). Optionally, specificity for a desired bond type can be achieved by appropriate enzyme selection and/or selection of suitable reaction conditions. In some exemplary embodiments of the invention at least 10% of disaccharides in the mixture are converted to monosaccharides by an enzymatic hydrolysis treatment at 250. Alternatively or additionally, at least 10% of oligosaccharides in a hydrolysis mixture are enzymatically hydrolyzed at 250 to release additional monosaccharides. In some exemplary embodiments of the invention, the enzymes are immobilized (e.g. on beads and/or a membrane). In some exemplary embodiments of the invention, immobilization contributes to an increase in yield of an enzymatic hydrolysis product per unit of enzyme.

In some exemplary embodiments, lignin extracted at 120 is less than 10%; optionally less than 5%; optionally less than 2%; and optionally less than 1% of lignin in the substrate prior to extraction.

Exemplary Solvent and Acid Considerations

Depicted exemplary method 101 employs an extractant including one or more water-soluble organic solvents and optionally includes one or more weak acids.

In some exemplary embodiments of the invention, the water-soluble organic solvent in extractant 110 has a solubility in water of about 40%, 50%, 60% or 70% wt or intermediate percentages (percent weight solvent to weight water) at 25° C. In some exemplary embodiments of the invention, the solvent is fully miscible with water.

Alternatively or additionally, in some embodiments of the invention, water has a solubility in the solvent of at 40%, 50%, 60%, 70% wt or intermediate percentages at 25° C.

In some embodiments, the water-soluble organic solvent has solubility in water of at least 50% at 25° C. and/or water has a solubility in the solvent of at least 50% at 25° C. As used in this specification and the accompanying claims the term "weak acid" refers to an acid having a pKa in the range of from 0 to 10, and analogs and derivatives thereof, including oxides thereof.

In some exemplary embodiments of the invention, the weak acid has a pKa greater than 0.1, optionally greater than 0.5 and optionally greater than 1.0. Alternatively or additionally, the weak acid has a pKa less than 6, optionally less than 5.5 and optionally less than 5.0. In some exemplary embodiments of the invention, the weak acid has a boiling point lower than 120° C., optionally lower than 100° C. at atmospheric pressure. According to some embodiments, a concentration of weak acid in the solvent is greater than 100, 300, 700, 1,000, 1,500 or 2,000 PPM. Alternatively or additionally, according to some embodiments, a concentration of weak acid in the solvent is less than 20,000; 15,000; 12,000 or 10,000 PPM. In some embodiments, a concentration of weak acid in the solvent is about 1,000 to about 15,000 PPM, or about 2,000 to about 12,000 PPM. Optionally, a concentration of weak acid in the solvent is optionally in the range of from about 100 to about 20,000 PPM, about 1,000 to about 15,000 PPM, or about 2,000 to about 12,000 PPM. In some exemplary embodiments of the invention, extractant 110 is formed by adding $SO_2$ to a mixture of solvent and water. In some embodiments, the concentrations of $SO_2$ can be 0.05-5%, 0.1-4%, 0.3-3% or 0.5-2%. Alternatively or additionally, the weak acid does not form an azeotrope with water.

Alternatively or additionally, the solvent does not form an azeotrope with water.

In some exemplary embodiments of the invention, a boiling point below 100° C., and/or failure to form an azeotrope with water, contribute to ease of acid recovery. Optionally, this makes it easier to recycle the acid for use in a subsequent extraction 120. Optionally, only a fraction of the acid is recovered, such that there is a need for acid make-up.

Optionally, the weak acid includes sulfurous acid and/or acetic acid and/or phosphorous acid and/or carbonic acid.

As used herein, the term "sulfurous acid" includes $SO_2$ as well as $H_2SO_3$. In some exemplary embodiments of the invention, the extractant is formed by contacting $SO_2$ with water. In some exemplary embodiments of the invention, first extractant 110 is formed by contacting an organic solvent and $SO_2$.

In some exemplary embodiments of the invention, contacting of the organic solvent and $SO_2$ is conducted in a vapor phase to form a vapor mixture, which on condensation forms first extractant 110, part Optionally, the vapor mixture includes water vapors and the extractant formed on condensation includes water of which reacts with $SO_2$ to form sulfurous acid. Alternatively or additionally, water is added after condensation. In some embodiments, part of the water used to form the sulfurous acid is added to first extractant 110 on contacting with water-containing lignocellulosic material (i.e. during extracting 120).

In some embodiments, sulfurous acid is present in extractant 110 at a concentration of 500 to 10,000 PPM, optionally 1,000 to 8,000 PPM, optionally 1,500 to 7,000 PPM. These embodiments optionally involve dissolving $SO_2$ in an acetone/water extractant.

In some exemplary embodiments of the invention, substrate 100 contains cations. In some embodiments, extractant 110 is provided in an amount sufficient to provide at least 0.5, 1.0, 1.5, 2.0, or 3.0 mole of the weak acid per equivalent of cations or intermediate or greater amounts of acid.

In some embodiments, lignocellulosic substrate 100 contains organic acids. In some embodiments, first extractant 110 is provided in an amount sufficient to provide at least 0.5, 1.0, 1.5, 2.0, or 3.0 mole of the weak acid per equivalent of organic acid or intermediate or greater amounts of weak acid.

Alternatively or additionally, in some exemplary embodiments of the invention, a ratio between the water-soluble organic solvent (e.g., acetone) in the first extractant and water in the substrate is at least 2.0; at least 2.5; at least 2.7; at least 2.9; or at least 3.5 or intermediate or greater values on a weight basis.

Exemplary Extraction Considerations

Referring again to FIG. 1, extracting 120 optionally includes two or more serial extractions. In some embodiments, each of these two or more extractions is performed as a counter current extraction.

In those embodiments of the invention which employ two or more serial extractions, with counter-current contacting between substrate 100 and extractant 110, unextracted substrate is contacted first with used extractant that has already contacted substrate one or more times and contains mineral ions and/or organic matter. In some instances, 2 or more, 3 or more, 4 or more or 5 or more serial extractions are conducted.

Following contact with this unextracted substrate, the liquid which is separated forms miscella 130. Note that this separation occurs after the first extraction from the standpoint of substrate 100, although it is the last extraction in the series from the standpoint of the extractant.

After separation of miscella 130, the lignocellulosic substrate 100 (now partially extracted) goes through one or more additional contacting stages and is eventually contacted with a fresh extractant 110 (i.e. not previously used). Note that this is the last extraction from the standpoint of substrate 100, although it is the first extraction in the series from the standpoint of extractant 110.

At this stage, the lignocellulosic material is separated from the extractant as extracted substrate 140. According to various exemplary embodiments of the invention, different forms of separation may be employed. In some embodiments, separation of lignocellulosic material from the extractant involves pressing and/or decantation and/or filtration and/or centrifugation.

In some embodiments, extractant 110 is passed through two or more contacting vessels containing substrate lignocellulosic substrate 100. Optionally, the number of extractions 120 and/or contacting vessels is greater than 3 and/or less than 9. In some embodiments, the number of extractions 120 and/or contacting vessels is 5, 6 or 7. Optionally, a number of extractions 120 and/or contacting vessels can be adjusted based upon the amount of impurities in substrate 100, which can be determined empirically using laboratory techniques. Alternatively or additionally, increasing a number of extractions 120 and/or contacting vessels contributes to an increase in efficiency of extraction with a given volume of extractant 110.

In some exemplary embodiments of the invention, extraction 120 includes two or more extractions which are not identical to one another. According to various exemplary embodiments of the invention the extractions may differ in temperature conditions and/or duration and/or number of extraction stages and/or extractant 110.

In some exemplary embodiments of the invention, each of said two or more extractions is characterized by a ratio [w/w] between the weak acid and the solvent in extractant 110 independent of a same ratio in one or more other extractions of the two or more extractions. In some embodiments, during modification for recycling 210 described hereinbelow, extract recycling forms an acid depleted fraction and an acid-rich fraction that are used in said two or more extractions.

In some exemplary embodiments of the invention, extraction 120 is performed in a continuous loop, shallow bed extractor. An example of a commercial continuous loop, shallow bed extractor that may be adapted for use in the context of exemplary embodiments of the invention is the Model III Solvent Extractor (Crown Iron Works Company; Roseville, Minn., USA).

Figure 2:
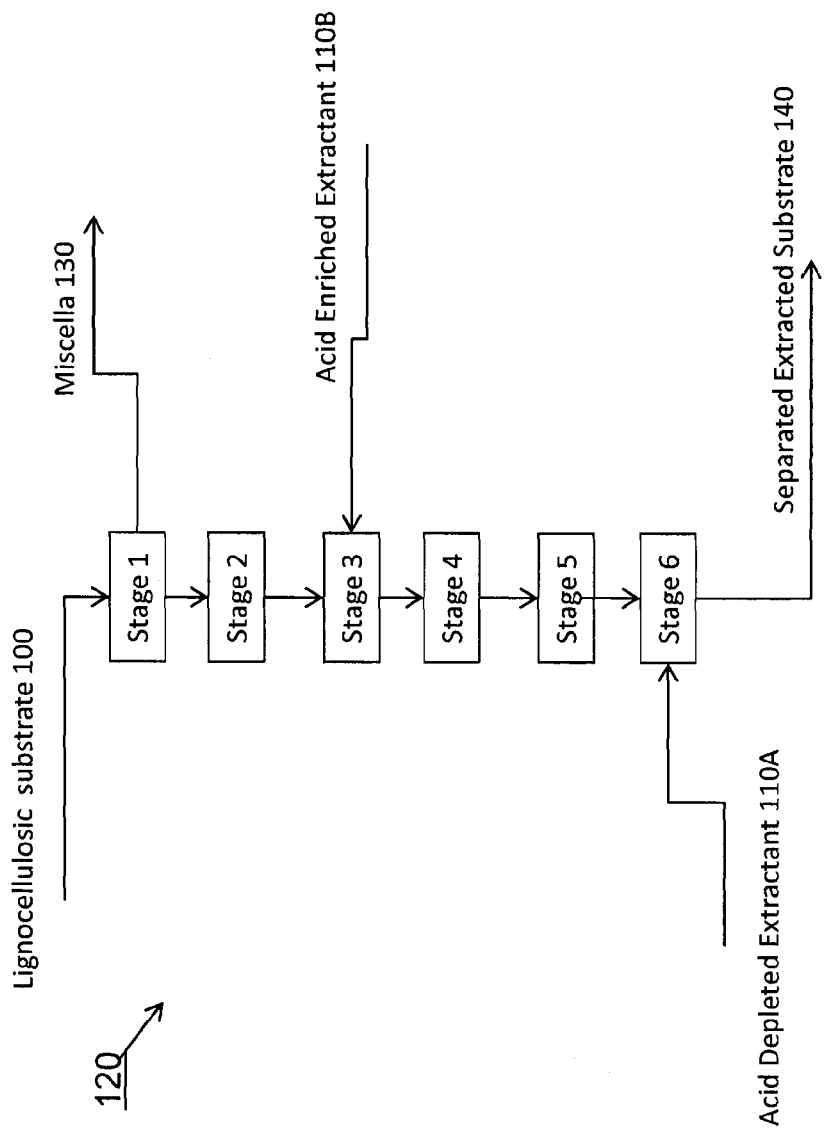
FIG. 2 is a simplified flow diagram of a method according to some exemplary embodiments of the depicting the extraction portion of the method in greater detail.

Referring now to FIG. 2, extracting 120, including two or more extractions is illustrated in more detail in a simplified flow scheme. In the depicted exemplary embodiment, multi-stage contacting with six stages and the use of extractants having different weak acid content is diagrammed. In the diagram, flow of substrate is downwards and flow of extractant is upwards.

FIG. 2 employs numerals similar to those used in FIG. 1 when referring to similar materials or streams. In the depicted embodiment, extractant is added only at stages 3 and 6. According to the depicted embodiment, lignocellulosic substrate 100 is contacted in stage 1 with a mixture which has already contacted substrate in stages 2 and 3. The mixture includes acid-rich first extractant 110B and an acid-depleted second extractant 110A. As substrate 100 progresses to stages 2 and 3, the mixture with which it is in contact has progressively lower concentrations of extracted impurities.

As substrate 100 progresses to stages 4 to 6, it is serially extracted by acid depleted extractant 110A which enters at stage 6 and flows upwards. As a result, the last extraction of substrate 100 at stage 6 is with a first extractant depleted with respect to weak-acid.

In some embodiments, extractants 110A and/or 110B include water. According to various exemplary embodiments of the invention a ratio between water and solvent in each of the stages is controlled independently, for example by controlling the amount of extractant added in each of the stages, taking into account to the amount of water contained in said substrate 100 in each of the stages and in its flow rate.

Exemplary Optional Second Extraction

Referring again to FIG. 1: In some exemplary embodiments of the invention, method 101 includes performing an additional extraction with a second extractant which contains a water-soluble organic solvent. According to various exemplary embodiments of the invention this additional extractant may be with the same extractant 110 or two different extractants may be employed (see 110A and 110B of FIG. 2). In some embodiments, differences between the extractants may include differences in acid type and/or acid concentration and/or solvent type and/or solvent concentration.

In some exemplary embodiments of the invention, the second extractant comprises a lower concentration of weak acid than the first extractant or comprises no weak acid.

In some exemplary embodiments of the invention, the second extractant comprises organic solvent similar to that of the solvent of the first extractant.

In some exemplary embodiments of the invention, the additional extraction includes wetting of substrate 100 with the second extractant prior to thermo-mechanical treatment 103.

Exemplary Processing of Extracted Substrate

As shown in FIG. 1, in some exemplary embodiments of the invention, extracting 120 of a lignocellulosic substrate 100 with an extractant 110 comprising a water-soluble organic solvent produces, after removal of miscella 130, an extracted substrate 140.

In some embodiments, removal of miscella 130 comprises passive removal, such as draining. Alternatively or additionally, removal of miscella 130 comprises active removal, such as centrifugation.

In some embodiments of the invention, extracted substrate 140 is hydrolyzed 250 to produce a hydrolyzate 270 rich in sugars as well as a stream of residual lignin 260. Hydrolysis 250 may be performed in the presence of one or more mineral acids, such as hydrochloric acid and/or sulfuric acid and/or nitric acid and/or phosphoric acid. In some exemplary embodiments, the mineral acid is HCl. In other exemplary embodiments of the invention, the mineral acid is $H_2SO_4$.

Alternatively or additionally, extracted substrate 140 may be subjected to pyrolysis and/or gasification and/or hydrolysis in the presence of a reactive fluid.

In some exemplary embodiments, pyrolysis comprises use of at least one of a fixed bed reactor, an Auger reactor, an ablative reactor, a rotating cone reactor, and a fluidized bed reactor.

In some embodiments, extractant 110 comprises a weak acid (e.g. sulfurous acid and/or acetic acid).

In some embodiments, substrate 100 is disrupted by application of a predetermined pressure-temperature-time profile thereto.

In some embodiments, following extraction, extractant 110 is separated from miscella 130.

In some embodiments, subsequent to removal of miscella 130 from extracted substrate 140, substrate 140 is subjected to a sulfite process.

As used in this specification and the accompanying claims the term "sulfite process" indicates any process which produces cellulose fibers from a lignocellulosic substrate by using various salts of sulfurous acid to extract the lignin from the substrate. In some embodiments, the extraction is performed in large pressure vessels called digesters. According to various exemplary embodiments of the invention, salts used in the pulping process are either sulfites ($SO_3^{2-}$), or bisulfites ($HSO_3^-$), depending on the pH. Optionally, the counter ion can be sodium ($Na^+$), calcium ($Ca^{2+}$), potassium ($K^+$), magnesium ($Mg^{2+}$) or ammonium ($NH4^+$).

According to various embodiments of the invention the sulfite process is followed by hydrolyzing 250 of extracted substrate 140 using a mineral acid as catalyst, and/or pyrolyzing extracted substrate 140, and/or gasifying extracted substrate 140, and/or hydrolyzing extracted substrate 140 in the presence of a reactive fluid.

Additional Exemplary Method

Figure 7:
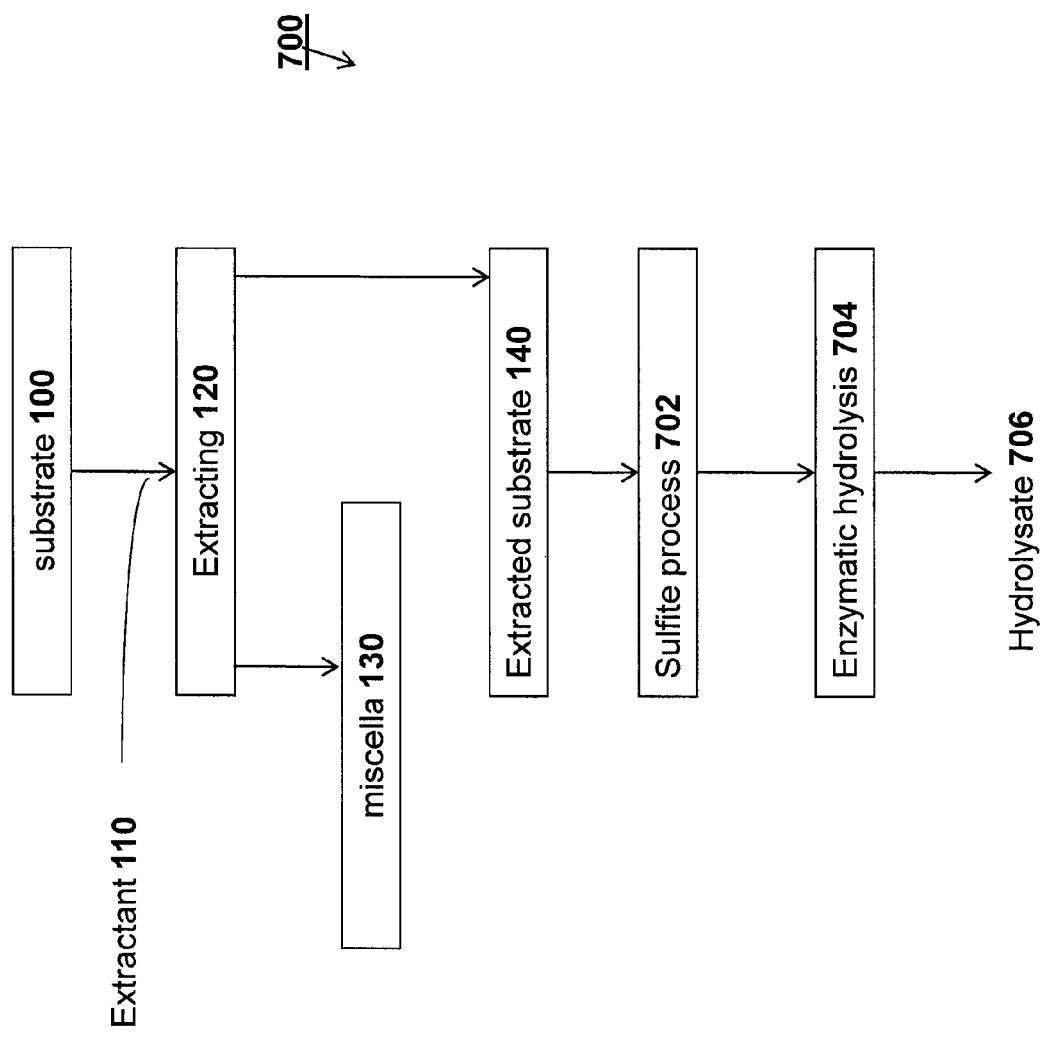
FIG. 7 is a simplified flow diagram of a method according to some exemplary embodiments of the invention.

FIG. 7 is a simplified flow diagram of a method of enzymatic hydrolysis of a lignocellulosic substrate indicated generally as method 700. Depicted exemplary method 700 includes extracting 120 lignocellulosic substrate 100 with an extractant 110 comprising a water-soluble organic solvent. Extracting 120 produces an extracted substrate 140 and a miscella 130. Method 700 also includes removing miscella 130 from the extracted substrate 140.

According to depicted exemplary method 700, extracted substrate 140 is subjected to a sulfite process 702. Sulfite process 702 dissolves lignin. Depicted exemplary method 700, continues with enzymatic hydrolysis 704 of extracted substrate 140. In other exemplary embodiments of the invention, other types of hydrolysis are employee (e.g. using a mineral acid and/or reactive fluid). Hydrolysis 704 produces a hydrolysate 706. In some exemplary embodiments of the invention, extractant 110 includes a weak acid as described hereinabove. In some embodiments, the weak acid includes sulfurous acid. In some exemplary embodiments of the invention, the sulfurous acid is formed by adding $SO_2$ to a mixture of solvent and water. Optionally, the concentrations of weak acid are as described hereinabove.

Alternatively or additionally, in some exemplary embodiments, a predetermined-pressure-temperature-time profile is applied to substrate 100 prior to extracting 120 as described hereinabove.

Exemplary Recycling Considerations

In some exemplary embodiments of the invention, method 101 (FIG. 1) includes separating solvent and/or weak acid from miscella 130 to form a recycling stream (155 and/or 111) including solvent and/or weak acid. In some embodiments, the separating of the solvent includes evaporation 150 and/or and extraction into another solvent. In the depicted embodiment, the solvent is separated by evaporation 150, optionally in an evaporation module. In some embodiments, the weak acid is sulfurous acid and excess of $SO_2$ is evaporated from miscella 130. According to various exemplary embodiments of the invention the method includes separating at least a portion of the water-soluble organic solvent and/or the weak acid from miscella 130 and/or 240.

In some exemplary embodiments of the invention, evaporation 150 is conducted to further separate the recycled solvent 155 and/or weak acid and to form an acid-rich fraction ($SO_2$ rich vapor fraction) and an acid-depleted fraction. Optionally, the acid-depleted vapor phase is condensed to form a weak acid-depleted liquid phase and the acid-rich vapor phase is condensed to form a weak acid-rich liquid phase. Optionally, recycled solvent 155 is combined with recycled extractant 111 as indicated by dashed arrows.

In some exemplary embodiments of the invention, (FIG. 2) the weak acid-depleted liquid phase 110A and/or the acid-rich vapor fraction 110B collectively designated in FIG. 1 as extractant 110 are separately modified and separately recycled via module 210 to extracting 120.

In some exemplary embodiments of the invention, miscella 130 includes water (in aqueous phase 160) and a lipophilic fraction 170. Optionally, lipophilic fraction 170 is gradually separated (e.g. by stepwise distillation) from miscella 130 to form an aqueous phase 160 and a lipophilic fraction 170 for example by gradual evaporation of solvent, weak acid and volatile organic compounds. As used in this specification and the accompanying claims the terms "distill" and "distillation" include all methods of separation based upon differential evaporation. Optionally, the separating of the water-soluble organic solvent and the weak acid from miscella 130 forms an aqueous phase 160. In some embodiments, water and water-soluble impurities in aqueous phase 160 are modified and recycled in optional aqueous phase treatment 165.

In some exemplary embodiments of the invention, aqueous phase 160 includes a substantial quantity of carbohydrates and aqueous phase treatment 165 comprises anaerobic treatment of aqueous phase 160 to produce methane. In some embodiments, this methane is used as an energy source in the process (e.g. combusted to heat a still or to provide steam for steam explosion).

In some embodiments of the invention, evaporation 150 includes distilling of miscella 130 to produce a solvent phase (depicted as arrow 155), aqueous phase 160 and lipophilic fraction 170. In some embodiments, the solvent phase includes distillation overheads. In some embodiments, aqueous phase 160 and/or lipophilic fraction 170 remain in the bottom phase. In some embodiments, aqueous phase 160 and lipophilic fraction 170 are separated for example by decantation, cyclone separators or centrifuges. In some embodiments, separation of lipophilic material 190 is conducted at an elevated temperature. The elevated temperature may be important if the lipophilic material has a high melting point. In some embodiments, separated aqueous phase 160 is biologically (optionally anaerobically) digested. According to various exemplary embodiments of the invention the COD (Chemical Oxygen Demand) of separated aqueous phase 160 is in the range of 5,000 to 100,000 PPM, optionally 10,000 to 80,000 PPM, optionally 15,000 to 70,000 PPM, optionally 20,000-50,000 PPM. In some exemplary embodiments of the invention, the sulfite/sulfate content of aqueous phase 160 to be treated is kept below 10,000 PPM, optionally below 8,000 PPM, optionally below 6,000 PPM, optionally below 4000 PPM, optionally below 2000 PPM. In some embodiments, aqueous phase 160 is treated with lime before biological digestion to remove sulfur as precipitated CaSO3/CaSO4.

In some embodiments, method 101 includes lipophilic fraction treatment 180 of lipophilic fraction 170. In some exemplary embodiments, the solvent phase comprises the water-soluble organic solvent 200 and at least a portion of the weak acid. In some embodiments, treatment 180 includes additional fractionation of lipophilic fraction 170 to separated lipophilics 190 and separated solvent 200.

In some exemplary embodiments, aqueous phase 160 comprises less than 10%, 8%, 5%, 3% or 1% carbohydrates or lesser or intermediate amounts.

In some embodiments, liphophilic phase 170 is desolventized, optionally using steam from steam explosion 103.

In some embodiments, method 101 includes periodic harvest of a separated lipophilic fraction 170 separated from miscella 130 during distillation of water-soluble organic solvent and the weak acid by evaporating 150. In those embodiments of the invention which employ steam explosion, the released steam can optionally be used as a source of heat energy for evaporating 150, which optionally takes the form of distillation.

In some exemplary embodiments of the invention, lipophilic fraction treatment 180 includes fractionation of lipophilic fraction 170. In some embodiments, fractionation is by step-wise solvent removal.

Alternatively or additionally, lipophilic fraction treatment 180 includes further evaporating $SO_2$ and solvent together to form a vapor mixture. Optionally, the vapor mixture is condensed to form separated solvent solution 200 which includes solvent and $SO_2$ (optionally as $H_2SO_3$). Optionally, solution 200 is recycled to extracting 120. In some embodiments, separated solvent 200 to be recycled is modified by modification module 210.

Optionally, the weak acid is not fully separated. Part of the weak acid may form (water-soluble) salts that remain in the miscella. For example, when sulfurous/$SO_2$ is used, it can oxidize partially into sulfuric/$SO_3$, which is more difficult to separate. Optionally, air is removed from substrate 100 prior to extracting 120, e.g. by steaming. In some exemplary embodiments of the invention, this steaming contributes to a reduction in contact between air and extractant 110 during extracting 120.

In some exemplary embodiments of the invention, modification includes removal of a fraction of, ioptionall substantially all of, VOCs from the solvent, e.g. by distillation. According to various exemplary embodiments of the invention recycled extractant 111 is used as extractant 110 in a subsequent round of extracting, optionally in combination with recycled solvent 155.

Exemplary Solvent Recycling

Referring again to FIG. 1: In some exemplary embodiments of the invention, water-soluble solvent in extractant 110 is at least partially recycled from a previous extraction and/or a previous extraction stage (e.g. 155 and/or 111 in FIG. 1). In some embodiments, recycling involves distillation from a miscella (e.g. 130 and/or 240). Typically, distillation leaves some water in the solvent. Condensation of vapors from the distillation column forms a mixture of water and solvent. For example, if acetone is used as the solvent, condensation can form a mixture of acetone:water at ratio of about 90:10. Extractant 110 can then be prepared by adding $SO_2$ to this acetone/water mixture.

In some embodiments, solvent phase 155 includes water-soluble organic solvent and at least a portion of the weak acid provided in the extractant. As indicated in FIG. 1, recovered solvent 155 is optionally re-used as part of extractant 110 in extracting 120.

According to various exemplary embodiments of the invention the recycled extractant contains about 70% to 95% solvent and 30% to 5% water. In some embodiments, the recycled extractant contains about 90% solvent and about 10% water. According to these embodiments, extracting 120 is with an extractant comprising solvent and water.

In some embodiments, the solvent/substrate ratio is selected so that the water content of the extractant increases to about 20%, optionally to about 30%, optionally to about 40%, optionally to about 50%, optionally to about 60% or even to about, to about 70% or more due to water transfer from the substrate.

During subsequent extraction 120, extractant 110 picks up water from substrate 100. If substrate 100 is wood, such as pine wood, it typically includes slightly more than 50% water at the beginning of extraction 120 and exits as extracted substrate 140 with about 10% water. At the same time, miscella 130 carries a correspondingly larger amount of water than extractant 110.

In some exemplary embodiments of the invention, miscella 130 contains about 45% water. According to various exemplary embodiments of the invention, this percentage may vary with one or more of the water content of substrate 100 (or disrupted substrate 105) and/or the amount of water in extractant 110 and/or the ratio of extractant to substrate applied during extracting 120.

In some exemplary embodiments of the invention, solvent is first distilled from miscella 130 and the vapors are condensed to reform a solvent-water mixture. In many cases the weak acid is extracted with the solvent and is condensed with it to reform extractant 110. In some embodiments, reconstitution of extractant 110 includes some acid makeup (i.e. addition of fresh acid).

As the concentration of the solvent in the miscella deceases, lipophilic material(s) can precipitate out. In some cases, this precipitated lipophilic material may still contain some solvent. Optionally, another distillation (lipophilic fraction treatment 180) separates residual solvent 200.

Optionally, steam formed on depressurizing the steam explosion (thermo-mechanical treatment 103) can be used for distillation (e.g. 180) of lipophilic fraction 170. Optionally, distilling the solvent from the miscella is divided into several steps. This results in division of the lipophilic fraction 170 into several fractions. Optionally, this division contributes to an increase in total value.

Exemplary Extraction Effects

In some exemplary embodiments of the invention, lignocellulosic substrate 100 includes water. Optionally, extracting 120 transfers water from substrate 100 to extractant 110.

According to various exemplary embodiments of the invention the initial water content of lignocellulosic substrate 100 is in the range of from about 10% to about 90% wt, optionally from about 20% to about 80% wt, from about 30% to about 70% wt, or from about 40% to about 60% wt.

According to various exemplary embodiments of the invention the water content of extracted substrate 140 is optionally in the range of from about 1% to about 40% wt, from about 2% to about 30% wt, from about 5% to about 25% wt, or from about 10% to about 20% wt. According to various exemplary embodiments of the invention extraction 120 lowers the water content of the substrate from about 50% to about 25%, about 50% to about 20%, about 50% to about 18%, about 50% to about 16%, or intermediate or lower percentages. Alternatively or additionally, according to various exemplary embodiments of the invention extraction 120 lowers the water content of extracted substrate 140 to less than about 25%, optionally less than 20%, and optionally less than about 18% of the water provided in lignocellulosic substrate 100.

In some exemplary embodiments of the invention, thermo-mechanical treatment 103 contributes to an increase in the difference in water content between substrate 100 and extracted substrate 140. According to various embodiments of the invention, the initial water content of extractant 110 is in the range of from about 1% to about 30% wt, or about 2% to about 20% wt, or from about 5% to about 15% wt, or about 8% to about 12% wt. Alternatively or additionally, a, the water content of the extractant after extraction is in the range of from about 20% to about 80% wt, or from about 30% to about 70% wt, or from about 40% to about 60% wt.

In some embodiments, water content in miscella 130 is greater than water content of extractant 110 by at least 10%, at least 20%, at least 30% or more. This difference comes in large part from water extracted from the substrate. In some exemplary embodiments of the invention, at least 50% of water originally present in substrate 100 is removed and transferred to miscella 130 and/or additional miscella 240. In some embodiments, water content of extracted substrate 140 is less than 20% wt, less than 15% wt, or less than 8% wt.

In some embodiments of the invention, 50%, 65% or even, 75% or more of the ash content of substrate 110 is extracted to miscella 130. In some substrates 100 calcium and magnesium form a large fraction of the cation content of the ash. In some exemplary embodiments of the invention, at least 50%, at least 60%, or even 75% or more of the magnesium and/or calcium contents of substrate 100 is extracted to miscella 130. These levels of ash extraction from substrate 100 are significantly more efficient than previously available alternatives.

In some exemplary embodiments of the invention, extracted substrate 140 contains less than 50% of the calcium and magnesium content provided in substrate 110. In some exemplary embodiments of the invention, extracted substrate 140 contains less than 80%, less than 70%, less than 60%, or less than 50% of the lipophilic fraction material originally present in substrate 100. These levels of lipophilic fraction removal from substrate 100 are significantly more efficient than previously available alternatives.

In other words, at least 20%, at least 30%, at least 40%, at least 50%, at least 60%, at least 70%, at least 80% or at least 90% of the lipophilic fraction material of originally present in substrate 100, as determined by DCM extraction, migrates to miscella 130.

Alternatively or additionally, extracted substrate 140 contains less than 60%, 50%, 40%, or 30% of the pectin provided in lignocellulosic substrate 100.

Alternatively or additionally, the total amount of material extracted during contacting (extracting 120) is 0.5-10%, 1% to 9%, 2% to 8%, or 3% to 7% calculated based on the dry weight of substrate 100.

Alternatively or additionally, a carbohydrate content of miscella 130 is less than 10%, less than 8%, less than 4%, or less than 2% of the carbohydrates in substrate 100.

Exemplary Hydrolysis Considerations

In some exemplary embodiments of the invention, dried extracted substrate 230 is hydrolyzed 250. In some embodiments, hydrolyzing 250 is accomplished by contacting with an aqueous hydrolysis medium with a weight ratio of HCl to (HCl+water) of 30%, 35%, 37%, 40%, 42%, 45% or intermediate or greater percentages.

In some embodiments of the invention, hydrolysis is improved by the extraction described above. Optionally, the improvement can be in hydrolysis rate and/or in one or more hydrolyzate parameters. Hydrolyzate parameters include, but are not limited to, sugar composition and/or concentration of substrate derived impurities and/or concentration of degradation products of sugars.

Hydrolysis 250 produces hydrolyzate 270 including HCl and at least one carbohydrate as well as a residual lignin stream 260 which includes lignin, HCl and water. Typically, streams 260 and 270 are separated and each is subjected to appropriate downstream processing.

Hydrolyzate 270 is processed to remove acid and/or increase sugar content and/or modify sugar composition. Downstream processing of hydrolyzate 270 may be, for example, according to methods disclosed in co-pending provisional patent application U.S. 61/500,169.

Lignin stream 260 is processed to remove acid and/or deacidify the lignin and/or dry the lignin and/or recover residual sugars. Downstream processing of lignin 260 may be, for example, according to methods disclosed in co-pending provisional patent application U.S. 61/491,243 which is fully incorporated herein by reference.

In some exemplary embodiments of the invention, hydrolyzate 270 contains 2%, 1%, or even 0.5% or less solids. Practice of extraction methods as described hereinabove optionally contributes to a reduction in this solids percentage.

Exemplary Interactions Between Substrate and Practice of Exemplary Methods

According to various embodiments of the invention any lignocellulosic material can serve as substrate 100. In some exemplary embodiments of the invention, substrate 100 includes one or more of wood, sugarcane bagasse, agricultural residues, oil palm biomass, energy crops and recycled biomass. In some embodiments substrate 100 is provided as wood chips, for example chips with a largest measurement of 4 inches, 3 inches, 2 inches, 1.5 inches or 1 inch or intermediate or smaller measurements. In some embodiments of the invention, a soft wood, such as pine, is used as substrate 100.

Typically, substrate 100 includes at least 10%, 20% or even 30% or more water. In some exemplary embodiments of the invention, substrate 100 is not dried prior to extracting 120 or is slightly dried to a water level in the range of 40% to 50%. This slight drying may be accomplished, for example, by harvesting the substrate and allowing it to stand prior to using it as substrate 100. In some embodiments, standing continues for 5, 10, 15, 20, 30 or 40 or an intermediate or greater number of days. In some embodiments of the invention, wood serves as a substrate and stands for at least 5 days prior to use. Alternatively or additionally, the substrate is processed to increase surface area prior to standing. Optionally, the substrate is wood and an increase in surface is achieved by splitting logs and/or chipping the wood. In some exemplary embodiments of the invention, increasing surface area contributes to an increase in drying speed and/or a reduction in volatile organic compounds and/or resins present in the substrate.

Exemplary Impurities and Associated Problems

Substrate 100 has been described as containing impurities which include ash and a lipophilic fraction. The term "ash" refers to those materials which remain after complete combustion of the substrate as accepted in the art.

The lipophilic fraction includes non-lignin, non-cellulosic, non-ash material such as resins, pitch, tall oils, terpenes (and other volatile organic compounds) and proteinaceous materials. Measurement of the lipophilic fraction in a substrate is most often conducted by extraction.

In the food industry, Soxhlet extraction with ether is typically employed and the "lipophilic fraction" of a food is referred to as an "ether extract". This well known procedure is described in, for example, in "*Experimental organic chemistry: Principles and Practice*" (1996) by Harwood and Moody; Blackwell Scientific Publications, Oxford England. In the paper pulp industry extraction in Dichloromethane (DCM) is more common and the "lipophilic fraction" of wood is referred to as "DCM extractives" (ASTM D3971-89 (2010)). Determination of Ethanol extractives is also known (ASTM E1690-08).

The term "lipophilic fraction" as used in this specification and the accompanying claims refers to fatty acids and/or resin acids and/or triglycerides as well as any organic material less than 1% soluble in water at 25° C.

The lipophilic fraction may include materials that are not typically found in DCM extractives (as determined by conventional procedures), such as intermediate process products formed in steps preceding the extraction, or in the extraction in the presence of the weak acid.

In some embodiments, the lipophilic fraction includes at least 70%, 80%, 90%, or 100% of the DCM extractives present in the substrate prior to extraction. Alternatively or additionally, the lipophilic fraction may include less than 30%, 20%, 10%, 5% or substantially 0% of materials which do not belong to the DCM extractives.

Using this specification as a guide, it will be possible for a skilled practitioner to characterize the lipophilic fraction of a candidate substrate 100 using available data and/or standard analytic procedures, and adjust method 101 based upon the specific lipophilic fraction profile of the candidate substrate. According to various exemplary embodiments of the invention such adjustment can involve altering the solvent and/or weak acid employed and/or their amounts.

In general, the lipophilic fraction and/or ash in lignocellulosic substrate may not be evenly distributed. For example, in pinewood, large differences are found in extractives in the radial direction in wood stems. Pines have many more resin acids in the heartwood than in the sapwood. Heartwood also contains fewer triglycerides and more free fatty acids than the sapwood. Many extractives are incorporated deep within the cell structures and therefore may not be easily accessed and removed by the solvent during pretreatment. For these reasons, thermo-mechanical treatment 103 may contribute to extraction efficiency.

The ash fraction of substrate 100 can include inorganic cations, inorganic anions or both. Common cations present in substrate 100 include, but are not limited to, calcium, magnesium, potassium and sodium. In many cases, substrate 100 includes both calcium and magnesium and separation of these cations from the substrate may be considered a technical problem to be overcome.

Presence of ash and/or lipophilic fraction in hydrolyzate 270 and/or lignin stream 260 can cause undesirable processing complications. These complications may be associated with, for example, solvent extraction used for separation of HCl from sugars and/or lignin.

Components of the lipophilic fraction tend to accumulate in solvent used to remove HCl. Since this solvent is costly, it is often recycled. If the lipophilic fraction components are not removed, recycling is not industrially feasible. Removal of lipophilic fraction from this solvent requires costly treatment which detracts from the industrial feasibility. Alternatively or additionally, anions present in the ash can be converted to their acid form upon contact with HCl and complicate use of solvent extraction for HCl recovery. Alternatively or additionally, ash can cause difficulties for other methods of HCl separation from carbohydrates in the hydrolyzate, such as chromatographic methods. Alternatively or additionally, lipophilic fraction components can interfere with hydrolysis 250 by fouling filters and/or causing "clumping" of partially hydrolyzed wood and/or of lignin. In addition, the lipophilic fraction and/or ash tend to contaminate lignin and lower its value.

Exemplary Cost Considerations

Some exemplary embodiments of the invention contribute to a reduction in downstream processing costs of hydrolyzate 270 and/or lignin stream 260 and/or hydrolysis 250. Optionally, this contribution can be a deciding factor in whether hydrolysis 250 is economically feasible. Alternatively or additionally, this contribution can change a particular substrate from a "poor candidate" for acid hydrolysis into a "good candidate" for acid hydrolysis.

For example, removal of ash and/or lipophilic impurities from substrate 100 according to an exemplary method of the invention lowers the cost of energy and reagents required for the formation of hydrolyzate 270, for separation of the acid and for carbohydrates purification from the hydrolyzate and/or for the treatment of the lignin. Thus, according to an embodiment, at least one of the energy cost and the reagents cost for treating hydrolyzate 270 and/or treating the lignin formed from said separated extracted feed is lower by at least 2%, at least 3%, at least 5%, or at least 10% compared with that of treating hydrolyzate formed from said lignocellulosic substrate.

Exemplary Optional Alkaline Treatment

Figure 5:
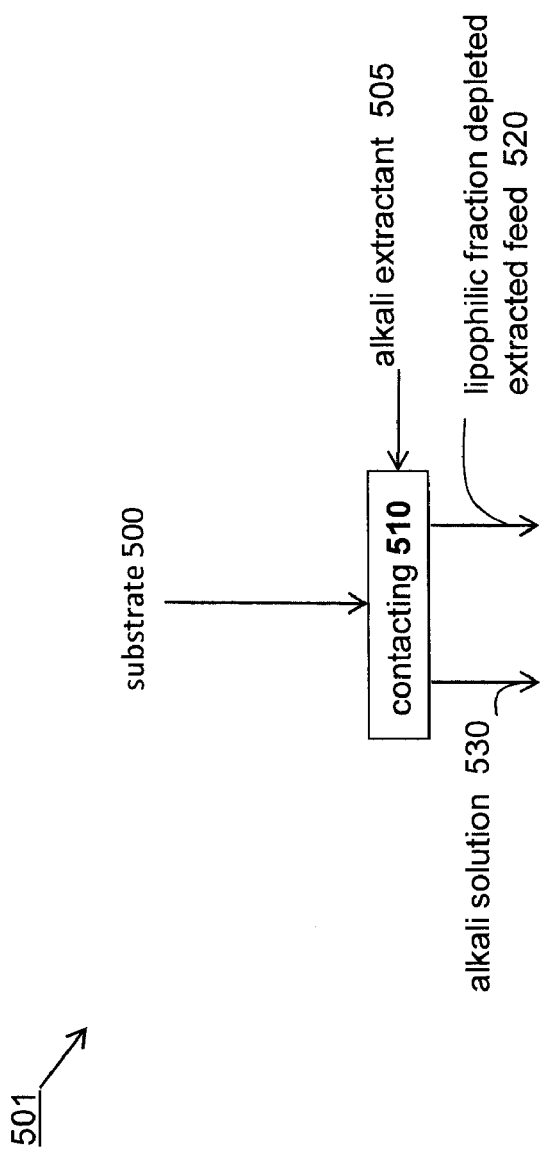
FIG. 5 is a simplified flow diagram of a method according to some exemplary embodiments of the invention.

FIG. 5 is a simplified flow diagram of a method according to some exemplary embodiments of the invention indicated generally as 501.

Depicted exemplary method 501 includes contacting 510 of a substrate 500 with an alkali extractant 505 to form a lipophilic fraction depleted extracted feed 520 and a solution comprising an alkali salt of fatty acids (alkali solution 530). According to various embodiments of the invention substrate 500 includes substrate 100 and/or extracted substrate 140 (FIG. 1). According to various exemplary embodiments of the invention extractant 505 comprises an alkali, optionally in combination with a water-soluble organic solvent.

According to some embodiments said water-soluble organic solvent includes, but is not limited to, ketones, aldehydes, esters and alcohols with up to four carbon atoms. In some embodiments, the solvent of extractant 505 is a mixture of several organic water-soluble organic solvents. In some embodiments, extractant 505 includes acetone. In some embodiments, acetone is the sole solvent in extractant 505.

Exemplary Profile Considerations

Referring again to FIG. 1: in those exemplary embodiments of the invention which involve application of a predetermined pressure-temperature-time profile (103) to substrate 100, predetermination of profile parameters can be based, for example, upon analysis of a degree of disruption of the substrate. One way to evaluate a degree of disruption of the substrate is to estimate the proportion of structural disruption occurring as a result of the treatment. Optionally, this estimation is done using microscopy, optionally electron microscopy. According to various exemplary embodiments of the invention disruption of cells and/or multicellular structures (e.g. water transporting vessels) can be evaluated.

In some embodiments, predetermination of profile parameters is based upon calculation of a severity factor which predicts the extent of the chemical degradation of the substrate. The "severity factor" of the profile is defined as:

$$\log(R) = \log\left(t * \exp\left(\frac{T - 100}{14.75}\right)\right)$$

Thus, a slight increase in temperature causes a large increase in "R" because of the exponential dependency. However, different lignocellulosic substrates respond differently to treatment with high pressure steam so that this formula is informative only with regard to changes in profile for a same substrate. In some embodiments, the predetermined pressure-temperature-time profile is characterized by severity factor of at least 3, 3.2, 3.4, 3.6, 3.8, or at least 4.0. Alternatively or additionally, in some embodiments, the predetermined pressure-temperature-time profile is characterized by severity factor of less than 5, 4.8, 4.6, 4.4, or even less than 4.2.

In some embodiments, the predetermined pressure-temperature-time profile is characterized by severity factor in the range of 3.4 to 4.2; the range of 3.6 to 4.0. In some embodiments, the severity factor is about 3.8. In some exemplary embodiments of the invention, the predetermined pressure-temperature-time profile is selected so that at least 10%, optionally at least 20%, optionally at least 30%, optionally at least 40% of cells or intermediate or greater proportions of cells are disrupted. In some embodiments, the predetermined pressure-temperature-time is selected so that at least 10%, at least 20%, at least 30%, at least 40% of multicellular structures or intermediate or greater proportions of multicellular structures are disrupted. According to various embodiments of the invention temperatures applied in the predetermined pressure-temperature-time profile can be greater than 150°, 160°, 170°, 180°, 190° C. or intermediate or higher temperatures. In some embodiments, temperatures applied in the predetermined pressure-temperature-time profile can be less than 250°, less than 240°, less than 230°, less than 220°, less than 210° C. or intermediate or lower temperatures. According to various embodiments of the invention temperatures applied in the predetermined pressure-temperature-time profile can be in the range of 150° to 250° C., 160° to 240° C., 170° C. to 230° C., 180° to 220° C., 190° to 210° C., or intermediate ranges. According to various embodiments of the invention the time for which the predetermined pressure-temperature-time profile is applied can be greater than 0.1, greater than 0.2, greater than 0.3, greater 0.4 minutes or intermediate or greater times. In some embodiments, the time for which the predetermined pressure-temperature-time profile is applied is less than 10, less than 6, less than 3, less than 2 minutes, or intermediate or lesser times. According to various exemplary embodiments of the invention the time for which the predetermined pressure-temperature-time profile is applied is in the range of 0.1 to 10.0, 0.2 to 6.0, 0.3 to 3.0 or 0.4 to 2.0, minutes or intermediate ranges. In some embodiments, the pressure applied during the predetermined pressure-temperature-time profile is at least 6, at least 8, at least 10, at least 12, at least 14, at least 15, at least 16 bar or intermediate or greater pressures. Optionally, quantitative analysis of an achieved degree of disruption from an initial applied profile on a given substrate can lead to a conclusion the profile is "too strong" or "not strong enough". The formula given above provides a rationale for how to adjust the profile to be "stronger" or "less strong" and allows the practitioner to evaluate in advance what magnitude of adjustment may be appropriate.

Exemplary Hydrolysis Considerations

Referring again to FIG. 1: according to various embodiments of the invention an extractant 110 including a weak acid is employed at extracting 120. In some exemplary embodiments of the invention, control is exercised over an amount of hydrolysis of cellulose and/or hemicellulose resulting from contact of this weak acid with the substrate. In some embodiments, the weak acid in extractant 110 hydrolyzes less than less than 10%, less than 8%, less than 5%, less than 3%, less than 1%, less than 0.5% or intermediate or lesser percentages, of cellulose in the substrate during extracting 120 before miscella 130 is removed.

Alternatively or additionally, in some embodiments, the weak acid in extractant 110 hydrolyzes less than less than 10%, less than 8%, less than 5%, less than 3%, less than 1%, less than 0.5%, or intermediate or lesser percentages of hemicellulose in the substrate during extracting 120 before miscella 130 is removed.

Exemplary Filtration Considerations

Figure 8:
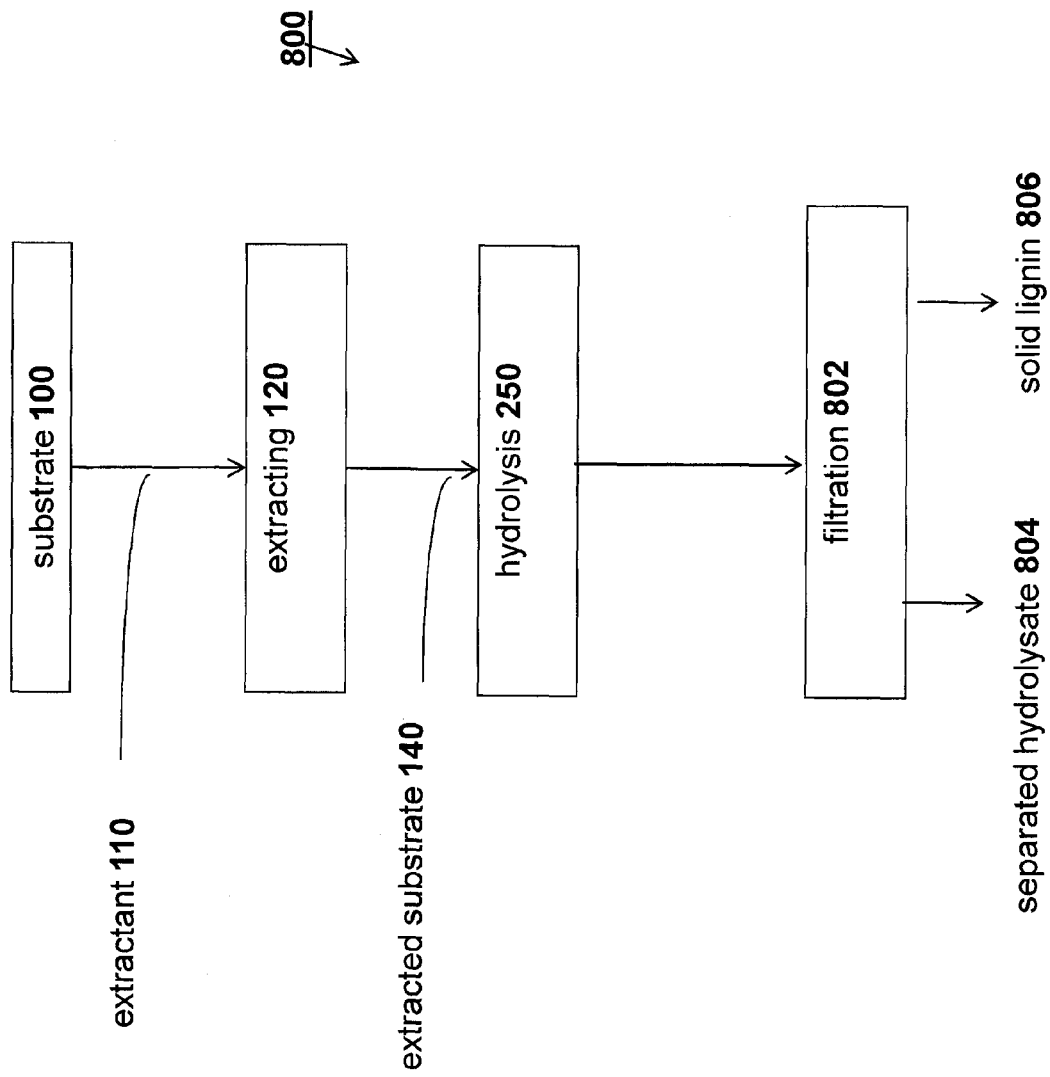
FIG. 8 is a simplified flow diagram of a method according to some exemplary embodiments of the invention.

FIG. 8 is a simplified flow diagram of a method according to another exemplary embodiment of the invention depicted generally as 800. Depicted exemplary method 800 includes extracting 120 lignocellulosic substrate 100 with an extractant 110 comprising a water-soluble organic solvent to form an extracted substrate 140.

According to depicted exemplary method 800, extracted substrate 140 is hydrolyzed 250 to form hydrolyzate 260 (See FIG. 1) and a residual lignin stream 270. Residual lignin stream 270 includes solid lignin, depicted here as 806. According to exemplary method 800, hydrolyzate 260 is separated by filtration 802, to obtain separated hydrolyzate 804 and separated solid lignin 806. Following filtration 802, separated hydrolyzate 804 contains less than 2, less than 1, less than 0.5, or less than 0.1% solids. In some embodiments of method 800 extraction 120 contributes to an increase in filtration rate relative to a filtration rate obtained by hydrolyzing substrate 100 without extracting 120, using an identical filter and identical filtration conditions. Optionally, the filtration rate is faster by at least 10%, by at least 25%, by at least 40%, by at least 50%, or intermediate or greater percentages. In some embodiments, each of separated hydrolyzate 804 and solid lignin 806 is subjected to appropriate downstream processing. Alternatively or additionally, in some exemplary embodiments, a predetermined-pressure-temperature-time profile is applied to substrate 100 prior to extracting 120 as described hereinabove in the context of FIG. 1.

In some embodiments, a substrate of the invention is pine wood chips. The pine wood chips are subjected to a thermo-mechanical treatment of steam explosion (e.g. with a severity factor of about 3.8). The broken down wood chips are then subjected to extracting by an extractant acetone, 0.005% to 0.01% acetic acid, and water. Miscellae or a miscelle layer which includes the extractant and various impurities from the pine wood is removed. The extractant from the miscelle is regenerated using any method described herein. The extracted substrate which is primarily cellulose, hemicelluloses and lignin is dried and subsequently hydrolyzed. Hydrolysis can occur, e.g., in 42% HCl/(HCL+water) to produce a hydrolyzate stream and lignin stream. The hydrolyzate comprises sugars which are used to make commercial products as varied as xylose and industrial polymers and enzymes made by growing organisms using the sugars. The lignin stream is also used to make commercial products.

Exemplary Downstream Processing

Figure 6A:
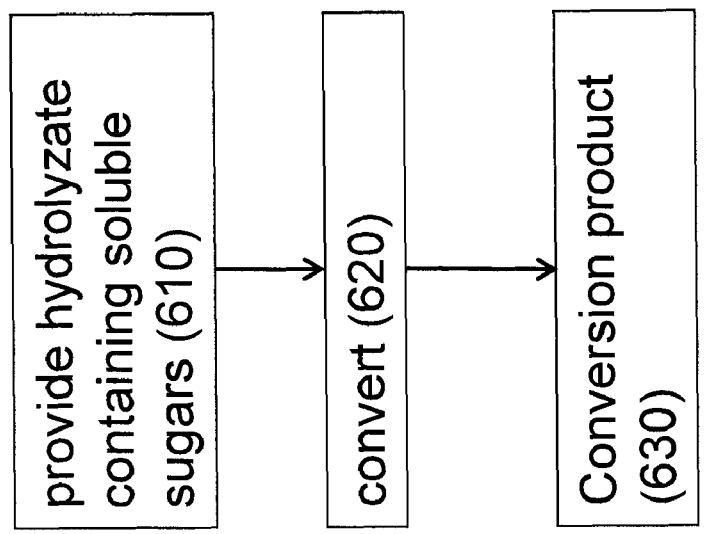
FIGS. 6a and 6b are simplified flow diagrams of methods according to some exemplary embodiments of the invention.

FIG. 6a is a simplified flow diagram of a method according to another exemplary embodiment of the invention depicted generally as 600. Depicted exemplary method 600 includes providing 610 a hydrolyzate (e.g. 270) containing soluble sugars as described above and converting 620 at least a portion of the sugars to a conversion product 630.

Figure 6B:
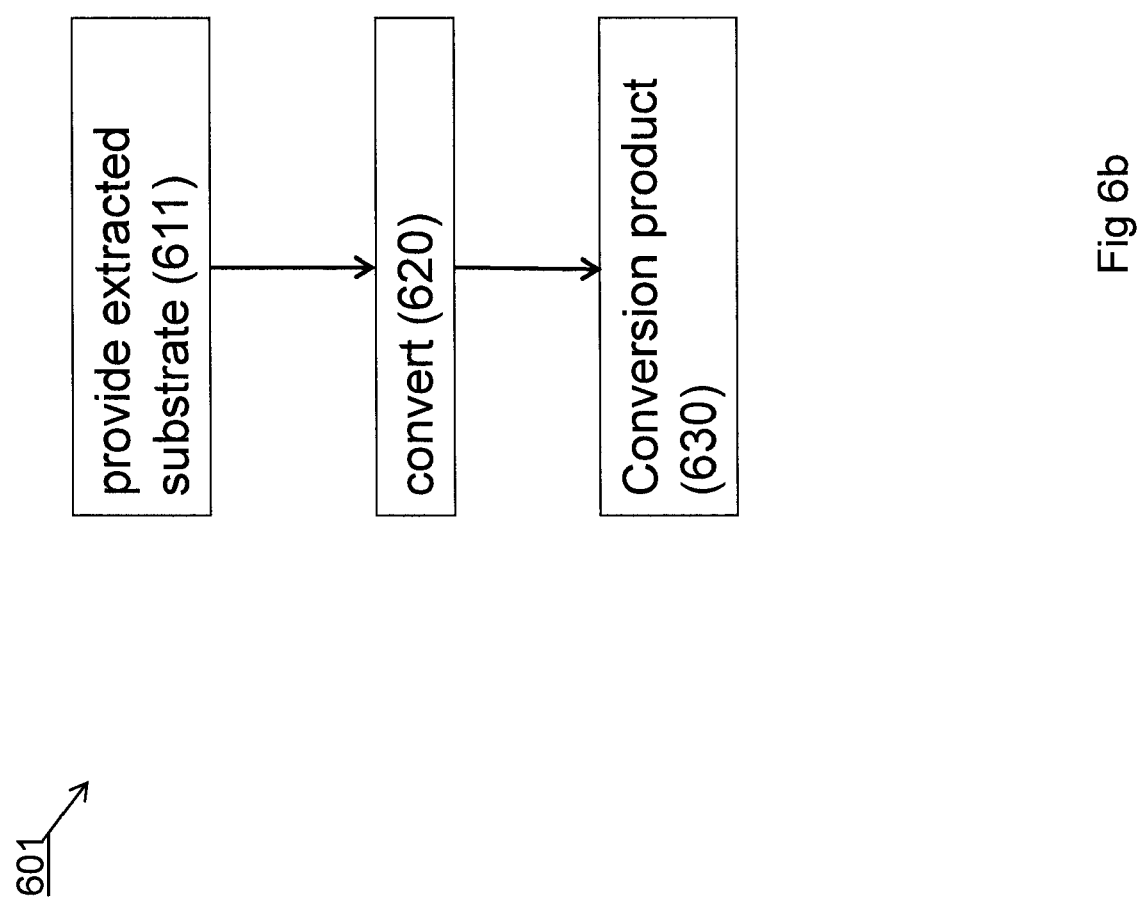

FIG. 6b is a simplified flow diagram of a method according to another exemplary embodiment of the invention depicted generally as 601. Depicted exemplary method 601 includes providing 611 an extracted substrate (e.g. 140 or 230) as described above and converting 620 at least a portion of the sugars to a conversion product 630.

According to various exemplary embodiments of the invention, conversion 620 includes at least one of fermentation (aerobic and/or anaerobic fermentation), a thermal process involving exposure to temperatures in excess of 200° C., chemical conversion, enzymatic conversion, electrolytic reduction, catalytic hydrogenation, and isomerization.

For embodiments comprising fermentation, the fermentation process may employ a genetically modified organism (GMO). A wide range of GMOs are potentially compatible with sugars produced by the methods described herein. GMOs may include, but are not limited to, members of the genera *Clostridium, Escherichia, Salmonella, Zymomonas, Rhodococcus, Pseudomonas, Bacillus, Enterococcus, Alcaligenes, Lactobacillus, Klebsiella, Paenibacillus, Corynebacterium, Brevibacterium, Pichia, Candida, Hansenula* and *Saccharomyces*. Hosts that may be particularly of interest include: Oligotrophacarboxidovorans, *Escherichia coli, Bacillus licheniformis, Paenibacillusmacerans, Rhodococcuserythropolis, Pseudomonas putida, Lactobacillus plantarum, Enterococcus faecium, Enterococcus gallinarium, Enterococcus faecalis, Bacillus subtilis* and *Saccharomyces cerevisiae*. Also, any of the known strains of these species may be utilized as a starting microorganism. In various exemplary embodiments, the microorganism is an actinomycete selected from *Streptomyces coelicolor, Streptomyces lividans, Streptomyces hygroscopicus*, or *Saccharopolysporaerytlzraea*. In various exemplary embodiments, the microorganism is aneubacterium selected from *Escherichia coli, Pseudomonas flucrescens, Pseudomonas putida, Pseudomonas aeruginosa, Bacillus subtilis*, or *Bacillus cereus*.

In some exemplary embodiments, the GMO is a gram-negative bacterium. In some exemplary embodiments, the recombinant microorganism is selected from the genera *Zymomonas, Escherichia, Alcaligenes*, and *Klebsiella*. In some exemplary embodiments, the recombinant microorganism is selected from the species *Escherichia coli, Cupriavidus necator*, and *Oligotropha carboxidovorans*. In some exemplary embodiments, the recombinant microorganism is an *E. coli* strain.

In some exemplary embodiments of the invention, conversion product 630 may comprise lactic acid. The potential of lactic acid as a commodity chemical, for example for use in the production of various industrial polymers, is known and has been described in for example, U.S. Pat. Nos. 5,142,023; 5,247,058; 5,258,488; 5,357,035; 5,338,822; 5,446,123; 5,539,081; 5,525,706; 5,475,080; 5,359,026; 5,484,881; 5,585,191; 5,536,807; 5,247,059; 5,274,073; 5,510,526; and 5,594,095. (The complete disclosures of these seventeen patents, are incorporated herein by reference.)

Various exemplary embodiments of conversion processes 620 including fermentation and/or chemical processes which are described in U.S. Pat. No. 7,629,010; U.S. Pat. No. 6,833,149; U.S. Pat. No. 6,610,867;U.S. Pat. No. 6,452,051; U.S. Pat. No. 6,229,046; U.S. Pat. No. 6,207,209; U.S. Pat. No. 5,959,128; U.S. Pat. No. 5,859,270; U.S. Pat. No. 5,847,238; U.S. Pat. No. 5,602,286; and U.S. Pat. No. 5,357,035, the contents of which are incorporated herein by reference for all purposes. According to various exemplary embodiments of the invention sugars present the hydrolyzate provided at 610 are incorporated into a fermentation product as described in the following U.S. patents, the contents of each of which are hereby incorporated by reference: U.S. Pat. No. 7,678,768; U.S. Pat. No. 7,534,597; U.S. Pat. No. 7,186,856; U.S. Pat. No. 7,144,977; U.S. Pat. No. 7,019,170; U.S. Pat. No. 6,693,188; U.S. Pat. No. 6,534,679; U.S. Pat. No. 6,452,051; U.S. Pat. No. 6,361,990; U.S. Pat. No. 6,320,077; U.S. Pat. No. 6,229,046; U.S. Pat. No. 6,187,951; U.S. Pat. No. 6,160,173; U.S. Pat. No. 6,087,532; U.S. Pat. No. 5,892,109; U.S. Pat. No. 5,780,678; and U.S. Pat. No. 5,510,526, the contents of which are incorporated herein by reference for all purposes. Alternatively or additionally, conversion product 630 can be, for example, an alcohol, carboxylic acid, amino acid, methane, or monomer for the polymer industry or a protein. According to various exemplary embodiments of the invention the protein can be provided in the form of one or more enzymes, feed proteins, food proteins and protein-rich microorganisms ("single-cell proteins").

In some exemplary embodiments of the invention, conversion product 630 is a final product which is used "as is" as a consumer product. In other exemplary embodiments of the invention, conversion product 630 serves as an ingredient in a final product which is used by an industry and/or by individuals. In other embodiments of the invention, conversion product 630 is subject to one or more additional rounds of conversion (not depicted) to produce a consumer product. According to various embodiments of the invention a consumer product may be selected from the group consisting of a detergent, a polyethylene-based product, a polypropylene-based product, a polyolefin-based product, a polylactic acid (polylactide)-based product, a polyhydroxyalkanoate-based product and a polyacrylic-based product. Optionally, the detergent includes a sugar-based surfactant, a fatty acid-based surfactant, a fatty alcohol-based surfactant, or a cell-culture derived enzyme.

Optionally, the polyacrylic-based product is a plastic, a floor polish, a carpet, a paint, a coating, an adhesive, a dispersion, a flocculant, an elastomer, an acrylic glass, an absorbent article, an incontinence pad, a sanitary napkins, a feminine hygiene product, and a diaper.

Optionally, the polyolefin-based product is a milk jug, a detergent bottle, a margarine tub, a garbage container, a plumbing pipe, an absorbent article, a diaper, anon woven, an HDPE toys or an HDPE detergent packaging.

Optionally, the polypropylene based product is an absorbent article, a diaper or a non woven. Optionally, the polylactic acid based product is a packaging of an agriculture product or of a dairy product, a plastic bottle, a biodegradable product or a disposable.

Optionally, the polyhydroxyalkanoate based product is packaging of an agriculture product, a plastic bottle, a coated paper, a molded or extruded article, a feminine hygiene product, a tampon applicators, an absorbent article, a disposable nonwoven or wipe, a medical surgical garment, an adhesive, an elastomer, a film, a coating, an aqueous dispersant, a fiber, an intermediate of a pharmaceutical or a binder.

Optionally, conversion product 630 is ethanol, butanol, isobutanol, a fatty acid, a fatty acid ester, a fatty alcohol or biodiesel.

In some embodiments of the invention, method 700 includes processing of conversion product 630 to produce at least one product such as, for example, an isobutene condensation product, jet fuel, gasoline, gasohol, diesel fuel, drop-in fuel, diesel fuel additive, or a precursor thereof. Optionally, the gasahol is ethanol-enriched gasoline and/or butanol-enriched gasoline.

In some embodiments of the invention, the product produced from conversion product 630 is diesel fuel, gasoline, jet fuel or a drop-in fuel. Various exemplary embodiments of the invention include consumer products, precursors of consumer product, and ingredients of consumer products produced from conversion product 630.

Optionally, the consumer product, precursor of a consumer product, or ingredient of a consumer product includes at least one conversion product 630 such as, for example, a carboxylic or fatty acid, a dicarboxylic acids, a hydroxylcarboxylic acids, a hydroxyl di-carboxylic acid, a hydroxyl-fatty acid, methylglyoxal, mono-, di-, or poly-alcohol, an alkane, an alkene, an aromatic, an aldehyde, a ketone, an ester, a biopolymer, a protein, a peptide, an amino acid, a vitamin, an antibiotics, and a pharmaceutical. For example, the product may be ethanol-enriched gasoline, jet fuel, or biodiesel.

Optionally, the consumer product has a ratio of carbon-14 to carbon-12 of about $2.0 \times 10^{-13}$ or greater.

According to various embodiments of the invention, the consumer product includes an ingredient of a consumer product as described above and an additional ingredient produced from a raw material other than lignocellulosic material. In some exemplary embodiments of the invention, the ingredient and the additional ingredient produced from a raw material other than lignocellulosic material are essentially of the same chemical composition.

In some embodiments, the consumer product includes a marker molecule at a concentration of at least 100 ppb.

According to various embodiments of the invention the marker molecule can be, for example, furfural, hydroxy-methyl furfural, products of furfural or hydroxy-methylfurfural condensation, color compounds derived from sugar caramelization, levulinic acid, acetic acid, methanol, galacturonic acid, or glycerol.

Exemplary Extracted Substrates

An additional aspect of some embodiments of the invention relates to extracted pine wood. According to various exemplary embodiments, the extracted wood comprises at least 35%, at least 40%, at least 45%, at least 50% cellulose or intermediate or greater percentages on a dry weight basis. According to various exemplary embodiments, the extracted wood comprises at least 7.4%, at least 8%, at least 8.5%, at least 9% hemicelluloses or intermediate or greater percentages on a dry weight basis. According to various exemplary embodiments, the extracted wood comprises less than 1.0%, less than 0.7%, less than 0.6%, less than 0.4%, less than 0.3% ash or intermediate or lesser percentages on a dry weight basis. In some embodiments, the extracted wood comprises less than 2%, less than 1.5%, less than 1% or intermediate or lesser percentages of DCM extractives on a dry weight basis. In some embodiments, the extracted wood comprises less than 50%, less than 30%, less than 20%, less than 10% or intermediate or lesser percentages of the moisture content of said pine wood prior to extraction. In some embodiments, at least 10%, at least 20%, at least 30%, at least 40% or intermediate or higher percentages of the cells are disrupted. In some embodiments, the extracted wood comprises acetone and/or a weak acid.

Exemplary Extraction Mixtures

An additional aspect of some embodiments of the invention relates to an extraction mixture. The extraction mixture comprises one part lignocellulosic substrate and at least 2 parts, and/or less than 3 parts, acetone, on a weight basis. In some embodiments, the extraction mixture includes a weak acid, such as acetic acid and/or sulfurous acid. In some embodiments, the extraction mixture includes added water.

Exemplary Advantages

Practice of various methods described hereinabove can influence the composition of hydrolyzate 270 (FIG. 3). Specifically, impurities removed in miscella 130 will not be present in hydrolyzate 270.

While it is possible to remove these impurities from hydrolyzate 270 after its formation, it can be advantageous to be spared such a post-hydrolysis removal. Advantages may be related to complexity of industrial processes and/or costs.

Referring again to FIG. 3: in general, these advantages stem from the fact that the ratio of soluble sugars to all hydrolyzate components other than water and HCl will tend to be higher in a hydrolyzate 270 produced in a system with an extraction module 310 and/or disruption module 340 than a comparable hydrolyzate produced in a system which does not include such modules.

In some embodiments, implementation of a disruption module 340 in conjunction with extraction module 310 provides an incremental advantage relative to use of extraction module 310 without disruption module 340 in terms of the ratio of soluble sugars to all hydrolyzate components other than water and HCl in hydrolyzate 270.

Alternatively or additionally, increasing the ratio of soluble sugars to all hydrolyzate components other than water and HCl can improve materials flow in hydrolysis module 320 and/or an exit therefrom and/or downstream processing equipment (not depicted). In some embodiments, this improvement in materials flow can be related changes in viscosity of a liquid phase of hydrolyzate 270 and/or behavior of un-dissolved solids (e.g. lignin) in the hydrolyzate. These improvements in materials flow may be most easily observable in system components such as filters, drains and pumps.

Alternatively or additionally, lignin present in hydrolyzate 270 will not have impurities removed in miscella 130 associated with it. Again, while it is possible to remove these impurities from lignin after its separation from hydrolyzate 270, it can be advantageous to be spared such a post hydrolysis removal. As with sugars, advantages may be related to complexity of industrial processes and/or costs. With regard to lignin, impurities such as DCM extractives and ash (e.g. sulfates and phosphates) are particularly relevant.

Additional Exemplary Advantages

Referring again to FIG. 1: removal of miscella 130 has been described above in terms of how it improves a filtration rate of lignin from hydrolyzate 270. Alternatively or additionally, implementation of extracting 120 with extractant 110 to separate miscella 130 and/or 240 from the substrate can make one or more other improvements to downstream processing of extracted substrate 140 and/or 230 and/or hydrolyzate 270.

In some embodiments, extracting 120 contributes to a reduction in a rate of fouling of filters of lignin by 10%, 20%, 30%, 40% or even 50% or more. Alternatively or additionally, in some embodiments, extracting 120 contributes to a reduction in a rate of fouling of resin used in chromatographic-separation of sugars in hydrolyzate 270 by 10%, 20%, 30%, 40% or even 50% or more. Exemplary chromatographic resins and their use in sugar separation are described on co-pending applications IL 211093 and U.S. 61/524,839; each of which is fully incorporated herein by reference. Alternatively or additionally, in some embodiments, extracting 120 contributes to a reduction in a rate of fouling of filters used to filter undefined particulate matter from hydrolyzate 270 by 10%, 20%, 30%, 40% or even 50% or more. Alternatively or additionally, in some embodiments, extracting 120 contributes to a reduction in a rate of clogging of nozzles used in a thermal process (e.g. pyrolysis and/or gasification) and/or in reactive fluid treatment by 10%, 20%, 30%, 40% or even 50% or more.

Alternatively or additionally, in some embodiments, extracting 120 contributes to a reduction in amount of solids filtered by various filters in the system by 10%, 20%, 30%, 40% or even 50% or more.

Alternatively or additionally, in some embodiments, extracting 120 contributes to a reduction in clumping of lignin in lignin stream 260 by 10%, 20%, 30%, 40% or even 50% or more.

Exemplary Method Described in Detail

Referring again to FIG. 1: In some embodiments, substrate 100 is provided as pine wood chips and thermo-mechanical treatment 103 includes steam explosion (e.g. with a severity factor of about 3.8). In some embodiments, extracting 120 employs an extractant 110 including acetone and 0.005% to 0.01% by weight of acetic acid in a mixture with water. Miscellae 130 and/or 240 are removed and extractant 110 is regenerated from them as described hereinabove. Following drying 221, dried extracted substrate 230 is hydrolyzed 250 in 42% HCl/(HCL+water) by weight to produce hydrolyzate 270 and lignin stream 260.

Exemplary Compositions

In some embodiments of the invention, there is provided a lignocellulosic composition including (on a dry matter basis) cellulose, hemicellulose, lignin and characterized by one or more of the following characteristics.

In some embodiments, the composition is characterized by less than 5,000 PPM, less than 3,000 PPM, less than 2,000 PPM, less than 1,000 PPM, or less than 500 PPM lipophilic material.

Alternatively or additionally, in some embodiments, the composition is characterized by less than 5,000 PPM, optionally less than 3,000 PPM, optionally less than 2,000 PPM, optionally less than 1,000 PPM, optionally less than 500 PPM ash.

Alternatively or additionally, in some embodiments, the composition is characterized by less than 2,000 PPM, less than 1,500 PPM, less than 1,000 PPM, or less than 500 PPM Calcium.

Alternatively or additionally, in some embodiments, the composition is characterized by less than 10,000 PPM, less than 8,000 PPM, less than 6,000 PPM, less than 4,000 PPM, less than 2,000 PPM, or less than 1,000 PPM pectin. Alternatively or additionally, in some embodiments, the composition is characterized by less than 2,000 PPM, optionally less than 1,500 PPM, optionally less than 1,000 PPM, optionally less than 500 PPM furfural. Alternatively or additionally, the composition is characterized by at least 10 PPM marker selected from the group consisting of: furfural, organically-bound sulfur, and a water soluble solvent (e.g. acetone).

Alternatively or additionally, the composition is characterized by a moisture content of 5% to 30%, 8% to 25%, or 10% to 20%.

According to various exemplary embodiments of the invention the composition is characterized by at least two, at least three, at least four, or at least five of the characteristics set forth above.

Figure 9:
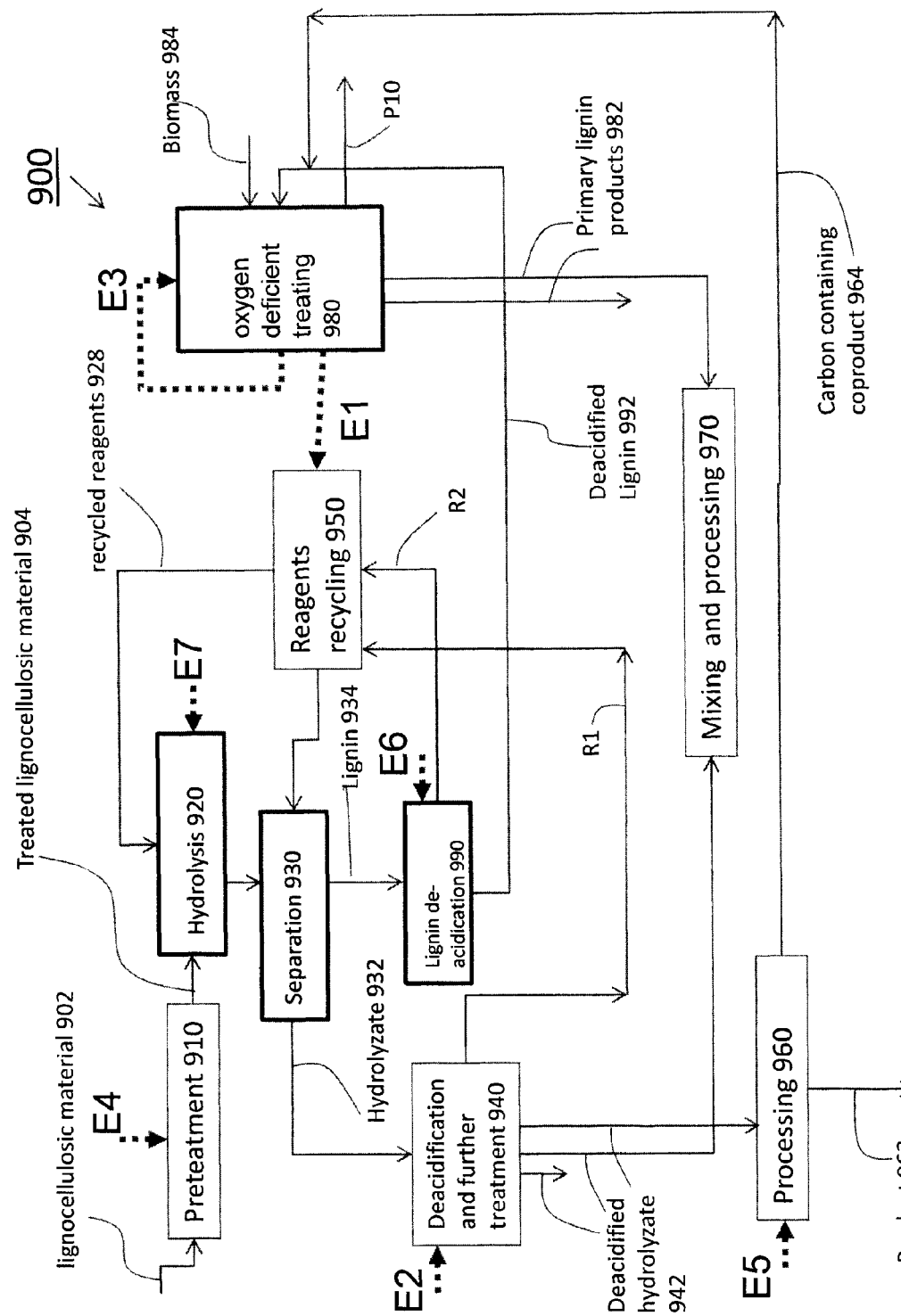
FIG. 9 is a simplified flow diagram of a method according to some exemplary embodiments of the invention.

FIG. 9 depicts an exemplary method for processing a lignocellulosic material according to some embodiments of the invention indicated generally as 900. Depicted exemplary method 900 includes providing a lignocellulosic feed material 902 comprising at least one polysaccharide and lignin. Any lignocellulosic material is suitable. According to various exemplary embodiments of the invention lignocellulosic material 902 is selected from the group consisting of wood, sugarcane bagasse, oil palm biomass, agricultural residues, biomass crops or recycled biomass. In some embodiments, providing lignocellulosic material 902 includes pretreatment 910. Optionally, pretreatment 910 includes comminuting and/or desolventizing. In some embodiments, excess heat E4 from the pyrolysis described hereinbelow provides energy for pretreatment 910.

In the depicted embodiment treated lignocellulosic material 904 is hydrolyzed 920 so that at least a fraction of the polysaccharide is converted to an acidic (e.g. HCl) hydrolyzate 932 which is separated 930 from lignin stream 934.

Hydrolyzate 932 includes at least one carbohydrate and HCl and lignin stream 934 includes solid lignin, HCl and water. In some embodiments, the hydrolysis medium is formed by contacting lignocellulosic material 902 with a recycled reagent HCl stream (recycled reagents 928). In an embodiment, the HCl concentration in the hydrolysis medium is in the range between 25% and 50% wt, as calculated by HCl weight divided by the combined weights of HCl and water multiplied by 100. In some embodiments, the HCl concentration in the hydrolysis medium is in the range between 35% and 38% wt or between 30% and 36% wt.

In some embodiments, hydrolysis 920 is not performed to its full extent; leaving a significant ratio of the polysaccharides in insoluble state. In some embodiments, the lignin stream comprises residual insoluble polysaccharide and the residual insoluble polysaccharides constitute at least 5% of the insoluble polysaccharide in lignocellulosic material 902, at least 10%. Alternatively or additionally, the residual insoluble polysaccharides constitute less than 30% of the insoluble polysaccharide in lignocellulosic material 902, optionally less than 20%. In some embodiments, at least 50% of the residual insoluble polysaccharide is crystalline, optionally at least 70% or even at least 90%. Different parts of the polysaccharide composition of lignocellulosic material 902 hydrolyze at different rates. In some embodiments, the residual insoluble polysaccharide is mainly cellulose, optionally more than 80% cellulose. In some cases, the cellulose of the residual insoluble polysaccharide differs from the cellulose in the lignocellulosic feed, e.g. in its average molecular weight and/or in its degree of crystallinity.

According to various exemplary embodiments of the invention relaxing the requirements for the extent of hydrolyzation of the polysaccharides contained in lignocellulosic material 902 allows the use of lower acid concentration in the hydrolysis medium, which in turn reduces the costs of handing and recycling of the acid and optionally reduces the required residence time of lignocellulosic material 902 in contact with the hydrolysis medium, enabling higher throughput for a fixed size facility.

The depicted embodiment includes separating 930 hydrolyzate 932 from lignin stream 934. Any method of separating is suitable. According to an embodiment, separating 930 includes filtration and/or centrifugation.

The depicted embodiment includes de-acidifying 940 and optionally further treating hydrolyzate 932 to form a de-acidified, carbohydrate-comprising hydrolyzate 942 and recovered reagent R1. In some embodiments, HCl and water are separated from separated hydrolyzate 932 to form acid-depleted hydrolyzate 942 and recovered acid in a process comprising at least one of extraction with an S1 solvent and distillation.

As used in this specification and the accompanying claims the term "S1 solvent" or "S1" indicates an organic solvent with a solubility in water of less than 15% wt, optionally less than 5% wt, optionally less than 2% wt and optionally less than 1% wt. Alternatively or additionally, the solubility of water in S1 is less than 20% wt, optionally less than 15% wt, optionally less than 10% wt and optionally less than 8% wt. S1 is further characterized by at least one of: (1) having a delta-P between 5 and 10 $MPa^{1/2}$, optionally between 6 and 9 $MPa^{1/2}$ and optionally between 6.5 and 8.5 $MPa^{1/2}$ and (b) having a delta-H between 5 and 20 $MPa^{1/2}$, optionally between 6 and 16 $MPa^{1/2}$ and optionally between 8 and 14 $MPa^{1/2}$, wherein delta-P is the polarity related component of Hoy's cohesion parameter and delta-H is the hydrogen bonding related component of Hoy's cohesion parameter.

According to various exemplary embodiments of the invention the boiling point of S1 is greater than that of water, optionally greater than 120° C. at atmospheric pressure, optionally greater than 140° C., and optionally greater than 160° C. Alternatively or additionally, the boiling point of S1 is lower than 250° C. at atmospheric pressure, optionally lower than 220° C., and optionally lower than 200° C.

In some embodiments, S1 forms a heterogeneous azeotrope with water. In some embodiments, in the heterogeneous azeotrope with water, the ratio of S1 to water is in the range between 50 and 0.02 weight/weight, between 5 and 0.2, between 4 and 0.25, between 3 and 0.3, or between 2 and 0.5. According to an embodiment, the boiling point of the heterogeneous azeotrope at atmospheric pressure is less than 100° C.

For example, S1 may be selected from the group consisting of aliphatic or aromatic alcohols, ketones and aldehydes having at least 5 carbon atoms, e.g. various pentanols, hexanols, heptanols, octanols, nonanols, decanols, methyl-isobutyl-ketone and methyl-butyl-ketone and combinations thereof. As used herein, the term alcohols means any of mono-, di- and poly-alcohols, primary, secondary and tertiary ones, straight chain and branched alcohols and any combination of those. In some embodiments, S1 is selected from hexanol and 2-ethyl-1-hexanol and mixtures thereof.

In some embodiments, the recovered acid (part of R1) is optionally treated by mixing with at least one other acid-comprising stream (e.g. R2) and/or concentration (reagents recycling 950) to form recycled reagents 928. According to an embodiment excess heat E2 from the pyrolysis described herein provides at least part of the energy for the energy requirement for de-acidification 940 and further treatment.

According to an embodiment said acid depleted hydrolyzate is further treated to form the de-acidified, carbohydrate-containing hydrolyzate. According to an embodiment said treating of said de-acidified hydrolyzate comprises at least one of extraction with an organic solvent and chromatographic separation.

In some embodiments, formation of the de-acidified hydrolyzate includes removal of dissolved solvent and/or active carbon treatment and/or ion-exchange treatment and/or concentration.

In some embodiments, excess heat E2 from the pyrolysis step described herein provides energy for formation of de-acidified hydrolyzate 942.

In some embodiments, the depicted method includes processing 960 of de-acidified hydrolyzate 942 into at least one hydrolyzate product 962. In some embodiments, processing 960 includes fractioning and/or separating and/or purifying carbohydrates, and/or hydrolyzing oligomers and/or chemical conversion or biological conversion of carbohydrates in hydrolyzate 942 to form a product comprising medium and/or product recovery from the medium and/or product purification. In some embodiments, processing 960 includes fermenting carbohydrates in de-acidified hydrolyzate 942 to form product 962 in fermentation broth, separating the product from the fermentation broth and purifying said product. According to various exemplary embodiments of the invention product 962 is selected from the group consisting of ethanol, butanol, other alcohols, amino acids, carboxylic acids and monomers for the polymer industry. In some embodiments, excess heat E5 from the pyrolysis step provides energy for processing 960.

In some embodiments, the depicted method includes de-acidifying 990 lignin stream 934 to form de-acidified lignin 992 and a second recovered acid stream R2. In some embodiments, lignin de-acidification 990 includes contacting with a solvent and/or distillation. In some embodiments, lignin de-acidification 990 includes contacting with an S1 solvent or a similar solvent followed by desolventization.

In some embodiments, an HCl to lignin weight ratio in de-acidified lignin 992 is less than 0.01, less than 0.005 or less than 0.002. Alternatively or additionally, de-acidified lignin 992 is a solid composition including primarily lignin. In some embodiments, preferably at least 60%, or even at least 80% of de-acidified lignin 992 is lignin. In some embodiments, de-acidified lignin 992 includes residual insoluble polysaccharide.

In some embodiments, lignocellulosic material 902 includes extractives. As used in the context of material 902, the term "extractives" includes tall oil, resin acids, fatty acids, triglycerides and volatile organic compounds. In some embodiments, de-acidified lignin 992 comprises at least 50% of the extractives from lignocellulosic material 902, optionally at least 70%.

In some embodiments, second recovered acid stream R2 in FIG. 9 is further treated in reagents recycling 950 to form recovered acid (part of recycled reagents 928).

Alternatively or additionally, in some embodiments, excess heat from the pyrolysis step described herein provides energy (E6 and E1 respectively) lignin de-acidification 990 and/or reagents recycling 950.

In some embodiments, method 900 includes treating de-acidified lignin 992 at an elevated temperature (e.g. by pyrolysis), in an oxygen-deficient atmosphere (oxygen deficient treating 980) to form at least one primary lignin product 982 and optionally converting said primary lignin product to at least one secondary lignin product P10 and producing excess heat (E1, E2, E3, E4, E5, E6 and E7). According to various exemplary embodiments of the invention treating 980 includes pyrolysis and/or gasification. In some embodiments, primary lignin product 982 is selected from the group consisting of biocrude, hydrogen, carbon mono-oxide and carbon dioxide.

Since pyrolysis is exthothermic, heat is produced treating 980 de-acidified lignin 992. Heat energy so produced can be used directly and/or converted to electricity.

In some embodiments, de-acidified lignin 992 is combined with additional biomass 984 in treating 980.

In some embodiments, primary lignin product 982, optionally combined with additional biomass 984, is converted into at least one secondary lignin product P10. In some embodiments, the converting includes at least one of chemically catalyzed conversion and biocatalyzed conversion. In some embodiments, the biocatalyzed conversion includes fermentation of the primary lignin products as such or after some adjustment.

In some embodiments, secondary lignin product P10 is selected from the group consisting of ethanol, butanol, other alcohols, amino acids, carboxylic acids and monomers for the polymer industry.

In some embodiments of method 900, the carbon contents of lignocellulosic material 902, of de-acidified hydrolyzate 942 and of primary lignin products 982 are M1, M2 and M3, respectively, and (M2+M3)/M1 is greater than 0.85, optionally greater than 0.90 and optionally greater than 0.95.

In some embodiments, the depicted method, includes mixing and processing 970 at least a fraction of de-acidified hydrolyzate 941 with at least a fraction of primary lignin product(s) 982 together. In some embodiments, primary lignin product 982 provides a carbon source for fermentation and it is combined with hydrolyzate 942 to form a combined fermentation carbon source mixture.

Alternatively or additionally, method 900 includes reacting or combining hydrolyzate product 962 with at least one of primary lignin product 982 and secondary lignin product P10. In some embodiments, the hydrolyzate product is a bio-fuel, and the lignin product is bio-crude and at least a fraction of the bio-fuel is combined with at least a fraction of the bio-crude to form a mixed fuel. Alternatively or additionally, the hydrolyzate product is acetic acid and the lignin product is hydrogen, and the acetic acid is reacted with the hydrogen to form ethanol. Alternatively or additionally, the hydrolyzate product or a product thereof includes a double bond, e.g. an alkene formed from an alcohol, the lignin product is hydrogen and the alkene is reacted with said hydrogen to form an alkane.

In some embodiments, processing 960 of de-acidified hydrolyzate 942 generates a carbon-containing co-product 964, and the method includes combining co-product 964 with de-acidified lignin 992 to form a combined product, which combined product is then thermally treated (at 980). In some embodiments, de-acidified hydrolyzate 942 includes non-fermentable compounds. In some embodiments, these non-fermentable compounds are separated prior to fermentation and combined with de-acidified lignin 992 to form the combined product. Alternatively or additionally, in some embodiments, non-fermentable compounds are kept in the fermentation feed, are separated from the product broth and combined with de-acidified lignin 992, optionally along with fermentation biomass, to form the combined products.

According to various exemplary embodiments of the invention of method 900 excess heat, or energy from the heat, (illustrated by dotted arrows) is used in at least one of pre-treatment 910 (E4), reagents recycling 950 (E1), de-acidifying 940 (E2), de-lignin de-acidification 990 (E6), hydrolyzing 290 (E7) and processing 960 (E5). Alternatively or additionally, excess heat, or energy from the heat from one reaction in oxygen deficient treating 980 is used to drive another reaction in oxygen deficient treating 980 (E3).

Additional Exemplary Methods

Figure 10A:
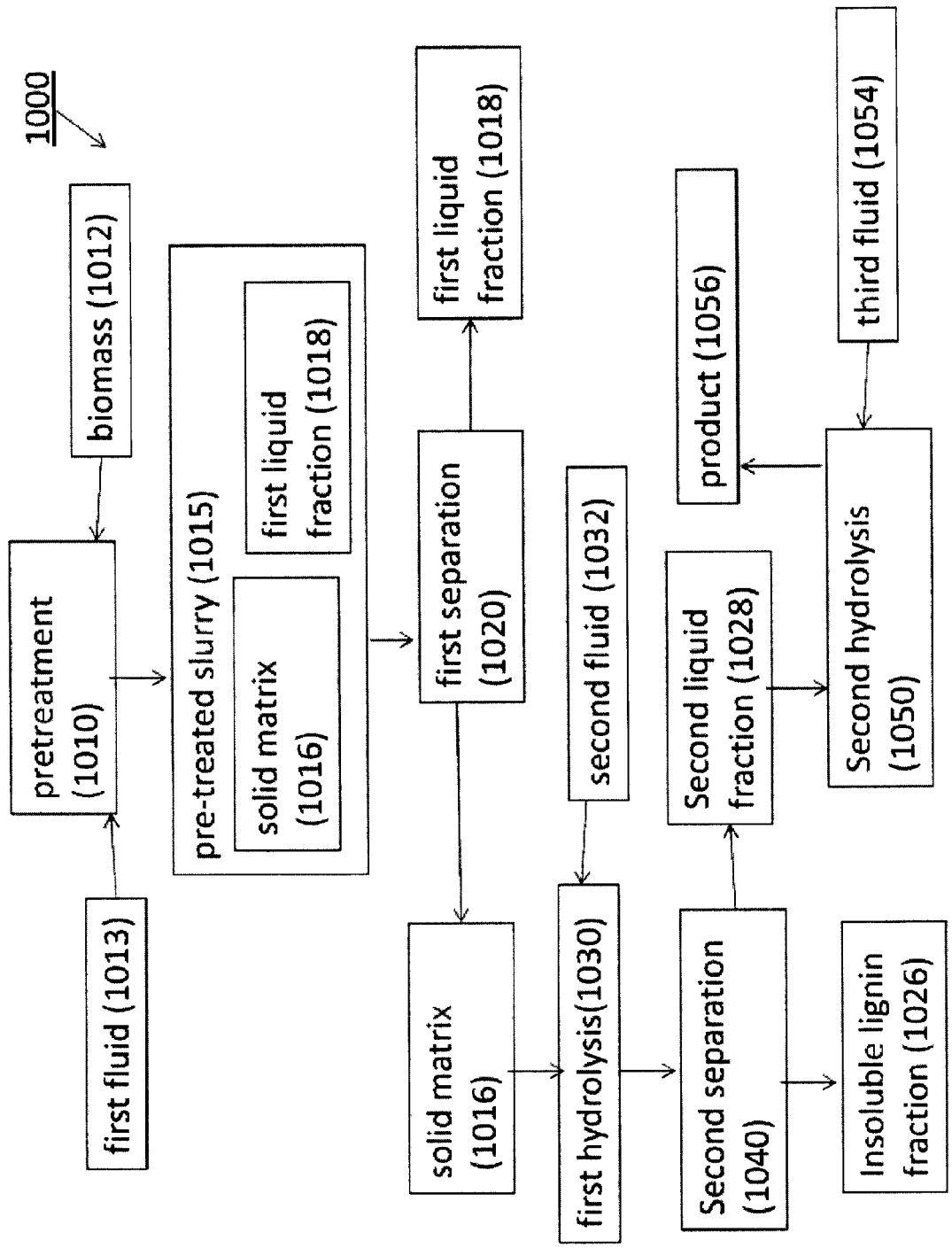
FIGS. 10a and 10b are schematic flow schemes of methods according to various exemplary embodiments of the invention.

FIG. 10*a* is a schematic representation of a method for biomass treatment indicated generally as 1000.

In some exemplary embodiments of the invention, method 1000 is for the continuous treatment of biomass and includes a pretreatment step 1010 in which biomass 1012 is contacted with a first supercritical, near-critical, or sub-critical fluid 1013 to form a solid matrix 1016 and a first liquid fraction 1018. Depicted exemplary method 1000 includes a hydrolysis step 1030 in which solid matrix 1016 is contacted with a second supercritical or near-critical fluid 1032 to produce a second liquid fraction 1028 and an insoluble lignin-containing fraction 1026.

In some embodiments, first fluid 1013 includes water and at least one of $SO_2$ and a solvent. In some embodiments, the solvent is water-miscible and does not form an azeotrope with water.

In some embodiments, second fluid 1032 includes water and at least one of $SO_2$ and a solvent. In some embodiments, the solvent is water-miscible and does not form an azeotrope with water.

In some embodiments, both first fluid 1013 and second fluid 1032 include water and at least one of $SO_2$ and a solvent as described above.

Referring again to FIG. 10*a*, in some embodiments, method 1000 includes a pretreatment step 1010 as described above which forms a pretreated slurry 1015 including solid matrix 1016 and first liquid fraction 1018 including xylo-oligosaccharides.

In some embodiments, the depicted method includes a first separation step 1020 in which solid matrix 1016 and first liquid fraction 1018 are separated and a first hydrolysis step 1030 in which solid matrix 1016 is contacted second supercritical or near-critical fluid 1032 to form an insoluble lignin-containing fraction 1026 and a second liquid fraction 1028 including cello-oligosaccharides.

In some embodiments, method 1000 includes a second separation step 1040, in which insoluble lignin-containing fraction 1026 and second liquid fraction 1028 are separated. Alternatively or additionally, in some embodiments method 1000 includes a second hydrolysis step 1050 in which second liquid fraction 1028 is contacted with a third near-critical or sub-critical fluid 1054 to form a product 1056 including glucose monomers. In some embodiments, third fluid 1054 includes water. In some embodiments, third fluid 1054 includes acid.

Referring again to FIG. 10*a*, in some embodiments, method 1000 includes a pretreatment step 1010 as described above which produces pretreated slurry 1015 as described above and first separation step 1020 as described above and first hydrolysis step 1030 as described above to form insoluble lignin-containing fraction 1026 and second liquid fraction 1028 including cello-oligosaccharides;

In some embodiments, first fluid 1013 includes water and at least one of $SO_2$ and a solvent. In some embodiments, the solvent is water-miscible and does not form an azeotrope with water In some embodiments, method 1000 includes second separation step 1040, in which insoluble lignin-containing fraction 1026 and second liquid fraction 1028 are separated and second hydrolysis step 1050 in which second liquid fraction 1028 is contacted with third near-critical or sub-critical fluid 1054 to form a product 1056 including glucose monomers. In some embodiments, third fluid 1054 includes water. In some embodiments, third fluid 1054 includes acid.

Referring again to FIG. 10*a*, in some embodiments, method 1000 includes a pretreatment step 1010 as described above wherein the first supercritical or near-critical fluid 1013 includes water and at least one of $SO_2$ and a solvent. In some embodiments, the solvent is water-miscible and does not form an azeotrope with water. In some embodiments, method 1000 includes first separation step 1020 and first hydrolysis step 1030 as described above to produce insoluble lignin-containing fraction 1026 and a second liquid fraction 1028 including cello-oligosaccharides. In some embodiments, first fluid 1013 includes water and at least one of $SO_2$ and a solvent. In some embodiments, the solvent is water-miscible and does not form an azeotrope with water. In some embodiments, method 1000 includes a second separation step 1040 in which insoluble lignin-containing fraction 1026 and second liquid fraction 1028 are separated.

In some embodiments, method 1000 includes second hydrolysis step 1050, in which second liquid fraction 1028 is contacted with third near-critical or sub-critical fluid 1054 to form product 1056 including glucose monomers. In some embodiments, third fluid 1054 includes water and/or acid.

In some embodiments, method 1000 includes a second separation step 1040 after hydrolysis 1030 which separates lignin fraction 1026 and second liquid fraction 1028.

Alternatively or additionally, in some embodiments, method 1000 includes a second hydrolysis step 1050 in which second liquid fraction 1028 is contacted with a third near-critical or sub-critical fluid 1054 to produce a third liquid fraction (depicted as product 1056) comprising glucose monomers. In some embodiments, third fluid 1054 comprises water and/or an acid.

In some embodiments, method 1000 includes a first separation step 1020 after pretreatment 1010 and prior to hydrolysis 1030 in which solid matrix 1016 and first liquid fraction 1018 are separated. In some embodiments, separation 1020 is performed using an extruder or centrifugal press.

In some embodiments, pretreatment 1010 is continuous.

In various embodiments, second liquid fraction 1028 has a residence time of 1 second, 10 seconds, 15 seconds, 20, seconds or even about 30 seconds in second hydrolysis 1050.

Figure 10B:
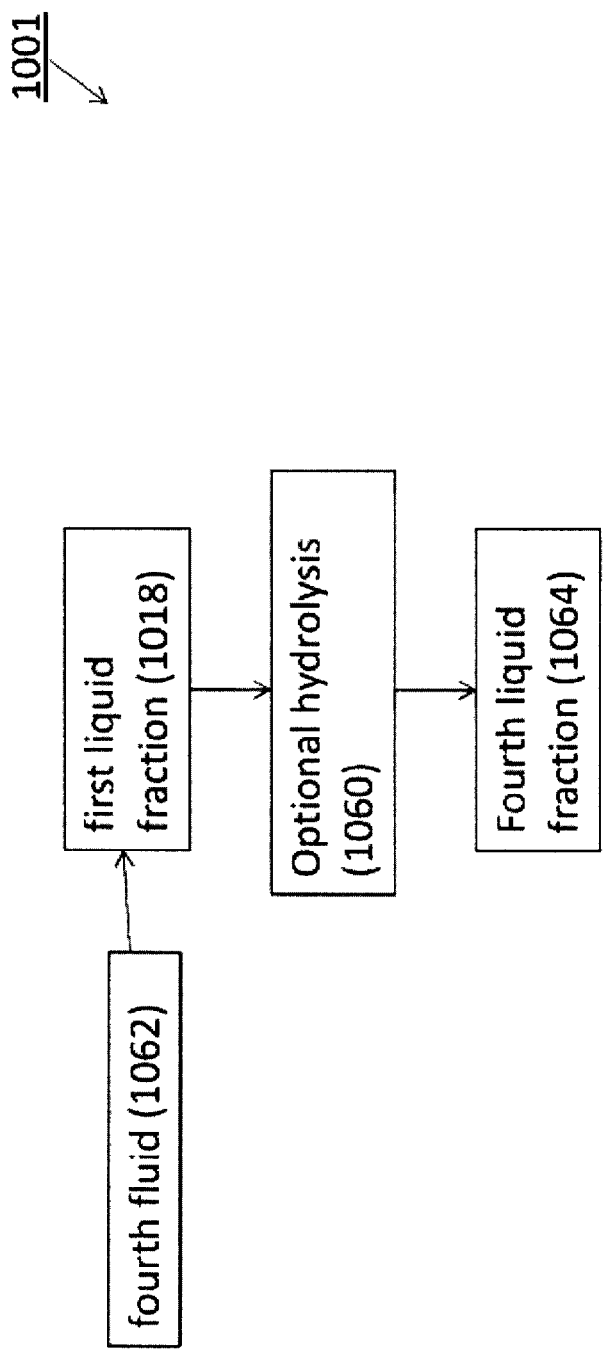

Referring now to FIG. 10*b*: In some embodiments, method 1000 includes continues with method 1001. Depicted method

1001 includes a xylo-oligosaccharide hydrolysis step 1060 in which first liquid fraction 1018 is contacted with a fourth near-critical or sub-critical fluid 1062 to produce a fourth liquid fraction 1064 comprising xylose monomers. In some embodiments, fourth fluid 1062 includes water. In some embodiments, fourth fluid 1062 includes an acid.

Depicted exemplary method 1001 includes a third hydrolysis step 1060, in which first liquid fraction 1018 (from method 1000) is contacted with a fourth near-critical or sub-critical fluid 1062 to form a second product (fourth liquid fraction 1064) comprising xylose monomers. In some embodiments, fourth fluid 1062 includes water and/or acid.

Exemplary Fluid Parameters

According to various exemplary embodiments of the invention first fluid 1013 includes at least 100 ppm, at least 500 ppm, at least 1000 ppm or even at least 2000 ppm $SO_2$. Alternatively or additionally, first fluid 1013 includes less than 10%, less than 8%, less than 6%, or even less than 4% $SO_2$. Alternatively or additionally, first fluid 1013 includes at least 10%, at least 20%, at least 30%, at least 40%, at least 50% or even at least 60% solvent.

In some embodiments, second fluid 1032 includes at least 100 ppm, at least 500 ppm, at least 1000 ppm or even at least 2000 ppm $SO_2$. Alternatively or additionally, second fluid 1032 comprises less than 10%, less than 8%, less than 6%, or even less than 4% $SO_2$.

Exemplary Reaction Conditions

In some embodiments, pretreatment step 1010 occurs at a temperature and pressure below the critical point of at least one component of first fluid 1013.

According to various exemplary embodiments of the invention pretreatment 1010 is performed at a temperature of about 100° C., 125° C., 150° C., 175° C., 200° C., 225° C., 250° C., 275° C., or even about 300° C. or intermediate or higher temperatures.

Alternatively or additionally, according to various exemplary embodiments of the invention, pretreatment 1010 is performed at a pressure of about 30 bar, 50 bar, 70 bar, 85 bar, 100 bar, 110 bar, or even about 115 bar or intermediate or higher pressures.

In some embodiments, hydrolysis step 1030 occurs at a temperature and pressure above the critical point of at least one component of second fluid 1032.

In some embodiments, hydrolysis 1030 occurs at a temperature of about 150° C., 175° C., 200° C., 250° C., 300° C., 350° C., 400° C., or even 450° C. or an intermediate or greater temperature. Alternatively or additionally, hydrolysis 1030 occurs at a pressure of about 100 bar, 125 bar, 150 bar, 175 bar, 200 bar, 225 bar, 240 bar or even about 250 bar or an intermediate or greater pressure. In some embodiments, hydrolysis 1030 is continuous.

In some embodiments, solid matrix 1016 is kept at a temperature of about 50° C., 70° C., 90° C., 110° C., 130° C. or even 150° C., or intermediate or higher temperatures from the beginning of pretreatment 1010 step through at least the end of the hydrolysis 1030.

According to various exemplary embodiments of the invention second hydrolysis 1050 occurs at a temperature of about 150° C., 175° C., 200° C., 225° C., 250° C., 280° C., 310° C., or even 320° C. or intermediate or higher temperatures.

Alternatively or additionally, according to various embodiments of the invention second hydrolysis 1050 occurs at a pressure of about 20 bar, 30 bar, 40 bar, 50 bar, 60 bar, 70 bar, 80 bar, or even 90 bar or intermediate or higher pressures.

In various embodiments, xylo-oligosaccharide hydrolysis 1060 occurs at a temperature of about 150° C., 175° C., 200° C., 225° C., 250° C., 275° C., 300° C., or even about 320° C. or intermediate or higher temperatures.

Alternatively or additionally, in various embodiments of the invention xylo-oligosaccharide hydrolysis 1060 occurs at a pressure of about 20 bar, 30 bar, 40 bar, 50 bar, 60 bar, 70 bar, 80 bar, or even about 90 bar or intermediate or higher pressures.

In some embodiments, method 1000 includes reducing pressure exerted on solid matrix 1016 such that the lignin precipitates after hydrolysis 1030. In some embodiments, the pressure exerted on solid matrix 1016 is reduced to about 110 kPa, 105 kPa, 90 kPa, 85 kPa, or even 80 kPa or less after hydrolysis 1030.

Exemplary Acid and Solvent Parameters

In some embodiments, the acid is present in a catalytic amount or in an amount less than about 1%. The acid includes one or more of hydrofluoric acid, hydrochloric acid, hydrobromic acid, hydroiodic acid, sulfuric acid, sulfonic acid, phosphoric acid, phosphonic acid, nitric acid and nitrous acid.

In some embodiments, the solvent is acetone.

In some embodiments, second fluid 1032 does not include an acid.

Exemplary Yield Considerations

In some embodiments, first liquid fraction 1018 includes xylose oligosaccharides. Alternatively or additionally, In some embodiments, first liquid fraction 1018 includes an amount of xylose oligosaccharides greater than about 50% of the maximum theoretical yield.

In some embodiments, third liquid fraction (product 1056) includes glycolaldehyde. In some embodiments, the glycolaldehyde is present in an amount at least 10%, at least 20%, or even at least 30% of the theoretical maximum yield.

Use of super critical, near critical and subcritical fluids in treatment of biomass is described in WO 2010/009343 and WO 2011/091044; each of which is fully incorporated herein by reference.

It is expected that during the life of this patent many apparatus for thermo-mechanical treatment of substrate 100 will be developed and the scope of the invention is intended to include all such new technologies a priori.

As used herein the term "about" refers to ±10%.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Specifically, a variety of numerical indicators have been utilized. It should be understood that these numerical indicators could vary even further based upon a variety of engineering principles, materials, intended use and designs incorporated into the invention. Additionally, components and/or actions ascribed to exemplary embodiments of the invention and depicted as a single unit may be divided into subunits. Conversely, components and/or actions ascribed to exemplary embodiments of the invention and depicted as subunits/individual actions may be combined into a single unit/action with the described/depicted function.

Alternatively, or additionally, features used to describe a method can be used to characterize an apparatus or system and features used to describe an apparatus or system can be used to characterize a method.

It should be further understood that the individual features described hereinabove can be combined in all possible combinations and sub-combinations to produce additional embodiments of the invention. The examples given above are illustrative in nature and do not limit the scope of the invention which is defined solely by the following claims. Specifically, the invention has been described in the context of lignocellulosic substrates but might also be used in the context of other materials.

All publications, references patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The terms "include", and "have" and their conjugates as used herein mean "including but not necessarily limited to".

Additional objects, advantages, and novel features of various embodiments of the invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Influence of Weak Acid on Extraction of Ash

In order to examine the effect of sulfurous acid on extraction of ash, as represented by calcium and magnesium ions, comparative extractions in the presence and absence of acid were conducted.

Briefly, 5.5 gr pine wood (containing 38% water and about 0.3% ash on dry basis), 13.3 gr acetone, 0-1.8 gr 5% $H_2SO_3$ solution and 0-1.74 gr water were introduced into vials.

In table 1, the initial composition of the reacted solvent is given in terms of $H_2SO_3$ wt % and acetone-water to dry wood ratio. For convenience, the extractions are grouped and ordered according to $H_2SO_3$ wt %.

Vials were closed and shaken at 55° C. for 4 hours. Liquid was removed and filtered through 0.45 micron filter and samples were taken for analysis and final composition of the acetone solution at the end of the experiment is summarized in Table 1; water content is determined by Karl Fisher test ASTM D6869; ISO 15512 and indicated in the table by water KF, Ca+Mg content is determined by titration and indicated in the table by molls (N) and weight ratio and dry weight (solids in the table) is determined by evaporation at 95° C. for 3-4 hr.

Results presented in Table 1 demonstrate that substantially no extraction of calcium and magnesium occurs in the absence of sulfurous acid (vials 5, 6 and 7) and that substantially all of the calcium and magnesium is extracted in the presence of $H_2SO$ (vials 1, 2, 3 and 4).

In addition, the total solids extraction (including lipophilic material) is also improved in the presence of sulfurous acid (vial 4).

This example illustrates that combination of a weak acid with a water-soluble solvent can contribute to efficiency of extraction of ash and/or lipophilic components from a lignocellulosic substrate such as wood.

TABLE 1 sample composition before and after extraction

| | Before extractant | | After | | | | |
|---|---|---|---|---|---|---|---|
| | | | Miscella | | | Miscella relative to dry wood | |
| vial | Acetone-water/ dry wood | $H_2SO_3$ Wt % | water KF** Wt % | solids wt % | Ca + Mg N | solids Wt % | Ca + Mg* Wt % |
| 1 | 5.04 | 0.10 | 16.3 | 0.289 | 0.0008 | 1.48 | 0.016 |
| 2 | 4.92 | 0.17 | 20.2 | 0.287 | 0.0031 | 1.43 | 0.060 |
| 3 | 5.35 | 0.20 | 24.9 | 0.266 | 0.0047 | 1.45 | 0.100 |
| 4 | 5.73 | 0.27 | 31.2 | 0.343 | 0.0062 | 2.00 | 0.142 |
| 5 | 4.34 | 0.00 | 16.4 | 0.167 | 0.0000 | 0.74 | 0.000 |
| 6 | 4.97 | 0.00 | 21.1 | 0.196 | 0.0000 | 0.99 | 0.000 |
| 7 | 5.08 | 0.00 | 23.6 | 0.306 | 0.0000 | 1.58 | 0.000 |

*Values in the table where determined by titration and calculated according to the molecular weight of Ca. Thus, the actual percentage is somewhat lower;
**Karl Fisher Example 2

Influence of Steam Explosion on Extraction

In order to examine the potential of a predetermined pressure-temperature-time profile to improve extraction efficiency three different steam explosion treatments were compared to three negative control samples as summarized in table 2.

TABLE 2

Exemplary Steam explosion (SE) parameters

| | Steam explosion | | | |
|---|---|---|---|---|
| Sample type | Duration (min) | Pressure (bar) | Symbol | Name |
| experimental | 2 | 15 | square | |
| experimental | 4 | 10 | Triangle | |
| experimental | 2 | 12 | Asterisk | |
| control | NA | NA | Diamond | NC original; pre-hammer mill |
| control | NA | NA | X | Hammer milled |
| control | NA | NA | Circle | Hammer milled |

FIG. 4 is a plot of total solids extracted from dry wood (wt %) as a function of extraction time in minutes.

The plotted data indicates that steam exploded (SE) substrate was more amenable to extraction than either pre-hammer milled (NC original) or hammer milled substrate.

The results also suggest that steam explosion at 15 bar was more effective than steam explosion at 10 or 12 bar. Increasing time at the high pressure did not seem to compensate for this effect (compare squares to triangles).

Using steam explosion for 2 minutes at 15 bar, soluble extractives were removed at ratios of up to 7%-9% from wood samples that have been treated with steam explosion and then treated with an extractant comprising acetone and sulphurous acid to remove impurities. This is in sharp contrast to untreated wood or wood treated by hammer milling before the extracting step, where at most 1.5-2.2% of extractives have been removed.

Example 3

Additional Acetone-SO$_2$ Extraction

An additional extraction of pine wood was conducted using about 15% water in acetone with an average SO2 content of 4120 PPM. Extraction temperature was in the range of 50-55° C.

Final moisture content of the miscella was determined, mainly according to the solvent/wood ratio, as well as SO$_2$ concentration. Volatiles in the extractor discharge to the desolventizer were found to have a concentration of 62% average; water in the miscella was 34.99% average, SO$_2$ in the miscella was 0.163% average; pH of the miscella was 4; pH at the bottom of the evaporator was 3; and moisture in the desolventizer discharge was 12%.

It is currently believed that the system will be able to handle up to 12,000 PPM SO$_2$ in acetone:water 90:10.

These results suggest that addition of SO$_2$ to acetone contributes to removal of cations during extraction. Overall extraction efficiency appears to be in the range of 6-7% of the dry wood weight. No significant loss of sugars is observed.

What is claimed is:

1. A lignocellulosic composition comprising (on a dry matter basis) cellulose, at least 7.4% by weight hemicellulose, and lignin, wherein said lignocellulosic composition is a solid, and further wherein said lignocellulosic composition comprises:
    (i) lipophilic material at less than 5000 PPM;
    (ii) ash at less than 2000 PPM or Ca at less than 2000 PPM;
    (iii) pectin at less than 10,000 PPM;
    (iv) furfural at less than 2000 PPM; and
    (v) at least 10 PPM of a marker selected from the group consisting of: hydroxy-methyl furfural, products of furfural condensation, products of hydroxy-methyl furfural condensation, color compounds derived from sugar caramelization, levulinic acid, acetic acid, methanol, galacturonic acid, glycerol, organically bound sulfur and acetone.

2. The lignocellulosic composition according to claim 1, wherein said composition has a moisture content of 5 to 30%.

3. The lignocellulosic composition according to claim 1 comprising Ca at less than 2000 PPM.

4. The lignocellulosic composition according to claim 3 comprising Ca at less than 1000 PPM.

5. The lignocellulosic composition according to claim 4 comprising Ca at less than 500 PPM.

6. The lignocellulosic composition according to claim 1 comprising furfural at less than 1000 PPM.

7. The lignocellulosic composition according to claim 5 comprising furfural at less than 500 PPM.

8. The lignocellulosic composition according to claim 1 comprising lipophilic material at less than 3000 PPM.

9. The lignocellulosic composition according to claim 8 comprising lipophilic material at less than 500 PPM.

10. The lignocellulosic composition according to claim 1 comprising pectin at less than 6000 PPM.

11. The lignocellulosic composition according to claim 10 comprising pectin at less than 1000 PPM.

12. The lignocellulosic composition according to claim 1 comprising ash at less than 500 PPM.

13. The lignocellulosic composition according to claim 1 comprising at least 35% by weight cellulose.

14. The lignocellulosic composition according to claim 1, wherein at least 10% of the cells are disrupted.

15. The lignocellulosic composition according to claim 1 comprising at least 0.01% acid selected from the group consisting of sulfurous acid, acetic acid and carbonic acid.

* * * * *

UNITED STATES PATENT AND TRADEMARK OFFICE
CERTIFICATE OF CORRECTION

| | | |
|---|---|---|
| PATENT NO. | : 8,404,355 B2 | Page 1 of 1 |
| APPLICATION NO. | : 13/316327 | |
| DATED | : March 26, 2013 | |
| INVENTOR(S) | : Robert Jansen et al. | |

It is certified that error appears in the above-identified patent and that said Letters Patent is hereby corrected as shown below:

In the Specifications:

1.  On page 1, column 1, line 60, please insert --IL209912 entitled "A Method for Treating a Lignocellulosic Feed Containing Ash and Fatty Acid" to Aharon Eyal et al. filed on December 9, 2010; and IL210161 entitled "A Method for Processing a Lignocellulosic Material into a Hydrolyzate Product" to Aharon Eyal filed on December 21, 2010; each of which is fully incorporated herein by reference.--

In the Claims:

2.  In Column 58, line 15, please delete "claim 5" and insert therefore --claim 6.--

Signed and Sealed this
Twenty-fifth Day of June, 2013

Teresa Stanek Rea
*Acting Director of the United States Patent and Trademark Office*